US008841439B2

(12) United States Patent  (10) Patent No.: US 8,841,439 B2
Felo et al.  (45) Date of Patent: Sep. 23, 2014

(54) NUCLEOTIDE SUGAR PURIFICATION USING MEMBRANES

(75) Inventors: Michael Felo, Havertown, PA (US); Shawn DeFrees, North Wales, PA (US)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/215,439

(22) Filed: Aug. 23, 2011

(65) Prior Publication Data

US 2012/0083600 A1  Apr. 5, 2012

Related U.S. Application Data

(62) Division of application No. 12/092,563, filed as application No. PCT/US2006/043048 on Nov. 3, 2006, now abandoned.

(60) Provisional application No. 60/733,975, filed on Nov. 3, 2005, provisional application No. 60/796,281, filed on Apr. 28, 2006, provisional application No. 60/746,754, filed on May 8, 2006, provisional application No. 60/823,538, filed on Aug. 25, 2006, provisional application No. 60/829,242, filed on Oct. 12, 2006.

(51) Int. Cl.
*C07H 19/10* (2006.01)
*C07H 1/06* (2006.01)
*C12P 19/30* (2006.01)
*C07H 19/06* (2006.01)

(52) U.S. Cl.
CPC ............. *C12P 19/305* (2013.01); *C07H 19/06* (2013.01)
USPC ....................................................... 536/26.8

(58) Field of Classification Search
CPC .............................. C12P 19/305; C07H 19/06
USPC ....................................................... 536/26.8
See application file for complete search history.

(56) References Cited

U.S. PATENT DOCUMENTS

| | | |
|---|---|---|
| 4,055,635 A | 10/1977 | Green et al. |
| 4,088,538 A | 5/1978 | Schneider |
| 4,179,337 A | 12/1979 | Davis et al. |
| 4,385,260 A | 5/1983 | Watts |
| 4,412,989 A | 11/1983 | Iwashita et al. |
| 4,414,147 A | 11/1983 | Klibanov et al. |
| 4,438,253 A | 3/1984 | Casey et al. |
| 4,451,566 A | 5/1984 | Spencer |
| 4,496,689 A | 1/1985 | Mitra |
| 4,565,653 A | 1/1986 | Ives et al. |
| 4,675,414 A | 6/1987 | DeFusco et al. |
| 4,767,702 A | 8/1988 | Cohenford |
| 4,806,595 A | 2/1989 | Noishiki et al. |
| 4,826,945 A | 5/1989 | Cohn et al. |
| 4,847,325 A | 7/1989 | Shadle et al. |
| 4,879,236 A | 11/1989 | Smith et al. |
| 4,918,009 A | 4/1990 | Nilsson |
| 4,925,796 A | 5/1990 | Bergh et al. |
| 4,980,502 A | 12/1990 | Felder et al. |
| 5,032,519 A | 7/1991 | Paulson et al. |
| 5,047,335 A | 9/1991 | Paulson et al. |
| 5,104,651 A | 4/1992 | Boone et al. |
| 5,122,614 A | 6/1992 | Zalipsky |
| 5,147,788 A | 9/1992 | Page et al. |
| 5,153,265 A | 10/1992 | Shadle et al. |
| 5,154,924 A | 10/1992 | Friden |
| 5,164,374 A | 11/1992 | Rademacher et al. |
| 5,166,322 A | 11/1992 | Shaw et al. |
| 5,169,933 A | 12/1992 | Anderson et al. |
| 5,180,674 A | 1/1993 | Roth |
| 5,182,107 A | 1/1993 | Friden |
| 5,194,376 A | 3/1993 | Kang |
| 5,202,413 A | 4/1993 | Spinu |
| 5,206,344 A | 4/1993 | Katre et al. |
| 5,219,564 A | 6/1993 | Zalipsky et al. |
| 5,272,066 A | 12/1993 | Bergh et al. |
| 5,278,299 A | 1/1994 | Wong et al. |
| 5,281,698 A | 1/1994 | Nitecki |
| 5,288,637 A | 2/1994 | Roth |
| 5,308,460 A | 5/1994 | Mazid et al. |
| 5,324,663 A | 6/1994 | Lowe |
| 5,324,844 A | 6/1994 | Zalipsky |
| 5,342,940 A | 8/1994 | Ono et al. |
| 5,346,696 A | 9/1994 | Kim et al. |
| 5,352,670 A | 10/1994 | Venot et al. |
| 5,369,017 A | 11/1994 | Wong et al. |

(Continued)

FOREIGN PATENT DOCUMENTS

| | | |
|---|---|---|
| AU | 1991/083760 A | 3/1992 |
| AU | 1992/017052 | 12/1992 |

(Continued)

OTHER PUBLICATIONS

Abeijon et al., *J. Biol. Chem.*, 261(24): 11374-11377 (1986).
Abuchowski et al., *J. Biol. Chem.*, 252(11): 3578-3581 (1977).
Abuchowski et al., *J. Biol. Chem.*, 252(11): 3582-3586 (1977).
Abuchowski et al., *Cancer Biochem. Biophys.*, 7(2): 175-186 (1984).
Adelhorst et al., *J. Biol. Chem.*, 269(9): 6275-6278 (1994).
Ailor et al., *Glycobiology*, 10(8): 837-847 (2000).
Alam et al., *J. Biotechnol.*, 65(2-3): 183-190 (1998).
Allegre et al., *J. Memb. Sci.*, 269(1-2): 109-117 (2006).
Altmann et al., *Glycoconj. J.*, 16(2): 109-123 (1999).
Amersham Pharmacia Biotech, "Hydrophobic Interaction Chromatography: Principles and Methods," 104 pp. (2000).
Aplin et al., *CRC Crit. Rev. Biochem.*, 10(4): 259-306 (1981).
Barrios et al., *J. Mol. Recognit.*, 17(4):332-338 (2004).
Beauchamp et al., *Anal. Biochem.*, 131(1): 25-33 (1983).
Bedard et al., *Cytotechnology*, 15(1-3):129-138 (1994).

(Continued)

*Primary Examiner* — Brandon Fetterolf
*Assistant Examiner* — Yih-Horng Shiao
(74) *Attorney, Agent, or Firm* — Leydig, Voit & Mayer, Ltd.

(57) ABSTRACT

The invention provides methods of removing contaminants from a mixture of a desired product and contaminants by pH adjustments and molecular weight cut-offs. The contaminants include phosphate groups, magnesium sulfate, sodium pyruvate and tetrasodium pyrophosphate groups. The desired product includes nucleotide sugars, glycolipids, LnNT, sialyl lactose, and salts.

21 Claims, 20 Drawing Sheets

(56) References Cited

U.S. PATENT DOCUMENTS

| | | |
|---|---|---|
| 5,374,541 A | 12/1994 | Wong et al. |
| 5,374,655 A | 12/1994 | Kashem et al. |
| 5,384,249 A | 1/1995 | Sasaki et al. |
| 5,399,345 A | 3/1995 | Schumacher et al. |
| 5,405,753 A | 4/1995 | Brossmer et al. |
| 5,409,817 A | 4/1995 | Ito et al. |
| 5,410,016 A | 4/1995 | Hubbell et al. |
| 5,432,059 A | 7/1995 | Bean et al. |
| 5,446,090 A | 8/1995 | Harris |
| 5,492,821 A | 2/1996 | Callstrom et al. |
| 5,492,841 A | 2/1996 | Craig |
| 5,527,527 A | 6/1996 | Friden |
| 5,529,914 A | 6/1996 | Hubbell et al. |
| 5,545,553 A | 8/1996 | Gotschlich |
| 5,567,422 A | 10/1996 | Greenwald |
| 5,583,042 A | 12/1996 | Roth |
| 5,595,900 A | 1/1997 | Lowe |
| 5,605,793 A | 2/1997 | Stemmer |
| 5,614,184 A | 3/1997 | Sytkowski et al. |
| 5,621,039 A | 4/1997 | Hallahan et al. |
| 5,629,384 A | 5/1997 | Veronese et al. |
| 5,635,603 A | 6/1997 | Hansen et al. |
| 5,643,575 A | 7/1997 | Martinez et al. |
| 5,646,113 A | 7/1997 | Attie et al. |
| 5,672,662 A | 9/1997 | Harris et al. |
| 5,672,683 A | 9/1997 | Friden et al. |
| 5,705,367 A | 1/1998 | Gotschlich |
| 5,714,166 A | 2/1998 | Tomalia et al. |
| 5,716,812 A | 2/1998 | Withers et al. |
| 5,723,121 A | 3/1998 | Takenaga et al. |
| 5,728,554 A | 3/1998 | Bayer et al. |
| 5,739,208 A | 4/1998 | Harris |
| 5,762,920 A | 6/1998 | Yung et al. |
| 5,770,420 A | 6/1998 | Lowe et al. |
| 5,798,233 A | 8/1998 | Gotschlich |
| 5,811,238 A | 9/1998 | Stemmer et al. |
| 5,824,778 A | 10/1998 | Ishikawa et al. |
| 5,824,864 A | 10/1998 | Fox et al. |
| 5,830,721 A | 11/1998 | Stemmer et al. |
| 5,833,988 A | 11/1998 | Friden |
| 5,834,251 A | 11/1998 | Maras et al. |
| 5,837,458 A | 11/1998 | Minshull et al. |
| 5,849,535 A | 12/1998 | Cunningham et al. |
| 5,858,751 A | 1/1999 | Paulson et al. |
| 5,858,752 A | 1/1999 | Seed et al. |
| 5,861,374 A | 1/1999 | Berkner et al. |
| 5,874,075 A | 2/1999 | Collins et al. |
| 5,876,980 A | 3/1999 | DeFrees et al. |
| 5,922,577 A | 7/1999 | Defrees et al. |
| 5,925,739 A | 7/1999 | Spira et al. |
| 5,932,462 A | 8/1999 | Harris et al. |
| 5,945,314 A | 8/1999 | Prieto et al. |
| 5,945,322 A | 8/1999 | Gotschlich |
| 5,955,347 A | 9/1999 | Lowe |
| 5,962,294 A | 10/1999 | Paulson et al. |
| 5,969,040 A | 10/1999 | Hallahan et al. |
| 5,977,307 A | 11/1999 | Friden et al. |
| 6,010,999 A | 1/2000 | Daley et al. |
| 6,015,555 A | 1/2000 | Friden |
| 6,030,815 A | 2/2000 | DeFrees et al. |
| 6,034,223 A | 3/2000 | Maddon et al. |
| 6,037,452 A | 3/2000 | Minamino et al. |
| 6,048,720 A | 4/2000 | Dalborg et al. |
| 6,057,292 A | 5/2000 | Cunningham et al. |
| 6,075,134 A | 6/2000 | Bertozzi et al. |
| 6,087,325 A | 7/2000 | Meers et al. |
| 6,096,512 A | 8/2000 | Elhammer et al. |
| 6,113,906 A | 9/2000 | Greenwald et al. |
| 6,117,651 A | 9/2000 | Schultz et al. |
| 6,127,153 A | 10/2000 | Johnson et al. |
| 6,166,183 A | 12/2000 | Ishikawa et al. |
| 6,183,738 B1 | 2/2001 | Clark |
| 6,251,864 B1 | 6/2001 | Dower et al. |
| 6,261,805 B1 | 7/2001 | Wood |
| 6,268,193 B1 | 7/2001 | Lowe |
| 6,319,695 B1 | 11/2001 | Wong et al. |
| 6,340,742 B1 | 1/2002 | Burg et al. |
| 6,342,382 B1 | 1/2002 | Gotschlich |
| 6,348,558 B1 | 2/2002 | Harris et al. |
| 6,361,977 B1 | 3/2002 | Bauer et al. |
| 6,362,254 B2 | 3/2002 | Harris et al. |
| 6,376,604 B2 | 4/2002 | Kozlowski |
| 6,399,336 B1 | 6/2002 | Paulson et al. |
| 6,399,337 B1 | 6/2002 | Taylor et al. |
| 6,440,703 B1 | 8/2002 | DeFrees |
| 6,458,937 B1 | 10/2002 | Bertozzi et al. |
| 6,465,220 B1 | 10/2002 | Hassan et al. |
| 6,495,365 B1 | 12/2002 | Saito et al. |
| 6,531,121 B2 | 3/2003 | Brines et al. |
| 6,555,346 B1 | 4/2003 | Kretzdorn et al. |
| 6,555,660 B2 | 4/2003 | Nissen et al. |
| 6,586,398 B1 | 7/2003 | Kinstler et al. |
| 6,692,931 B1 | 2/2004 | Reutter et al. |
| 6,693,183 B2 | 2/2004 | Natsuka et al. |
| 6,716,626 B1 | 4/2004 | Itoh et al. |
| 6,743,896 B2 | 6/2004 | Filpula et al. |
| 6,780,624 B2 | 8/2004 | Gotschlich |
| 6,800,740 B1 | 10/2004 | Cunningham et al. |
| 6,949,372 B2 | 9/2005 | Betenbaugh et al. |
| 7,094,530 B1 | 8/2006 | Sasaki et al. |
| 7,125,843 B2 | 10/2006 | DeFrees et al. |
| 7,138,371 B2 | 11/2006 | DeFrees et al. |
| 7,157,277 B2 | 1/2007 | DeFrees et al. |
| 7,173,003 B2 | 2/2007 | DeFrees et al. |
| 7,179,617 B2 | 2/2007 | DeFrees et al. |
| 7,199,223 B2 | 4/2007 | Bossard et al. |
| 7,202,208 B2 | 4/2007 | Papadimitriou |
| 7,214,660 B2 | 5/2007 | DeFrees et al. |
| 7,226,903 B2 | 6/2007 | DeFrees et al. |
| 7,229,962 B2 | 6/2007 | Chung et al. |
| 7,235,638 B2 | 6/2007 | Persson |
| 7,265,084 B2 | 9/2007 | DeFrees et al. |
| 7,265,085 B2 | 9/2007 | DeFrees et al. |
| 7,276,475 B2 | 10/2007 | DeFrees et al. |
| 7,297,511 B2 | 11/2007 | DeFrees et al. |
| 7,304,150 B1 | 12/2007 | Egrie et al. |
| 7,338,933 B2 | 3/2008 | DeFrees et al. |
| 7,368,108 B2 | 5/2008 | DeFrees et al. |
| 7,399,613 B2 | 7/2008 | DeFrees et al. |
| 7,405,198 B2 | 7/2008 | DeFrees et al. |
| 7,416,858 B2 | 8/2008 | DeFrees et al. |
| 7,439,043 B2 | 10/2008 | DeFrees et al. |
| 7,473,680 B2 | 1/2009 | DeFrees et al. |
| 7,524,813 B2 | 4/2009 | Zundel et al. |
| 7,662,933 B2 | 2/2010 | Kinstler et al. |
| 7,691,603 B2 | 4/2010 | DeFrees |
| 7,696,163 B2 | 4/2010 | DeFrees et al. |
| 7,795,210 B2 | 9/2010 | DeFrees et al. |
| 7,803,777 B2 | 9/2010 | DeFrees |
| 7,842,661 B2 | 11/2010 | DeFrees et al. |
| 7,932,364 B2 | 4/2011 | DeFrees et al. |
| 7,956,032 B2 | 6/2011 | DeFrees et al. |
| 8,008,252 B2 | 8/2011 | DeFrees et al. |
| 8,063,015 B2 | 11/2011 | DeFrees et al. |
| 8,207,112 B2 | 6/2012 | Hinderer et al. |
| 8,247,381 B2 | 8/2012 | DeFrees |
| 8,268,967 B2 | 9/2012 | DeFrees et al. |
| 8,361,961 B2 | 1/2013 | DeFrees et al. |
| 8,633,157 B2 | 1/2014 | DeFrees et al. |
| 2001/0041683 A1 | 11/2001 | Schmitz et al. |
| 2001/0043929 A1 | 11/2001 | Zalipsky et al. |
| 2002/0004483 A1 | 1/2002 | Nissen et al. |
| 2002/0016003 A1 | 2/2002 | Saxon et al. |
| 2002/0019342 A1 | 2/2002 | Bayer |
| 2002/0037841 A1 | 3/2002 | Papadimitriou |
| 2002/0068347 A1 | 6/2002 | Taylor et al. |
| 2002/0115833 A1 | 8/2002 | Burg et al. |
| 2002/0137134 A1 | 9/2002 | Gerngross et al. |
| 2002/0142370 A1 | 10/2002 | Paulson et al. |
| 2002/0142964 A1 | 10/2002 | Nissen et al. |
| 2002/0148791 A1* | 10/2002 | DeFrees ............... 210/767 |
| 2002/0150981 A1 | 10/2002 | Canfield |
| 2002/0168323 A1 | 11/2002 | Gonda |
| 2002/0182586 A1 | 12/2002 | Morris et al. |

(56) References Cited

U.S. PATENT DOCUMENTS

| | | |
|---|---|---|
| 2003/0027257 A1 | 2/2003 | Iatrou et al. |
| 2003/0040037 A1 | 2/2003 | Bayer |
| 2003/0083251 A1 | 5/2003 | Westenfelder |
| 2003/0096338 A1 | 5/2003 | Pedersen et al. |
| 2003/0100075 A1 | 5/2003 | Persson et al. |
| 2003/0119090 A1 | 6/2003 | Wong |
| 2003/0124645 A1 | 7/2003 | Paulson et al. |
| 2003/0166212 A1 | 9/2003 | Taylor et al. |
| 2003/0166525 A1 | 9/2003 | Hoffmann et al. |
| 2003/0170863 A1 | 9/2003 | Persson et al. |
| 2003/0180835 A1 | 9/2003 | Bayer |
| 2003/0186850 A1 | 10/2003 | Clausen et al. |
| 2003/0195338 A1 | 10/2003 | Chung et al. |
| 2003/0207406 A1 | 11/2003 | Johnson et al. |
| 2004/0020857 A1 | 2/2004 | Belew et al. |
| 2004/0043446 A1 | 3/2004 | DeFrees et al. |
| 2004/0063911 A1 | 4/2004 | DeFrees et al. |
| 2004/0077836 A1 | 4/2004 | DeFrees et al. |
| 2004/0082026 A1 | 4/2004 | DeFrees et al. |
| 2004/0102607 A1 | 5/2004 | Danishefsky et al. |
| 2004/0115168 A1 | 6/2004 | DeFrees et al. |
| 2004/0126838 A1 | 7/2004 | DeFrees et al. |
| 2004/0132640 A1 | 7/2004 | DeFrees et al. |
| 2004/0136955 A1 | 7/2004 | Barker et al. |
| 2004/0137557 A1 | 7/2004 | DeFrees et al. |
| 2004/0142856 A1 | 7/2004 | DeFrees et al. |
| 2004/0197875 A1 | 10/2004 | Hauser et al. |
| 2005/0026266 A1 | 2/2005 | Clausen et al. |
| 2005/0031584 A1 | 2/2005 | DeFrees et al. |
| 2005/0064540 A1 | 3/2005 | DeFrees et al. |
| 2005/0085631 A1 | 4/2005 | Boyle et al. |
| 2005/0100982 A1 | 5/2005 | DeFrees et al. |
| 2005/0106658 A1 | 5/2005 | DeFrees et al. |
| 2005/0113565 A1 | 5/2005 | Klausen et al. |
| 2005/0118672 A1 | 6/2005 | DeFrees et al. |
| 2005/0143292 A1 | 6/2005 | DeFrees et al. |
| 2005/0250678 A1 | 11/2005 | DeFrees et al. |
| 2005/0269265 A1 | 12/2005 | DeFrees |
| 2005/0271690 A1 | 12/2005 | Gotschlich |
| 2005/0288490 A1 | 12/2005 | Nakamoto et al. |
| 2006/0024286 A1 | 2/2006 | Glidden |
| 2006/0029573 A1 | 2/2006 | Shen et al. |
| 2006/0030521 A1 | 2/2006 | DeFrees et al. |
| 2006/0035224 A1 | 2/2006 | Johansen |
| 2006/0040856 A1* | 2/2006 | DeFrees et al. ............... 514/8 |
| 2006/0088906 A1 | 4/2006 | DeFrees et al. |
| 2006/0111279 A1 | 5/2006 | DeFrees et al. |
| 2006/0165728 A1 | 7/2006 | Young et al. |
| 2006/0177892 A1 | 8/2006 | DeFrees |
| 2006/0182714 A1 | 8/2006 | Behrens et al. |
| 2006/0183198 A1 | 8/2006 | Buechler et al. |
| 2006/0246544 A1 | 11/2006 | Kang et al. |
| 2006/0276618 A1 | 12/2006 | DeFrees et al. |
| 2006/0287223 A1 | 12/2006 | DeFrees et al. |
| 2006/0287224 A1 | 12/2006 | DeFrees et al. |
| 2007/0014759 A1 | 1/2007 | DeFrees et al. |
| 2007/0026485 A1 | 2/2007 | DeFrees et al. |
| 2007/0027068 A1 | 2/2007 | DeFrees et al. |
| 2007/0032405 A1 | 2/2007 | DeFrees et al. |
| 2007/0037966 A1 | 2/2007 | Rasmussen et al. |
| 2007/0042458 A1 | 2/2007 | DeFrees et al. |
| 2007/0059275 A1 | 3/2007 | DeFrees et al. |
| 2007/0105755 A1 | 5/2007 | DeFrees et al. |
| 2007/0111926 A1 | 5/2007 | Zundel et al. |
| 2007/0154992 A1 | 7/2007 | DeFrees |
| 2007/0254834 A1 | 11/2007 | DeFrees et al. |
| 2007/0254836 A1 | 11/2007 | DeFrees et al. |
| 2008/0015142 A1 | 1/2008 | DeFrees et al. |
| 2008/0039373 A1 | 2/2008 | Klausen et al. |
| 2008/0050772 A1 | 2/2008 | DeFrees et al. |
| 2008/0070275 A1 | 3/2008 | DeFrees et al. |
| 2008/0102083 A1 | 5/2008 | DeFrees et al. |
| 2008/0108557 A1 | 5/2008 | Behrens et al. |
| 2008/0146494 A1 | 6/2008 | DeFrees et al. |
| 2008/0146782 A1 | 6/2008 | DeFrees et al. |
| 2008/0176790 A1 | 7/2008 | DeFrees |
| 2008/0187955 A1 | 8/2008 | DeFrees et al. |
| 2008/0200651 A1 | 8/2008 | Ostergaard et al. |
| 2008/0206808 A1 | 8/2008 | DeFrees et al. |
| 2008/0206810 A1 | 8/2008 | Johnson et al. |
| 2008/0207487 A1 | 8/2008 | DeFrees et al. |
| 2008/0242607 A1 | 10/2008 | DeFrees |
| 2008/0242846 A1 | 10/2008 | DeFrees et al. |
| 2008/0248959 A1 | 10/2008 | DeFrees |
| 2008/0253992 A1 | 10/2008 | DeFrees et al. |
| 2008/0255026 A1 | 10/2008 | DeFrees et al. |
| 2008/0255040 A1 | 10/2008 | DeFrees |
| 2008/0274958 A1 | 11/2008 | DeFrees |
| 2008/0280818 A1 | 11/2008 | DeFrees |
| 2008/0300173 A1 | 12/2008 | DeFrees |
| 2008/0300175 A1 | 12/2008 | DeFrees et al. |
| 2008/0305518 A1 | 12/2008 | Klausen et al. |
| 2008/0305991 A1 | 12/2008 | DeFrees et al. |
| 2008/0305992 A1 | 12/2008 | DeFrees et al. |
| 2008/0318850 A1 | 12/2008 | DeFrees et al. |
| 2008/0319183 A1 | 12/2008 | DeFrees et al. |
| 2009/0028822 A1 | 1/2009 | DeFrees et al. |
| 2009/0048440 A1 | 2/2009 | Felo et al. |
| 2009/0053167 A1 | 2/2009 | DeFrees |
| 2009/0054623 A1 | 2/2009 | DeFrees |
| 2009/0055942 A1 | 2/2009 | Ostergaard et al. |
| 2009/0076237 A1 | 3/2009 | Turecek et al. |
| 2009/0081188 A1 | 3/2009 | DeFrees et al. |
| 2009/0093399 A1 | 4/2009 | DeFrees et al. |
| 2009/0124544 A1 | 5/2009 | DeFrees |
| 2009/0137763 A1 | 5/2009 | DeFrees et al. |
| 2009/0143292 A1 | 6/2009 | Hinderer et al. |
| 2009/0169509 A1 | 7/2009 | DeFrees et al. |
| 2009/0176967 A1 | 7/2009 | Stennicke |
| 2009/0203579 A1 | 8/2009 | DeFrees et al. |
| 2009/0227504 A1 | 9/2009 | Klausen et al. |
| 2009/0240028 A1 | 9/2009 | Behrens et al. |
| 2009/0247450 A1 | 10/2009 | Mack |
| 2009/0252720 A1 | 10/2009 | Ostergaard et al. |
| 2009/0253166 A1 | 10/2009 | Zundel et al. |
| 2009/0264366 A1 | 10/2009 | Johansen et al. |
| 2009/0292110 A1 | 11/2009 | DeFrees |
| 2009/0305967 A1 | 12/2009 | DeFrees et al. |
| 2010/0009902 A1 | 1/2010 | DeFrees |
| 2010/0015684 A1 | 1/2010 | DeFrees et al. |
| 2010/0028939 A1 | 2/2010 | Behrens et al. |
| 2010/0029555 A1 | 2/2010 | Tonon et al. |
| 2010/0035299 A1 | 2/2010 | DeFrees et al. |
| 2010/0041872 A1 | 2/2010 | DeFrees et al. |
| 2010/0048456 A1 | 2/2010 | DeFrees et al. |
| 2010/0056428 A1 | 3/2010 | Behrens |
| 2010/0075375 A1 | 3/2010 | DeFrees et al. |
| 2010/0081791 A1 | 4/2010 | DeFrees et al. |
| 2010/0113743 A1 | 5/2010 | DeFrees et al. |
| 2010/0120666 A1 | 5/2010 | Zopf et al. |
| 2010/0174056 A1 | 7/2010 | Gillies et al. |
| 2010/0174059 A1 | 7/2010 | DeFrees et al. |
| 2010/0210507 A9 | 8/2010 | DeFrees et al. |
| 2010/0286067 A1 | 11/2010 | DeFrees |
| 2010/0322940 A1 | 12/2010 | Bayer |
| 2010/0330645 A1 | 12/2010 | DeFrees et al. |
| 2010/0331489 A1 | 12/2010 | DeFrees |
| 2011/0003744 A1 | 1/2011 | DeFrees et al. |
| 2011/0177029 A1 | 7/2011 | DeFrees |
| 2011/0223646 A1 | 9/2011 | Schwartz et al. |
| 2011/0318780 A1 | 12/2011 | DeFrees |
| 2012/0016105 A1 | 1/2012 | DeFrees et al. |
| 2012/0083600 A1 | 4/2012 | Felo et al. |
| 2012/0107867 A1 | 5/2012 | DeFrees et al. |
| 2012/0172300 A1 | 7/2012 | DeFrees |
| 2012/0220517 A1 | 8/2012 | DeFrees et al. |
| 2013/0059780 A1 | 3/2013 | DeFrees |

FOREIGN PATENT DOCUMENTS

| | | |
|---|---|---|
| CA | 2131703 A1 | 9/1993 |
| CA | 2110543 A1 | 6/1994 |
| CA | 2324616 A1 | 9/1999 |
| CA | 2167521 | 10/2003 |

(56) References Cited

FOREIGN PATENT DOCUMENTS

| | | |
|---|---|---|
| CA | 2500389 A1 | 4/2004 |
| CA | 2511814 A1 | 7/2004 |
| DE | 2437388 | 2/1975 |
| DE | 19709787 | 9/1998 |
| DE | 19852729 A1 | 5/2000 |
| EP | 0119539 A2 | 9/1984 |
| EP | 0200421 A2 | 12/1986 |
| EP | 0370205 A2 | 5/1990 |
| EP | 0459630 A2 | 12/1991 |
| EP | 0474313 A2 | 3/1992 |
| EP | 0475354 A2 | 3/1992 |
| EP | 0577580 A2 | 1/1994 |
| EP | 0585109 A2 | 3/1994 |
| EP | 0605963 A2 | 7/1994 |
| EP | 0775711 A1 | 5/1997 |
| EP | 0863154 A1 | 9/1998 |
| EP | 1260582 A1 | 11/2002 |
| EP | 1270642 A1 | 1/2003 |
| EP | 1428878 A1 | 6/2004 |
| EP | 1481985 A1 | 12/2004 |
| FI | 922515 A | 12/1992 |
| GB | 2256197 A | 12/1992 |
| JP | S59172425 A | 9/1984 |
| JP | H03-503759 A | 8/1991 |
| JP | H06-086684 A | 3/1994 |
| JP | H07-196925 A | 8/1995 |
| JP | H07-223921 A | 8/1995 |
| JP | H08-506023 A | 7/1996 |
| JP | H09-503905 A | 4/1997 |
| JP | H09-208461 A | 8/1997 |
| JP | H10-307356 A | 11/1998 |
| JP | 2000-501607 A | 2/2000 |
| JP | 2001-508783 A | 7/2001 |
| JP | 2001-519784 A | 10/2001 |
| JP | 2003-521930 A | 7/2003 |
| JP | 2005-521635 A | 7/2005 |
| JP | 2005-328782 A | 12/2005 |
| KR | 2002-0010363 A | 2/2002 |
| KR | 10-0396983 B1 | 8/2003 |
| NZ | 532027 A | 9/2008 |
| NZ | 539415 A | 12/2008 |
| NZ | 547554 A | 9/2009 |
| RU | 2005/101348 A | 8/2005 |
| SE | 9501285 | 10/1996 |
| WO | WO 87/00056 A1 | 1/1987 |
| WO | WO 87/05330 A1 | 9/1987 |
| WO | WO 89/06546 A1 | 7/1989 |
| WO | WO 89/10134 A1 | 11/1989 |
| WO | WO 90/07572 A1 | 7/1990 |
| WO | WO 90/08164 A1 | 7/1990 |
| WO | WO 90/08823 A1 | 8/1990 |
| WO | WO 90/12090 A1 | 10/1990 |
| WO | WO 90/13540 A1 | 11/1990 |
| WO | WO 91/06635 A1 | 5/1991 |
| WO | WO 91/09122 | 6/1991 |
| WO | WO 91/14697 A1 | 10/1991 |
| WO | WO 92/01055 A1 | 1/1992 |
| WO | WO 92/15686 A1 | 9/1992 |
| WO | WO 92/16555 A1 | 10/1992 |
| WO | WO 92/16640 A1 | 10/1992 |
| WO | WO 92/18135 A1 | 10/1992 |
| WO | WO 92/22310 A1 | 12/1992 |
| WO | WO 93/08842 A1 | 5/1993 |
| WO | WO 93/13198 A1 | 7/1993 |
| WO | WO 93/15189 A1 | 8/1993 |
| WO | WO 93/18787 A1 | 9/1993 |
| WO | WO 94/04193 A1 | 3/1994 |
| WO | WO 94/05332 A2 | 3/1994 |
| WO | WO 94/09027 A1 | 4/1994 |
| WO | WO 94/15625 A1 | 7/1994 |
| WO | WO 94/17039 A1 | 8/1994 |
| WO | WO 94/18247 A1 | 8/1994 |
| WO | WO 94/25614 A1 | 11/1994 |
| WO | WO 94/25615 A1 | 11/1994 |
| WO | WO 94/26760 A1 | 11/1994 |
| WO | WO 94/27631 A1 | 12/1994 |
| WO | WO 94/28024 A1 | 12/1994 |
| WO | WO 95/02421 A1 | 1/1995 |
| WO | WO 95/04278 A1 | 2/1995 |
| WO | WO 95/05465 A1 | 2/1995 |
| WO | WO 96/10089 A1 | 4/1996 |
| WO | WO 96/11953 A1 | 4/1996 |
| WO | WO 96/12800 A1 | 5/1996 |
| WO | WO 96/21468 A1 | 7/1996 |
| WO | WO 96/21469 A1 | 7/1996 |
| WO | WO 96/32491 A1 | 10/1996 |
| WO | WO 96/32492 A1 | 10/1996 |
| WO | WO 96/34015 A1 | 10/1996 |
| WO | WO 96/36357 A1 | 11/1996 |
| WO | WO 96/40731 A1 | 12/1996 |
| WO | WO 96/40881 A1 | 12/1996 |
| WO | WO 97/05330 A1 | 2/1997 |
| WO | WO 97/21822 A2 | 6/1997 |
| WO | WO 97/47651 A1 | 12/1997 |
| WO | WO 98/05363 A2 | 2/1998 |
| WO | WO 98/31826 A1 | 7/1998 |
| WO | WO 98/32466 A1 | 7/1998 |
| WO | WO 98/41562 A1 | 9/1998 |
| WO | WO 98/51784 A1 | 11/1998 |
| WO | WO 98/58964 A1 | 12/1998 |
| WO | WO 99/00150 A2 | 1/1999 |
| WO | WO 99/13063 A1 | 3/1999 |
| WO | WO 99/14259 A1 | 3/1999 |
| WO | WO 99/22764 A1 | 5/1999 |
| WO | WO 99/28491 A1 | 6/1999 |
| WO | WO 99/34833 A1 | 7/1999 |
| WO | WO 99/37779 A1 | 7/1999 |
| WO | WO 99/45964 A1 | 9/1999 |
| WO | WO 99/48515 A1 | 9/1999 |
| WO | WO 99/54342 A1 | 10/1999 |
| WO | WO 99/55376 A1 | 11/1999 |
| WO | WO 00/23114 A2 | 4/2000 |
| WO | WO 00/26354 A1 | 5/2000 |
| WO | WO 00/29558 A1 | 5/2000 |
| WO | WO 00/29603 A2 | 5/2000 |
| WO | WO 00/44785 A1 | 8/2000 |
| WO | WO 00/46379 A1 | 8/2000 |
| WO | WO 00/65087 A1 | 11/2000 |
| WO | WO 01/02017 A2 | 1/2001 |
| WO | WO 01/05434 A2 | 1/2001 |
| WO | WO 01/19955 A2 | 3/2001 |
| WO | WO 01/39788 A2 | 6/2001 |
| WO | WO 01/49830 A2 | 7/2001 |
| WO | WO 01/51510 A2 | 7/2001 |
| WO | WO 01/58493 A1 | 8/2001 |
| WO | WO 01/58935 A2 | 8/2001 |
| WO | WO 01/60411 A1 | 8/2001 |
| WO | WO 01/76640 A2 | 10/2001 |
| WO | WO 01/83725 A1 | 11/2001 |
| WO | WO 01/87329 A1 | 11/2001 |
| WO | WO 01/87925 A2 | 11/2001 |
| WO | WO 01/88117 A2 | 11/2001 |
| WO | WO 02/02597 A2 | 1/2002 |
| WO | WO 02/02764 A2 | 1/2002 |
| WO | WO 02/13843 A2 | 2/2002 |
| WO | WO 02/13873 A2 | 2/2002 |
| WO | WO 02/29025 A2 | 4/2002 |
| WO | WO 02/44196 A1 | 6/2002 |
| WO | WO 02/49673 A2 | 6/2002 |
| WO | WO 02/50099 A2 | 6/2002 |
| WO | WO 02/053580 A2 | 7/2002 |
| WO | WO 02/074806 A2 | 9/2002 |
| WO | WO 02/077218 A1 | 10/2002 |
| WO | WO 02/092619 A2 | 11/2002 |
| WO | WO 03/006501 A2 | 1/2003 |
| WO | WO 03/011879 A1 | 2/2003 |
| WO | WO 03/017949 A2 | 3/2003 |
| WO | WO 03/029291 A2 | 4/2003 |
| WO | WO 03/031464 A2 | 4/2003 |
| WO | WO 04/029090 A1 | 4/2003 |
| WO | WO 03/045980 A2 | 6/2003 |
| WO | WO 03/046150 A2 | 6/2003 |
| WO | WO 03/093448 A2 | 11/2003 |
| WO | WO 04/000366 A1 | 12/2003 |

(56) References Cited

FOREIGN PATENT DOCUMENTS

| | | |
|---|---|---|
| WO | WO 2004/009838 A2 | 1/2004 |
| WO | WO 2004/010327 A2 | 1/2004 |
| WO | WO 2004/014417 A2 | 2/2004 |
| WO | WO 2004/022004 A2 | 3/2004 |
| WO | WO 2004/029091 A2 | 4/2004 |
| WO | WO 2004/033651 A2 | 4/2004 |
| WO | WO 2004/046222 A1 | 6/2004 |
| WO | WO 2004/047858 A1 | 6/2004 |
| WO | WO 2004/067566 A1 | 8/2004 |
| WO | WO 2004/075923 A2 | 9/2004 |
| WO | WO 2004/083258 A2 | 9/2004 |
| WO | WO 2004/083259 A2 | 9/2004 |
| WO | WO 2004/091499 A2 | 10/2004 |
| WO | WO 2004/093823 A2 | 11/2004 |
| WO | WO 2004/096148 A2 | 11/2004 |
| WO | WO 2004/099231 A2 | 11/2004 |
| WO | WO 2004/101597 A2 | 11/2004 |
| WO | WO 2004/101740 A2 | 11/2004 |
| WO | WO 2004/103275 A2 | 12/2004 |
| WO | WO 2004/106373 A1 | 12/2004 |
| WO | WO 2005/001025 A2 | 1/2005 |
| WO | WO 2005/003171 A2 | 1/2005 |
| WO | WO 2005/012484 A2 | 2/2005 |
| WO | WO 2005/014024 A2 | 2/2005 |
| WO | WO 2005/014035 A2 | 2/2005 |
| WO | WO 2005/025606 A1 | 3/2005 |
| WO | WO 2005/051327 A2 | 6/2005 |
| WO | WO 2005/055946 A2 | 6/2005 |
| WO | WO 2005/055950 A2 | 6/2005 |
| WO | WO 2005/056760 A2 | 6/2005 |
| WO | WO 2005/067601 A2 | 7/2005 |
| WO | WO 2005/070138 A2 | 8/2005 |
| WO | WO 2005/072371 A2 | 8/2005 |
| WO | WO 2005/079363 A2 | 9/2005 |
| WO | WO 2005/091944 A2 | 10/2005 |
| WO | WO 2005/121331 A2 | 12/2005 |
| WO | WO 2006/005058 A2 | 1/2006 |
| WO | WO 2006/010143 A2 | 1/2006 |
| WO | WO 2006/011839 A1 | 2/2006 |
| WO | WO 2006/013202 A2 | 2/2006 |
| WO | WO 2006/014349 A2 | 2/2006 |
| WO | WO 2006/014466 A2 | 2/2006 |
| WO | WO 2006/018204 A1 | 2/2006 |
| WO | WO 2006/020372 A2 | 2/2006 |
| WO | WO 2006/031811 A2 | 3/2006 |
| WO | WO 2006/035057 A1 | 4/2006 |
| WO | WO 2006/050247 A2 | 5/2006 |
| WO | WO 2006/053299 A2 | 5/2006 |
| WO | WO 2006/074279 A1 | 7/2006 |
| WO | WO 2006/074467 A2 | 7/2006 |
| WO | WO 2006/078645 A2 | 7/2006 |
| WO | WO 2006/082517 A1 | 8/2006 |
| WO | WO 2006/103298 A2 | 10/2006 |
| WO | WO 2006/105426 A2 | 10/2006 |
| WO | WO 2006/119987 A2 | 11/2006 |
| WO | WO 2006/121569 A2 | 11/2006 |
| WO | WO 2006/127910 A2 | 11/2006 |
| WO | WO 2006/134173 A2 | 12/2006 |
| WO | WO 2007/022512 A2 | 2/2007 |
| WO | WO 2007/056191 A2 | 5/2007 |
| WO | WO 2007/135182 A2 | 11/2007 |
| WO | WO 2008/011633 A2 | 1/2008 |
| WO | WO 2008/057683 A2 | 5/2008 |
| WO | WO 2008/060780 A2 | 5/2008 |
| WO | WO 2008/073620 A2 | 6/2008 |
| WO | WO 2008/124406 A2 | 10/2008 |
| WO | WO 2008/151258 A2 | 12/2008 |
| WO | WO 2008/154639 A2 | 12/2008 |
| WO | WO 2009/089396 A2 | 7/2009 |

OTHER PUBLICATIONS

Bennett et al., *J. Biol. Chem.*, 273(46): 30472-30481 (1998).
Bennett et al., *FEBS Lett.*, 460(2): 226-230 (1999).
Berger et al., *Blood*, 71(6): 1641-1647 (1988).
Berg-Fussman et al., *J. Biol. Chem.*, 268(20): 14861-14866 (1993).
Bhadra et al., *Pharmazie*, 57(1): 5-29 (2002).
Bhatia et al., *Anal. Biochem.*, 178(2): 408-413 (1989).
Bickel et al., *Adv. Drug Deliv. Rev.*, 46(1-3): 247-279 (2001).
Bjoern et al., *J. Biol. Chem.*, 266(17): 11051-11057 (1991).
Boccu et al., *Z. Naturforsch.*, 38c: 94-99 (1983).
Boime et al., *Recent Prog. Horm. Res.*, 54: 271-289 (1999).
Boissel et al., *J. Biol. Chem.*, 268(21): 15983-15993 (1993).
Bork et al., *Trends Genet.*, 12(10): 425-427 (1996).
Bork, *Genome Res.*, 10(4): 398-400 (2000).
Bouizar et al., *Eur. J. Biochem.*, 155(1): 141-147 (1986).
Boyd et al., *Mol. Immunol.*, 32(17-18): 1311-1318 (1995).
Brenner, *Trends Genet.*, 15(4): 132-133 (1999).
Brockhausen et al., *Acta Anatomica*, 161: 36-78 (1998).
Brockhausen et al., *Glycoconj. J.*, 15: 595-603 (1998).
Broun et al., *Science*, 282(5392): 1315-1317 (1998).
Browning et al., *J. Immunol.*, 143(6): 1859-1867 (1989).
Buckmann et al., *Makromol. Chem.*, 182(5): 1379-1384 (1981).
Burns et al., *Blood*, 99(12): 4400-4405 (2002).
Butnev et al., *Biol. Reprod.*, 58(2): 458-469 (1998).
Byun et al., *ASAIO J.*, 38(3): M649-M653 (1992).
Cantin et al., *Am. J. Respir. Cell Mol. Biol.*, 27(6): 659-665 (2002).
Casares et al., *Nat. Biotechnol.*, 19(2): 142-147 (2001).
Chaffee et al., *J. Clin. Invest.*, 89(5): 1643-1651 (1992).
Charter et al., *Glycobiology*, 10(10): 1049-1056 (2000).
Chern et al., *Eur. J. Biochem.*, 202(2): 225-229 (1991).
Chiba et al., *Biochem. J.*, 308(2): 405-409 (1995).
Chrisey et al., *Nucleic Acids Res.*, 24(15): 3031-3039 (1996).
Clark et al., *J. Biol. Chem.*, 271(36): 21969-21977 (1996).
Cohn et al., *J. Biomed. Mater. Res,.* 22(11): 993-1009 (1988).
Cointe et al., *Glycobiology*, 10(5): 511-519 (2000).
Conradt et al., *J. Biol. Chem.*, 262(30): 14600-14605 (1987).
Cope et al., *Mol. Microbiol.*, 5(5): 1113-1124 (1991).
Copeland, "Enzymes: A Practical Introduction to Structure, Mechanism and Data Analysis" 2nd ed., Wiley-VCH, New York, pp. 146-150 (2000).
Costa et al., *J. Biol. Chem.*, 272(17): 11613-11621 (1997).
Crout et al., *Curr. Opin. Chem. Biol.*, 2(1): 98-111 (1998).
Culajay et al., *Biochem.*, 39: 7153-7158 (2000).
DeFrees et al., *Glycobiology*, 16(9): 833-843 (2006).
Delgado et al., *Biotechnol. Appl. Biochem.*, 12(2): 119-128 (1990).
Delgado et al., *Crit. Rev. Ther. Drug Carrier Syst.*, 9(3-4): 249-304 (1992).
De Vries et al, *J. Biol. Chem.*, 270(15): 8712-8722 (1995).
Dinter et al., *Biotechnol. Lett.*, 22(1): 25-30 (2000).
Doerks et al., *Trends Genet.*, 14(6): 248-250 (1998).
Douglas et al., *J. Am. Chem. Soc.*, 113(13): 5095-5097 (1991).
Dubé et al., *J. Biol. Chem.*, 263(33): 17516-17521 (1988).
Dumas et al., *Bioorg. Med. Chem. Lett.*, 1(8): 425-428 (1991).
Dunn, 1991, "Polymeric Drugs and Drug Delivery Systems" Dunn et al. (eds.), Chapter 2 "Polymeric Matrices", pp. 11-23, ACS Symposium Series vol. 469, American Chemical Society, Washington D.C.
Durieux et al., *Tetrahedron Lett.*, 42(12): 2297-2299 (2001).
Dwek et al., *J. Anat.*, 187(Pt. 2): 279-292 (1995).
Eavarone et al., *J. Biomed. Mater. Res.*, 51(1): 10-14 (2000).
Edge et al., *Anal. Biochem.*, 118(1): 131-137 (1981).
Fairhall et al., Endocrinology, 131(4): 1963-1969 (1992).
Fan et al., *J. Biol. Chem.*, 272(43): 27058-27064 (1997).
Feldman et al., *Proc. Natl. Acad. Sci. USA*, 102(8): 3016-3021 (2005).
Felix et al., *J. Peptide Res.*, 63: 85-90 (2004).
Fibi et al., *Blood*, 85(5): 1229-1236 (1995).
Fischer et al., *Thromb. Res.*, 89(3): 147-150 (1998).
Flynn et al., *Curr. Opin. Oncol.*, 12(6): 574-581 (2000).
Francis et al., *Intl. J. Hematol.*, 68(1): 1-18 (1998).
Fritz et al., *Proc. Natl. Acad. Sci. USA*, 101(43): 15307-15312 (2004).
Fritz et al., *J. Biol. Chem.*, 281(13): 8613-8619 (2006).
Garnett et al., *Adv. Drug Deliv. Rev.*, 53(2): 171-216 (2002).
Gatot et al., *J. Biol. Chem.*, 273(21): 12870-12880 (1998).
Ge et al., *J. Biol. Chem.*, 272(34): 21357-21363 (1997).
Gervais et al., *Glycobiology*, 13(3): 179-189 (2003).
Gilbert et al., *Cytotechnology*, 22(1-3): 211-216 (1996).
Gillis et al., *Behring Inst. Mitt.*, 83: 1-7 (1988).

(56) References Cited

OTHER PUBLICATIONS

Ginns, PEG Glucocerebrosidase, Internet page from www.gaucher. org.uk/peg2.prg, Nov. 1994, printed Jun. 21, 2002.
Gombotz et al., "PEGylation: A Tool for Enhanced Protein Delivery," in *Controlled Drug Delivery*, Park et al. (eds.), Chapter 12, pp. 110-123, ACS Symposium Series, American Chemical Society, Washington D.C. (2000).
Gotschlich, *J. Exp. Med.*, 180(6): 2181-2190 (1994).
Grabenhorst et al., *Eur. J. Biochem.*, 215(1): 189-197 (1993).
Grabenhorst et al., *J. Biol. Chem.*, 274(51): 36107-36116 (1999).
Grodberg et al., *Eur. J. Biochem.*, 218(2): 597-601 (1993).
Gross et al., *Biochemistry*, 28(18): 7386-7392 (1989).
Gross, *Eur. J. Biochem.*, 203(1-2): 269-275 (1992).
Hagen et al., *J. Biol. Chem.*, 274(10): 6797-6803 (1999).
Hagen et al., *J. Biol. Chem.*, 276(20): 17395-17404 (2001).
Hall, *Methods Mol. Biol.*, 166: 139-154 (2001).
Haneda et al., *Carbohydr. Res.*, 292: 61-70 (1996).
Hang et al., *J. Am. Chem. Soc.*, 123(6): 1242-1243 (2001).
Hansen et al., *Biochem J.*, 308: 801-813 (1995).
Haro et al., *Biochem. Biophys. Res. Comm.*, 228(2): 549-556 (1996).
Harris et al., *Nat. Rev. Drug Discov.*, 2(3): 214-221 (2003).
Harris et al., Abstracts of Papers of the American Chemical Society, V 201, APR, P 64-POLY, pp. 154-155 (1991).
Harris, *J. Macromol. Science, Rev. Macromol. Chem. Phys.*, C25(3): 325-373 (1985).
Harris (ed.), "Poly(Ethylene Glycol) Chemistry: Biotechnical and Biomedical Applications", Plenum Press, New York (1992) (Title Pages only).
Harris et al. (eds.), "Poly(ethylene glycol): Chemistry and Biological Applications," ACS Symposium Series, vol. 680, American Chemical Society (1997) (Title Pages only).
Hassan et al., *J. Biol. Chem.*, 275(49): 38197-38205 (2000).
Hassan et al., *Carbohydrates in Chemistry and Biology*, Part II, 3: 273-292 (2000).
Hayes et al., *J. Biol. Chem.*, 268(22): 16170-16178 (1993).
Hellstrom et al., *Methods Mol. Biol.*, 166: 3-16 (2001).
Hermentin, et al., *Glycobiology*, 6(2): 217-230 (1996).
Herscovics et al., *FASEB J.*, 7(6): 540-550 (1993).
Hills et al., *Am. Biotechnol. Lab.*, 20(11): 30 (2002).
Hink et al., *Biotechnol. Prog.*, 7(1): 9-14 (1991).
Höglund, *Med. Oncol.*, 15(4): 229-233 (1998).
Hollister et al., *Glycobiology*, 11(1): 1-9 (2001).
Hounsell et al., *Glycoconj. J.*, 13(1): 19-26 (1996).
Ichikawa et al., *J. Am. Chem. Soc.*, 114(24): 9283-9298 (1992).
Ikonomou et al., *In Vitro Cell. Dev. Biol. Anim.*, 37(9): 549-559 (2001).
Inlow et al., *J. Tissue Cult. Methods*, 12(1): 13-16 (1989).
Inoue et al., *Biotechnol. Annu. Rev.*, 1: 297-313 (1995).
Ito et al., *Pure Appl. Chem.*, 65(4): 753-762 (1993).
Jackson et al., *Anal. Biochem.*, 165(1): 114-127 (1987).
Jarvis et al., *Curr. Opin. Biotechnol.*, 9(5): 528-533 (1998).
Jezek et al., *J. Peptide Sci.*, 5: 46-55 (1999).
Joppich et al., *Makromol. Chem.*, 180: 1381-1384 (1979).
Joshi et al., *J. Biol. Chem.*, 265(24): 14518-14525 (1990).
Jung et al., *Biochim. Biophys. Acta*, 761(2): 152-162 (1983).
Kajihara et al., *Carbohydrate Research*, 315: 137-141 (1999).
Kalsner et al., *Glycoconj. J.*, 12(3): 360-370 (1995).
Kaneko et al., *Cytogenet. Cell Genet.*, 86(3-4): 329-330 (1999).
Kaneko et al., *FEBS Lett.*, 452(3): 237-242 (1999).
Kasina et al., *Bioconjug. Chem.*, 9(1): 108-117 (1998).
Katre et al., *Proc. Natl. Acad. Sci. USA*, 84(6): 1487-1491 (1987).
Kawasaki et al., *Anal. Biochem.*, 285: 82-91 (2000).
Keana et al., *J. Org. Chem.*, 55(11): 3640-3647 (1990).
Keene et al., *J. Biol. Chem.*, 264(9): 4769-4775 (1989).
Keppler et al., *Glycobiology*, 11(2): 11R-18R (2001).
Kimura et al., *Proc. Natl. Acad. Sci. USA*, 96(8): 4530-4535 (1999).
Kisselev, *Structure*, 10(1): 8-9 (2002).
Kitamura et al., *Biochem. Biophys. Res. Commun.*, 171(3): 1387-1394 (1990).
Kitamura et al., *Cancer Res.*, 51(16): 4310-4315 (1991).
Kobayashi et al., *Eur. J. Nucl. Med.*, 27(9):1334-1339 (2000).
Kodama et al., *Tetrahedron Lett.*, 34(40): 6419-6422 (1993).
Koeller et al., *Nat. Biotechnol.*, 18(8): 835-841 (2000).
Koeller et al., *Nature*, 409(6817): 232-240 (2001).
Koide et al., *Biochem. Biophys. Res. Commun.*, 111(2): 659-667 (1983).
Kornfeld et al., *Ann. Rev. Biochem.*, 54: 631-664 (1985).
Kreitman, *Curr Pharm Biotechnol.*, 2(4): 313-325 (2001).
Kuhn et al., *J. Biol. Chem.*, 270(49): 29493-29497 (1995).
Kukowska-Latallo et al., *Genes Dev.*, 4(8): 1288-1303 (1990).
Kukuruzinska et al., *Proc. Natl. Acad. Sci. USA*, 84(8): 2145-2149 (1987).
Lai et al, *J. Biol. Chem.*, 261(7): 3116-3121 (1986).
Langer, *Science*, 249(4976): 1527-1533 (1990).
Lau et al., *J. Biotechnol.*, 75(2-3): 105-115 (1999).
Lee et al., *Biochemistry*, 28(4): 1856-1861 (1989).
Lee-Huang et al., *Proc. Natl. Acad. Sci. USA*, 81(9): 2708-2712 (1984).
Legault et al., *J. Biol. Chem.*, 270(36): 20987-20996 (1995).
Leist et al., *Science*, 305: 239-242 (2004).
Leiter et al., *J. Biol. Chem.*, 274(31): 21830-21839 (1999).
Leung, *J Immunol.* 154(11 ): 5919-5926 (1995).
Lewis et al., *Endocr. J.*, 47(Suppl.): S1-S8 (2000).
Li et al., *Trends Pharmacol. Sci.*, 23(5): 206-209 (2002).
Li et al., *Med. Res. Rev.*, 22(3): 225-250 (2002).
Licari et al., *Biotechnol. Bioeng.*, 39(4): 432-441 (1992).
Licari et al., *Biotechnol. Bioeng.*, 39(9): 932-944 (1992).
Lin et al., *Proc. Natl. Acad. Sci. USA*, 82: 7580-7584 (1985).
Liu et al., *Chem. Eur. J.*, 2(11): 1359-1362 (1996).
Long et al., *Exp. Hematol.*, 34(6): 697-704 (2006).
Lönnberg, *Curr. Org. Synth.*, 6(4): 400-425 (2009).
Lord et al., *Clin. Cancer Res.*, 7(7): 2085-2090 (2001).
Lougheed et al., *J. Biol. Chem.*, 274(53): 37717-37722 (1999).
Luckow et al., *Curr. Opin. Biotechnol.*, 4(5): 564-572 (1993).
Lund et al., *FASEB J.*, 9(1): 115-119 (1995).
Lund et al., *J. Immunol.*, 157(11): 4963-4969 (1996).
Mahal et al., *Science*, 276(5315): 1125-1128 (1997).
Malissard et al., *Biochem. Biophys. Res. Commun.*, 267(1): 169-173 (2000).
Maranga et al., *Biotechnol. Bioeng.*, 84(2): 245-253 (2003).
Maras et al., *J Biotechnol.*, 77(2-3): 255-263 (2000).
Meynial-Salles et al., *J. Biotechnol.*, 46(1): 1-14 (1996).
Miller, *Curr. Opin. Genet. Dev.*, 3(1): 97-101 (1993).
Min et al., *Endocr. J.*, 43(5): 585-593 (1996).
Mistry et al., *Lancet*, 348(9041): 1555-1559 (1996).
Mollicone et al., *Eur. J. Biochem.*, 191(1): 169-176 (1990).
Monaco et al., *Gene*, 180: 145-150 (1996).
Morimoto et al., *Glycoconj. J.*, 13(6): 1013-1020 (1996).
Müller et al., *J. Biol. Chem.*, 272(40): 24780-24793 (1997).
Müller et al., *J. Biol. Chem.*, 274(26): 18165-18172 (1999).
Nagata et al., *EMBO J.*, 5(3): 575-581 (1986).
Ngo et al., "The Protein Folding Problem and Tertiary Structure Prediction, Chapter 14: Computational Complexity Protein Structure Prediction, and the Levinthal Paradox," pp. 433-440 and 492-495 (1994).
Nilsson et al., *Methods Enzymol.*, 104: 56-69 (1984).
Nunez et al., *Can. J. Chem.*, 59(14): 2086-2095 (1981).
O'Connell et al., *J. Biol. Chem.*, 267(35): 25010-25018 (1992).
Oetke et al., *J. Biol. Chem.*, 277(8): 6688-6695 (2002).
Oh-Eda et al., *J. Biol. Chem.*, 265: 11432-11435 (1990).
Olson et al., *J. Biol. Chem.*, 274(42): 29889-29896 (1999).
Orlean, "vol. III: The Molecular and Cellular Biology of the Yeast *Saccharomyces*: Cell Cycle and Cell Biology", in *Biogenesis of Yeast Wall and Surface Components*, Chapter 3, pp. 229-362, Cold Spring Harbor Laboratory Press (1997).
Palacpac et al., *Proc. Natl. Acad. Sci. USA*, 96(8): 4692-4697 (1999).
Palcic et al., *Carbohydr. Res.*, 190(1): 1-11 (1989).
Park et al., *J. Biol. Chem.*, 261(1): 205-210 (1986).
Paulson et al., *J. Biol. Chem.*, 252(23): 8624-8628 (1977).
Plummer et al., *J. Biol. Chem.*, 270(22): 13192-13196 (1995).
Prati et al., *Biotech and Bioeng.*, 79(5): 580-585 (2002).
Prieels et al., *J. Biol. Chem.*, 256(20): 10456-10463 (1981).

(56) References Cited

OTHER PUBLICATIONS

Pyatak et al., *Res. Commun. Chem. Pathol. Pharmacol.*, 29(1): 113-127 (1980).
Rabouille et al., *J Cell Sci.*, 112(Pt. 19): 3319-3330 (1999).
Rasko et al., *J. Biol. Chem.*, 275(7): 4988-4994 (2000).
Reff et al., *Cancer Control*, 9(2): 152-166 (2002).
Rosenthal et al., *Methods Enzymol.*, 235: 253-285 (1994).
Rotondaro et al., *Mol. Biotech.*, 11: 117-128 (1999).
Rudikoff et al., *Proc. Natl. Acad. Sci. USA*, 79(6):1979-1983 (1982).
Sadler et al., *Methods Enzymol.*, 83: 458-514 (1982).
Sandberg et al., *Semin. Hematol.*, 38(2 Suppl. 4): 4-12 (2001).
Saneyoshi et al., *Biol. Reprod.*, 65(6): 1686-1690 (2001).
Sasaki et al., *J. Biol. Chem.*, 262(25): 12059-12076 (1987).
Sasaki et al., *J.Biol. Chem.*, 269(20): 14730-14737 (1994).
Saxon et al., *Science*, 287(5460): 2007-2010 (2000).
Schlaeger, *Cytotechnology*, 20(1-3): 57-70 (1996).
Schwientek et al., *Gene*, 145(2): 299-303 (1994).
Schwientek et al., *J. Biol. Chem.*, 277(25): 22623-22638 (2002).
Scouten, *Methods Enzymol.*, 135: 30-65 (1987).
Seely et al., *J. Chromatog.*, 908: 235-241 (2001).
Seffernick et al., *J. Bacteriol.*, 183(8): 2405-2410 (2001).
Seitz, *Chembiochem.*, 1(4): 214-246 (2000).
Shah et al., *J. Pharm. Sci.*, 85(12): 1306-1311 (1996).
Shapiro et al., *Blood*, 105(2): 518-525 (2005).
Shen et al., *Biochem. Biophys. Res. Commun.*, 102(3): 1048-1054 (1981).
Shinkai et al., *Prot. Exp. Purif.*, 10: 379-385 (1997).
Sinclair et al., *J. Pharm. Sci.*, 94: 1626-1635 (2005).
Singh et al., *Chem. Commun.*, 1996(8): 993-994 (1996).
Sinha et al., *Infect. Immun.*, 29(3): 914-925 (1980).
Skolnick et al., *Trends Biotechnol.*, 18(1): 34-39 (2000).
Smith et al., *Nat. Biotechnol.*, 15(12): 1222-1223 (1997).
Snider et al., *J. Chromatogr., A* 599(1-2): 141-155 (1992).
Sojar et al., *Arch. Biochem. Biophys.*, 259(1): 52-57 (1987).
Song et al., *J. Pharmacol. Exp. Ther.*, 301(2): 605-610 (2002).
Srinivasachar et al., *Biochemistry*, 28(6): 2501-2509 (1989).
Staudacher, *Trends Glycosci. Glycotechnol.*, 8(44): 391-408 (1996).
Stemmer, *Nature*, 370(6488): 389-391 (1994).
Stemmer, *Proc. Natl. Acad. Sci. USA*, 91(22): 10747-10751 (1994).
Stephens et al., *Eur. J. Biochem.*, 133(1): 155-162 (1983).
Stephens et al., *Eur. J. Biochem.*, 133(3): 481-489 (1983).
Stephens et al., *Eur. J. Biochem.*, 135(3): 519-527 (1983).
Strausberg et al., *Proc Natl Acad Sci USA*, 99(26): 16899-16903 (2002).
Takane et al., *J Pharmacol Exp Ther.*, 294(2): 746-752 (2000).
Takeda et al., *Trends Biochem. Sci.*, 20(9): 367-371 (1995).
Takeuchi et al., *J. Biol. Chem.*, 265(21): 12127-12130 (1990).
Taniguchi et al., *Proteomics*, 1(2): 239-247 (2001).
Tanner et al., *Biochim. Biophys. Acta*, 906(1): 81-99. (1987).
Taylor et al., Protein Immobilization Fundamentals and Applications, Manual (1991).
Tenno et al., *J. Biol. Chem.*, 277(49): 47088-47096 (2002).
Thotakura et al., *Meth. Enzym.*, 138: 350-9 (1987).
Trottein et al., *Mol. Biochem. Parasitol.*, 107(2): 279-287 (2000).
Tsuboi et al., *Arch. Biochem. Biophys.*, 374(1): 100-106 (2000).
Tsunoda et al., *J. Pharmacol. Exp. Ther.*, 209(1): 368-372 (1999).
Tuddenham, *Nature*, 419(6902): 23-24 (2002).
Udenfriend et al., *Annu. Rev. Biochem.*, 64: 563-591 (1995).
Ulloa-Aguirre et al., *Endocrine*, 11(3): 205-215 (1999).
Uludag et al., *Biotechnol. Prog.*, 18(3): 604-611 (2002).
Urdal et al, *J. Chromatogr.*, 296: 171-179 (1984).
Van Berkel et al., *Biochem. J.*, 319(Pt. 1): 117-122 (1996).
Van Tetering et al., *FEBS Lett.*, 461(3): 311-314 (1999).
Veronese et al., *Appl. Biochem. Biotechnol.*, 11(2): 141-152 (1985).
Vitetta et al., *Science*, 313: 308-309 (2006).
Vocadlo et al., "Glycosidase-Catalysed Oligosaccharide Synthesis" in *Carbohydrate Chemistry and Biology*, vol. 2, Chapter 29, pp. 723-844 (2000).
Vyas et al., *Crit. Rev. Ther. Drug Carrier Syst.*, 18(1): 1-76 (2001).
Wang et al., *Glycobiology*, 6(8): 837-842 (1996).
Wang et al., *Tetrahedron Lett.*, 37(12): 1975-1978 (1996).
Wang et al., *Protein Eng.*, 11(12): 1277-1283 (1998).
Wang et al., *Microbiol.*, 145(Pt. 11): 3245-3253 (1999).
Wellhoner et al., *J. Biol. Chem.*, 266(7): 4309-4314 (1991).
Wells, *Biochemistry*, 29(37): 8509-8517 (1990).
Weston et al., *J. Biol. Chem.*, 267(34): 24575-24584 (1992).
White et al., *J. Biol. Chem.*, 270(41): 24156-24165 (1995).
Wishart et al., *J. Biol. Chem.*, 270(45): 26782-26785 (1995).
Witkowski et al., *Biochemistry*, 38(36): 11643-11650 (1999).
Witte et al., *J. Am. Chem. Soc.*, 119(9): 2114-2118 (1997).
Witte et al., *Cancer and Metastasis Rev.*, 17: 155-161 (1998).
Woghiren et al., *Bioconjug. Chem.*, 4(5): 314-318 (1993).
Wong et al., *Enzyme Microb Technol.*, 14(11): 866-874 (1992).
Wong et al., *Biotechnol. Bioeng.*, 49(6): 659-666 (1996).
Woods et al., *Eur. J. Cell Biol.*, 50(1): 132-143 (1989).
Wright et al., *J. Immunol.*, 160(7): 3393-3402 (1998).
Wu et al., *J. Drug Target.*, 10(3): 239-245 (2002).
Xing et al., *Biochem. J.*, 336(Pt. 3): 667-673 (1998).
Yamada et al., *Biochemistry*, 20(17): 4836-4842 (1981).
Yamamoto et al., *Carbohydr. Res.*, 305(3-4): 415-422 (1998).
Yarema et al., *J. Biol. Chem.*, 273(47): 31168-31179 (1998).
Yoshida et al., *Glycobiology*, 9(1): 53-58 (1999).
Yoshitake et al., *Biochemistry*, 24(14): 3736-3750 (1985).
Younes et al., *J. Biomed. Mater. Res.*, 21(11): 1301-1316 (1987).
Zalipsky et al., "Use of Functionalized Poly(Ethylene Glycol)s for Modification of Polypeptides" in *Poly(Ethylene Glycol) Chemistry: Biotechnical and Biomedical Applications*, Harris (ed.), Chapter 21, pp. 347-370 (Plenum Press, New York, 1992).
Zalipsky, *Bioconjug. Chem.*, 6(2): 150-165 (1995).
Zarling et al., *J. Immunol.*, 124(2): 913-920 (1980).
Zheng et al., *Biotechnol. Bioeng.*, 65(5): 600-604 (1999).
Zhou et al., 1994, *Mol. Microbiol.*, 14(4): 609-618 (1994).
Office Action dated Nov. 24, 2010 in U.S. Appl. No. 11/866,969.
Office Action dated Nov. 26, 2010 in U.S. Appl. No. 11/981,483.
Office Action dated Dec. 16, 2010 in U.S. Appl. No. 10/579,620.
Office Action dated Dec. 16, 2010 in U.S. Appl. No. 11/701,949.
Office Action dated Dec. 17, 2010 in U.S. Appl. No. 11/658,218.
Office Action dated Dec. 21, 2010 in U.S. Appl. No. 11/632,005.
Office Action dated Dec. 27, 2010 in U.S. Appl. No. 11/144,223.
Office Action dated Jan. 10, 2011 in U.S. Appl. No. 11/659,942.
Office Action dated Jan. 18, 2011 in U.S. Appl. No. 12/444,380.
Office Action dated Jan. 20, 2011 in U.S. Appl. No. 10/586,166.
Office Action dated Jan. 21, 2011 in U.S. Appl. No. 11/843,588.
Office Action dated Feb. 1, 2011 in U.S. Appl. No. 11/867,553.
Office Action dated Feb. 3, 2011 in U.S. Appl. No. 11/794,555.
Office Action dated Feb. 3, 2011 in U.S. Appl. No. 11/914,104.
Office Action dated Feb. 3, 2011 in U.S. Appl. No. 12/443,428.
Office Action dated Feb. 4, 2011 in U.S. Appl. No. 11/794,560.
Office Action dated Feb. 15, 2011 in U.S. Appl. No. 12/496,595.
Office Action dated Feb. 22, 2011 in U.S. Appl. No. 12/820,926.
Office Action dated Feb. 23, 2011 in U.S. Appl. No. 12/092,563.
Office Action dated Mar. 2, 2011 in U.S. Appl. No. 12/201,705.
Office Action dated Mar. 11, 2011 in U.S. Appl. No. 11/982,273.
Office Action dated Mar. 16, 2011 in U.S. Appl. No. 11/665,908.
Office Action dated Mar. 17, 2011 in U.S. Appl. No. 11/597,258.
Office Action dated May 31, 2011 in U.S. Appl. No. 11/144,223.
Office Action dated Jun. 9, 2011 in U.S. Appl. No. 11/597,258.
Office Action dated Jul. 8, 2011 in U.S. Appl. No. 11/632,005.
Office Action dated Jul. 21, 2011 in U.S. Appl. No. 11/665,908.
Office Action dated Aug. 17, 2011 in U.S. Appl. No. 11/632,005.
Office Action dated Aug. 22, 2011 in U.S. Appl. No. 11/659,942.
Office Action dated Sep. 22, 2011 in U.S. Appl. No. 12/820,926.
Office Action dated Oct. 6, 2011 in U.S. Appl. No. 12/663,748.
Office Action dated Nov. 2, 2011 in U.S. Appl. No. 12/201,705.
Office Action dated Nov. 17, 2011 in U.S. Appl. No. 12/443,428.
Office Action dated Dec. 1, 2011 in U.S. Appl. No. 11/794,560.
Office Action dated Dec. 22, 2011 in U.S. Appl. No. 12/858,247.
Office Action dated Jan. 3, 2012 in U.S. Appl. No. 11/632,005.
Office Action dated Feb. 29, 2012 in U.S. Appl. No. 12/858,247.
Office Action dated Mar. 21, 2012 in U.S. Appl. No. 11/794,560.
Office Action dated Mar. 29, 2012 in U.S. Appl. No. 12/594,326.
Office Action dated Apr. 18, 2012 in U.S. Appl. No. 12/663,748.
Office Action dated Apr. 19, 2012 in U.S. Appl. No. 13/215,439.

(56) References Cited

OTHER PUBLICATIONS

Office Action dated Aug. 8, 2012 in U.S. Appl. No. 13/157,575.
Office Action dated Aug. 17, 2012 in U.S. Appl. No. 12/594,326.
Office Action dated Sep. 20, 1994 in U.S. Appl. No. 08/215,727.
Office Action dated May 4, 1995 in U.S. Appl. No. 08/102,385.
Office Action dated Jun. 7, 1995 in U.S. Appl. No. 08/215,727.
Office Action dated Apr. 5, 1996 in U.S. Appl. No. 08/102,385.
Office Action dated Jun. 23, 1996 in U.S. Appl. No. 08/447,435.
Office Action dated Jun. 28, 1996 in U.S. Appl. No. 08/447,783.
Office Action dated Aug. 28, 1996 in U.S. Appl. No. 08/478,140.
Office Action dated Oct. 15, 1996 in U.S. Appl. No. 08/102,385.
Office Action dated Feb. 24, 1997 in U.S. Appl. No. 08/447,435.
Office Action dated Feb. 24, 1997 in U.S. Appl. No. 08/447,783.
Office Action dated Apr. 12, 1997 in U.S. Appl. No. 08/215,727.
Office Action dated Jul. 23, 1997 in U.S. Appl. No. 08/102,385.
Office Action dated Aug. 8, 1997 in U.S. Appl. No. 08/745,840.
Office Action dated Oct. 9, 1997 in U.S. Appl. No. 08/478,140.
Office Action dated Dec. 1, 1997 in U.S. Appl. No. 08/446,875.
Office Action dated Jan. 2, 1998 in U.S. Appl. No. 08/878,360.
Office Action dated Mar. 30, 1998 in U.S. Appl. No. 08/745,840.
Office Action dated Jun. 19, 1998 in U.S. Appl. No. 08/478,140.
Office Action dated Oct. 29, 1998 in U.S. Appl. No. 08/745,840.
Office Action dated Feb. 4, 1999 in U.S. Appl. No. 08/478,140.
Office Action dated Apr. 1, 1999 in U.S. Appl. No. 08/745,840.
Office Action dated Oct. 23, 1999 in U.S. Appl. No. 08/102,385.
Office Action dated Oct. 4, 2000 in U.S. Appl. No. 09/333,412.
Office Action dated Jan. 30, 2001 in U.S. Appl. No. 09/338,943.
Office Action dated Jun. 4, 2002 in U.S. Appl. No. 09/855,320.
Office Action dated Sep. 27, 2002 in U.S. Appl. No. 09/855,320.
Office Action dated Dec. 9, 2002 in U.S. Appl. No. 10/007,267.
Office Action dated Jun. 2, 2003 in U.S. Appl. No. 10/007,267.
Office Action dated Aug. 26, 2003 in U.S. Appl. No. 10/109,498.
Office Action dated Nov. 5, 2003 in U.S. Appl. No. 10/007,267.
Office Action dated Nov. 17, 2003 in U.S. Appl. No. 09/855,320.
Office Action dated Dec. 16, 2003 in U.S. Appl. No. 10/109,498.
Office Action dated Jun. 9, 2004 in U.S. Appl. No. 09/855,320.
Office Action dated Oct. 20, 2004 in U.S. Appl. No. 10/198,806.
Office Action dated Nov. 12, 2004 in U.S. Appl. No. 10/219,197.
Office Action dated Jan. 12, 2005 in U.S. Appl. No. 10/198,806.
Office Action dated Mar. 4, 2005 in U.S. Appl. No. 10/410,945.
Office Action dated Mar. 7, 2005 in U.S. Appl. No. 10/287,994.
Office Action dated Mar. 14, 2005 in U.S. Appl. No. 09/855,320.
Office Action dated Jun. 2, 2005 in U.S. Appl. No. 10/654,528.
Office Action dated Jun. 9, 2005 in U.S. Appl. No. 10/109,498.
Office Action dated Jun. 29, 2005 in U.S. Appl. No. 10/287,994.
Office Action dated Jul. 21, 2005 in U.S. Appl. No. 10/198,806.
Office Action dated Aug. 10, 2005 in U.S. Appl. No. 10/410,945.
Office Action dated Sep. 21, 2005 in U.S. Appl. No. 10/391,035.
Office Action dated Sep. 28, 2005 in U.S. Appl. No. 10/410,897.
Office Action dated Sep. 28, 2005 in U.S. Appl. No. 10/410,913.
Office Action dated Sep. 28, 2005 in U.S. Appl. No. 10/410,930.
Office Action dated Sep. 28, 2005 in U.S. Appl. No. 10/410,962.
Office Action dated Sep. 28, 2005 in U.S. Appl. No. 10/410,980.
Office Action dated Sep. 28, 2005 in U.S. Appl. No. 10/410,997.
Office Action dated Sep. 28, 2005 in U.S. Appl. No. 10/411,012.
Office Action dated Sep. 28, 2005 in U.S. Appl. No. 10/411,037.
Office Action dated Sep. 28, 2005 in U.S. Appl. No. 10/411,043.
Office Action dated Sep. 28, 2005 in U.S. Appl. No. 10/411,044.
Office Action dated Sep. 28, 2005 in U.S. Appl. No. 10/411,049.
Office Action dated Oct. 6, 2005 in U.S. Appl. No. 10/411,026.
Office Action dated Oct. 19, 2005 in U.S. Appl. No. 10/997,405.
Office Action dated Nov. 14, 2005 in U.S. Appl. No. 10/410,897.
Office Action dated Nov. 14, 2005 in U.S. Appl. No. 10/410,997.
Office Action dated Nov. 15, 2005 in U.S. Appl. No. 10/287,994.
Office Action dated Nov. 30, 2005 in U.S. Appl. No. 10/654,528.
Office Action dated Dec. 7, 2005 in U.S. Appl. No. 10/609,701.
Office Action dated Dec. 8, 2005 in U.S. Appl. No. 10/391,035.
Office Action dated Dec. 13, 2005 in U.S. Appl. No. 11/033,365.
Office Action dated Dec. 29, 2005 in U.S. Appl. No. 09/855,320.
Office Action dated Jan. 24, 2006 in U.S. Appl. No. 10/410,930.
Office Action dated Jan. 26, 2006 in U.S. Appl. No. 10/410,913.
Office Action dated Jan. 26, 2006 in U.S. Appl. No. 10/411,012.
Office Action dated Jan. 27, 2006 in U.S. Appl. No. 10/410,945.
Office Action dated Jan. 31, 2006 in U.S. Appl. No. 10/410,962.
Office Action dated Feb. 7, 2006 in U.S. Appl. No. 10/410,980.
Office Action dated Feb. 7, 2006 in U.S. Appl. No. 10/411,043.
Office Action dated Feb. 7, 2006 in U.S. Appl. No. 10/997,405.
Office Action dated Mar. 3, 2006 in U.S. Appl. No. 10/391,035.
Office Action dated Mar. 15, 2006 in U.S. Appl. No. 10/198,806.
Office Action dated Mar. 22, 2006 in U.S. Appl. No. 10/411,049.
Office Action dated Apr. 4, 2006 in U.S. Appl. No. 10/410,897.
Office Action dated Apr. 4, 2006 in U.S. Appl. No. 10/410,997.
Office Action dated Apr. 4, 2006 in U.S. Appl. No. 10/411,026.
Office Action dated Apr. 6, 2006 in U.S. Appl. No. 11/102,497.
Office Action dated May 2, 2006 in U.S. Appl. No. 11/144,223.
Office Action dated Jul. 28, 2006 in U.S. Appl. No. 10/109,498.
Office Action dated Aug. 24, 2006 in U.S. Appl. No. 10/492,261.
Office Action dated Aug. 30, 2006 in U.S. Appl. No. 11/102,497.
Office Action dated Oct. 6, 2006 in U.S. Appl. No. 10/497,284.
Office Action dated Oct. 17, 2006 in U.S. Appl. No. 11/339,752.
Office Action dated Nov. 1, 2006 in U.S. Appl. No. 11/183,205.
Office Action dated Nov. 1, 2006 in U.S. Appl. No. 11/183,218.
Office Action dated Nov. 15, 2006 in U.S. Appl. No. 10/411,026.
Office Action dated Nov. 28, 2006 in U.S. Appl. No. 11/144,223.
Office Action dated Dec. 8, 2006 in U.S. Appl. No. 10/997,405.
Office Action dated Dec. 13, 2006 in U.S. Appl. No. 10/410,980.
Office Action dated Dec. 13, 2006 in U.S. Appl. No. 10/411,043.
Office Action dated Dec. 13, 2006 in U.S. Appl. No. 10/497,284.
Office Action dated Dec. 18, 2006 in U.S. Appl. No. 09/855,320.
Office Action dated Dec. 21, 2006 in U.S. Appl. No. 11/183,205.
Office Action dated Dec. 21, 2006 in U.S. Appl. No. 11/183,218.
Office Action dated Dec. 29, 2006 in U.S. Appl. No. 11/033,365.
Office Action dated Jan. 22, 2007 in U.S. Appl. No. 10/198,806.
Office Action dated Jan. 24, 2007 in U.S. Appl. No. 11/404,266.
Office Action dated Jan. 31, 2007 in U.S. Appl. No. 10/497,283.
Office Action dated Feb. 27, 2007 in U.S. Appl. No. 10/609,701.
Office Action dated Feb. 28, 2007 in U.S. Appl. No. 10/492,261.
Office Action dated Apr. 5, 2007 in U.S. Appl. No. 10/485,892.
Office Action dated Apr. 6, 2007 in U.S. Appl. No. 11/339,752.
Office Action dated Apr. 12, 2007 in U.S. Appl. No. 10/497,283.
Office Action dated Apr. 16, 2007 in U.S. Appl. No. 10/410,980.
Office Action dated Apr. 26, 2007 in U.S. Appl. No. 11/033,365.
Office Action dated Apr. 27, 2007 in U.S. Appl. No. 11/183,205.
Office Action dated Apr. 30, 2007 in U.S. Appl. No. 11/183,218.
Office Action dated May 15, 2007 in U.S. Appl. No. 11/144,223.
Office Action dated May 31, 2007 in U.S. Appl. No. 11/395,784.
Office Action dated Jun. 1, 2007 in U.S. Appl. No. 11/102,497.
Office Action dated Jun. 11, 2007 in U.S. Appl. No. 11/514,484.
Office Action dated Jun. 25, 2007 in U.S. Appl. No. 10/411,043.
Office Action dated Jun. 26, 2007 in U.S. Appl. No. 10/411,026.
Office Action dated Jul. 13, 2007 in U.S. Appl. No. 11/440,839.
Office Action dated Jul. 26, 2007 in U.S. Appl. No. 11/395,784.
Office Action dated Aug. 16, 2007 in U.S. Appl. No. 10/497,283.
Office Action dated Aug. 17, 2007 in U.S. Appl. No. 10/492,261.
Office Action dated Aug. 30, 2007 in U.S. Appl. No. 10/497,284.
Office Action dated Sep. 4, 2007 in U.S. Appl. No. 11/144,223.
Office Action dated Sep. 18, 2007 in U.S. Appl. No. 09/855,320.
Office Action dated Oct. 1, 2007 in U.S. Appl. No. 10/411,043.
Office Action dated Oct. 2, 2007 in U.S. Appl. No. 11/166,028.
Office Action dated Oct. 3, 2007 in U.S. Appl. No. 11/514,484.
Office Action dated Oct. 16, 2007 in U.S. Appl. No. 11/183,205.
Office Action dated Oct. 16, 2007 in U.S. Appl. No. 11/183,218.
Office Action dated Oct. 30, 2007 in U.S. Appl. No. 11/580,669.
Office Action dated Nov. 1, 2007 in U.S. Appl. No. 11/339,752.
Office Action dated Nov. 15, 2007 in U.S. Appl. No. 11/166,404.
Office Action dated Nov. 28, 2007 in U.S. Appl. No. 11/102,497.
Office Action dated Dec. 7, 2007 in U.S. Appl. No. 10/530,972.
Office Action dated Dec. 11, 2007 in U.S. Appl. No. 11/440,839.
Office Action dated Dec. 17, 2007 in U.S. Appl. No. 10/497,284.
Office Action dated Dec. 27, 2007 in U.S. Appl. No. 11/396,215.
Office Action dated Dec. 28, 2007 in U.S. Appl. No. 11/402,105.
Office Action dated Dec. 28, 2007 in U.S. Appl. No. 10/565,331.
Office Action dated Jan. 3, 2008 in U.S. Appl. No. 10/549,528.

(56) References Cited

OTHER PUBLICATIONS

Office Action dated Jan. 9, 2008 in U.S. Appl. No. 11/144,223.
Office Action dated Jan. 11, 2008 in U.S. Appl. No. 10/485,892.
Office Action dated Jan. 30, 2008 in U.S. Appl. No. 10/411,043.
Office Action dated Feb. 6, 2008 in U.S. Appl. No. 11/395,784.
Office Action dated Mar. 3, 2008 in U.S. Appl. No. 11/166,404.
Office Action dated Mar. 4, 2008 in U.S. Appl. No. 09/855,320.
Office Action dated Mar. 7, 2008 in U.S. Appl. No. 11/580,669.
Office Action dated Mar. 10, 2008 in U.S. Appl. No. 10/497,284.
Office Action dated Mar. 13, 2008 in U.S. Appl. No. 10/411,026.
Office Action dated Mar. 20, 2008 in U.S. Appl. No. 10/411,044.
Office Action dated Mar. 31, 2008 in U.S. Appl. No. 10/549,528.
Office Action dated Apr. 3, 2008 in U.S. Appl. No. 11/166,028.
Office Action dated Apr. 7, 2008 in U.S. Appl. No. 11/344,767.
Office Action dated Apr. 28, 2008 in U.S. Appl. No. 11/402,105.
Office Action dated Apr. 29, 2008 in U.S. Appl. No. 10/565,331.
Office Action dated May 12, 2008 in U.S. Appl. No. 10/485,892.
Office Action dated Jun. 9, 2008 in U.S. Appl. No. 09/855,320.
Office Action dated Jun. 30, 2008 in U.S. Appl. No. 11/396,215.
Office Action dated Jul. 10, 2008 in U.S. Appl. No. 11/514,484.
Office Action dated Jul. 22, 2008 in U.S. Appl. No. 11/102,497.
Office Action dated Jul. 24, 2008 in U.S. Appl. No. 11/344,767.
Office Action dated Aug. 15, 2008 in U.S. Appl. No. 11/845,175.
Office Action dated Aug. 21, 2008 in U.S. Appl. No. 10/411,044.
Office Action dated Aug. 26, 2008 in U.S. Appl. No. 11/580,669.
Office Action dated Sep. 16, 2008 in U.S. Appl. No. 11/440,839.
Office Action dated Sep. 22, 2008 in U.S. Appl. No. 10/556,094.
Office Action dated Oct. 21, 2008 in U.S. Appl. No. 10/530,972.
Office Action dated Oct. 30, 2008 in U.S. Appl. No. 10/411,026.
Office Action dated Oct. 31, 2008 in U.S. Appl. No. 11/166,404.
Office Action dated Nov. 12, 2008 in U.S. Appl. No. 11/144,223.
Office Action dated Nov. 18, 2008 in U.S. Appl. No. 10/497,284.
Office Action dated Dec. 24, 2008 in U.S. Appl. No. 11/396,215.
Office Action dated Jan. 6, 2009 in U.S. Appl. No. 10/549,528.
Office Action dated Jan. 21, 2009 in U.S. Appl. No. 10/565,331.
Office Action dated Feb. 9, 2009 in U.S. Appl. No. 09/855,320.
Office Action dated Feb. 10, 2009 in U.S. Appl. No. 11/166,404.
Office Action dated Mar. 4, 2009 in U.S. Appl. No. 11/580,669.
Office Action dated Mar. 12, 2009 in U.S. Appl. No. 11/102,497.
Office Action dated Mar. 12, 2009 in U.S. Appl. No. 11/514,484.
Office Action dated Mar. 17, 2009 in U.S. Appl. No. 10/411,026.
Office Action dated Apr. 1, 2009 in U.S. Appl. No. 10/552,896.
Office Action dated Apr. 16, 2009 in U.S. Appl. No. 10/576,506.
Office Action dated May 11, 2009 in U.S. Appl. No. 10/411,044.
Office Action dated May 14, 2009 in U.S. Appl. No. 11/910,958.
Office Action dated May 22, 2009 in U.S. Appl. No. 11/166,404.
Office Action dated Jun. 1, 2009 in U.S. Appl. No. 12/201,705.
Office Action dated Jun. 3, 2009 in U.S. Appl. No. 10/549,520.
Office Action dated Jun. 17, 2009 in U.S. Appl. No. 11/934,700.
Office Action dated Jul. 2, 2009 in U.S. Appl. No. 10/497,284.
Office Action dated Jul. 21, 2009 in U.S. Appl. No. 11/440,839.
Office Action dated Jul. 21, 2009 in U.S. Appl. No. 10/549,528.
Office Action dated Aug. 7, 2009 in U.S. Appl. No. 10/556,094.
Office Action dated Aug. 7, 2009 in U.S. Appl. No. 10/579,621.
Office Action dated Aug. 11, 2009 in U.S. Appl. No. 10/549,445.
Office Action dated Aug. 13, 2009 in U.S. Appl. No. 09/855,320.
Office Action dated Aug. 17, 2009 in U.S. Appl. No. 10/581,538.
Office Action dated Sep. 18, 2009 in U.S. Appl. No. 11/652,467.
Office Action dated Sep. 23, 2009 in U.S. Appl. No. 12/201,705.
Office Action dated Sep. 28, 2009 in U.S. Appl. No. 11/910,958.
Office Action dated Sep. 29, 2009 in U.S. Appl. No. 11/645,839.
Office Action dated Sep. 29, 2009 in U.S. Appl. No. 11/714,874.
Office Action dated Oct. 2, 2009 in U.S. Appl. No. 11/781,900.
Office Action dated Oct. 2, 2009 in U.S. Appl. No. 11/781,902.
Office Action dated Oct. 14, 2009 in U.S. Appl. No. 10/549,528.
Office Action dated Oct. 14, 2009 in U.S. Appl. No. 10/565,331.
Office Action dated Oct. 23, 2009 in U.S. Appl. No. 11/396,215.
Office Action dated Oct. 27, 2009 in U.S. Appl. No. 11/402,105.
Office Action dated Nov. 2, 2009 in U.S. Appl. No. 11/659,942.
Office Action dated Nov. 2, 2009 in U.S. Appl. No. 11/866,969.
Office Action dated Nov. 4, 2009 in U.S. Appl. No. 10/549,445.
Office Action dated Nov. 20, 2009 in U.S. Appl. No. 11/580,669.
Office Action dated Nov. 24, 2009 in U.S. Appl. No. 11/781,888.
Office Action dated Nov. 27, 2009 in U.S. Appl. No. 11/781,885.
Office Action dated Dec. 10, 2009 in U.S. Appl. No. 11/144,223.
Office Action dated Dec. 12, 2009 in U.S. Appl. No. 12/418,530.
Office Action dated Dec. 14, 2009 in U.S. Appl. No. 11/102,497.
Office Action dated Dec. 17, 2009 in U.S. Appl. No. 10/581,538.
Office Action dated Dec. 17, 2009 in U.S. Appl. No. 11/781,896.
Office Action dated Dec. 22, 2009 in U.S. Appl. No. 09/855,320.
Office Action dated Dec. 28, 2009 in U.S. Appl. No. 12/371,156.
Office Action dated Jan. 6, 2010 in U.S. Appl. No. 11/656,643.
Office Action dated Jan. 19, 2010 in U.S. Appl. No. 11/597,258.
Office Action dated Jan. 26, 2010 in U.S. Appl. No. 11/166,404.
Office Action dated Jan. 27, 2010 in U.S. Appl. No. 11/440,839.
Office Action dated Feb. 4, 2010 in U.S. Appl. No. 12/201,705.
Office Action dated Feb. 5, 2010 in U.S. Appl. No. 11/584,743.
Office Action dated Feb. 5, 2010 in U.S. Appl. No. 11/657,441.
Office Action dated Feb. 8, 2010 in U.S. Appl. No. 12/184,956.
Office Action dated Feb. 19, 2010 in U.S. Appl. No. 11/981,483.
Office Action dated Feb. 19, 2010 in U.S. Appl. No. 11/982,273.
Office Action dated Mar. 3, 2010 in U.S. Appl. No. 10/579,620.
Office Action dated Mar. 3, 2010 in U.S. Appl. No. 11/917,772.
Office Action dated Mar. 4, 2010 in U.S. Appl. No. 09/855,320.
Office Action dated Mar. 8, 2010 in U.S. Appl. No. 11/652,467.
Office Action dated Mar. 11, 2010 in U.S. Appl. No. 12/101,389.
Office Action dated Mar. 15, 2010 in U.S. Appl. No. 10/497,284.
Office Action dated Mar. 29, 2010 in U.S. Appl. No. 11/514,484.
Office Action dated Mar. 30, 2010 in U.S. Appl. No. 12/496,595.
Office Action dated Apr. 2, 2010 in U.S. Appl. No. 11/701,949.
Office Action dated Apr. 5, 2010 in U.S. Appl. No. 10/556,094.
Office Action dated Apr. 5, 2010 in U.S. Appl. No. 10/579,621.
Office Action dated May 3, 2010 in U.S. Appl. No. 12/276,885.
Office Action dated May 13, 2010 in U.S. Appl. No. 11/781,888.
Office Action dated May 14, 2010 in U.S. Appl. No. 11/781,885.
Office Action dated May 24, 2010 in U.S. Appl. No. 10/581,538.
Office Action dated May 26, 2010 in U.S. Appl. No. 11/144,223.
Office Action dated May 26, 2010 in U.S. Appl. No. 11/659,942.
Office Action dated May 26, 2010 in U.S. Appl. No. 11/866,969.
Office Action dated May 27, 2010 in U.S. Appl. No. 10/565,331.
Office Action dated Jun. 16, 2010 in U.S. Appl. No. 11/843,588.
Office Action dated Jul. 1, 2010 in U.S. Appl. No. 11/981,483.
Office Action dated Jul. 2, 2010 in U.S. Appl. No. 11/632,005.
Office Action dated Jul. 6, 2010 in U.S. Appl. No. 10/579,620.
Office Action dated Jul. 6, 2010 in U.S. Appl. No. 11/917,772.
Office Action dated Jul. 8, 2010 in U.S. Appl. No. 11/867,553.
Office Action dated Jul. 15, 2010 in U.S. Appl. No. 11/664,199.
Office Action dated Jul. 15, 2010 in U.S. Appl. No. 11/701,949.
Office Action dated Jul. 20, 2010 in U.S. Appl. No. 11/652,467.
Office Action dated Jul. 22, 2010 in U.S. Appl. No. 12/201,705.
Office Action dated Jul. 27, 2010 in U.S. Appl. No. 11/656,643.
Office Action dated Aug. 5, 2010 in U.S. Appl. No. 12/496,595.
Office Action dated Aug. 17, 2010 in U.S. Appl. No. 11/632,005.
Office Action dated Aug. 19, 2010 in U.S. Appl. No. 11/665,908.
Office Action dated Aug. 20, 2010 in U.S. Appl. No. 11/144,223.
Office Action dated Sep. 10, 2010 in U.S. Appl. No. 11/867,553.
Office Action dated Sep. 14, 2010 in U.S. Appl. No. 12/371,156.
Office Action dated Sep. 22, 2010 in U.S. Appl. No. 11/982,273.
Office Action dated Oct. 1, 2010 in U.S. Appl. No. 11/166,404.
Office Action dated Oct. 1, 2010 in U.S. Appl. No. 11/597,258.
Office Action dated Oct. 1, 2010 in U.S. Appl. No. 11/644,014.
Office Action dated Oct. 1, 2010 in U.S. Appl. No. 11/910,958.
Office Action dated Oct. 4, 2010 in U.S. Appl. No. 12/302,167.
Office Action dated Oct. 5, 2010 in U.S. Appl. No. 11/579,401.
Office Action dated Oct. 12, 2010 in U.S. Appl. No. 12/066,619.
Office Action dated Oct. 13, 2010 in U.S. Appl. No. 11/792,610.
Office Action dated Oct. 14, 2010 in U.S. Appl. No. 11/781,885.
Office Action dated Oct. 15, 2010 in U.S. Appl. No. 11/664,199.
Office Action dated Oct. 15, 2010 in U.S. Appl. No. 11/781,888.
Arslan et al., *Transf. Apher. Sci.*, 37: 179-185 (2007).
Bijsterbosch et al., *Eur. J. Biochem.*, 237(2): 344-349 (1996).
Broxmeyer et al., *J. Exp. Med.*, 201(8): 1307-1318 (2005).
Brumeanu et al., *J. Immunol. Meth.*, 183: 185-197 (1995).

(56) References Cited

OTHER PUBLICATIONS

Capoccia et al., *Blood*, 108(7): 2438-2445 (2006).
Cashen et al., *Bone Marrow Trans.*, 39: 577-588 (2007).
Deacon, *Diabetes*, 54: 2181-2189 (2004).
De Vries et al., *Glycobiology*, 7(7): 921-927 (1997).
Elhalabi et al., *Curr. Med. Chem.*, 6(2): 93-116 (1999).
Espuelas et al., *Bioorg. Med. Chem. Lett.*, 13(15): 2557-2560 (2003).
Flomenberg et al., *Blood*, 106(5): 1867-1874 (2005).
GE Healthcare, "Ion Exchange Chromatography & Chromatofocusing: Principles and Methods," Edition AA, Amersham Biosciences, pp. 7, 11-12, 16-17, 21-23, 26-36, 41, 89, 156, 160, 161 (2004).
Gross et al., *Eur. J. Biochem,.* 177(3): 583-589 (1988).
Guo et al., *Appl. Biochem. Biotechnol.*, 68(1-2): 1-20 (1997).
Hällgren et al., *J. Carb. Chem.*, 14(4-5): 453-464 (1995).
Hermanson et al., *Immobilized Affinity Ligand Techniques*, Academic Press (1992) (Table of Contents).
Hermanson, *Bioconjugate Techniques*, Academic Press, San Diego (1996) (Table of Contents).
Hill et al., *Biol. Blood Marrow Trans.*, 12: 603-607 (2006).
Hu et al., *Mol. Cell. Biol.*, 18(10): 6063-6074 (1998).
Hübel et al., *Ann. Hematol.*, 82: 207-213 (2003).
Kennedy, "Hydrophobic-Interaction Chromatography," in *Current Protocols in Protein Science*, pp. 8.4.1-8.4.21, Wiley (1995).
Kroschinsky et al., *Trans. Apher. Sci.*, 38: 237-244 (2008).
Krystal et al., *Blood*, 67(1): 71-99 (1986).
Liles et al., *Transfusion*, 45: 295-300 (2005).
Natsuka et al., *J. Biol. Chem.*, 269(24): 16789-16794 (1994).
NCBI—Accession No. NCAA26095 (2 pgs.) (2006).
NCBI—Accession No. NP_058697 (3 pgs.) (2007).
NCBI—Accession No. NP_999299 (2 pgs.) (2007).
NCBI Database hits for erythropoietin protein sequences (3 pgs.) (2007).
Orskov et al., *J. Biol. Chem.*, 264(22): 12826-12829 (1989).
O'Shannessy et al., *J. Appl. Biochem.*, 7: 347-355 (1985).
PNGase-F Amidase Sequence from F. Meningosepticum (RN 128688-70-0) (2007).
PNGase-F Amidase Sequence from F. Meningosepticum (RN 128688-71-1) (2007).
Quelle et al., *Blood*, 74(2): 652-657 (1989).
R & D Systems, Fibroblast Growth Factors (FGFs), Internet page from www.rndsystems.com/mini_review_detail_objectname_MR01_FGFs.aspx, 2001, printed Mar. 10, 2011.
Rathnam et al., *Biochim. Biophys. Acta*, 624(2): 436-442 (1980).
Saxon et al., *J. Am. Chem. Soc.*, 124(50): 14893-14902 (2002).
Schwarz et al., *Nucl. Med. Biol.*, 26(4):383-388 (1999).
Srivastava et al., *J. Biol. Chem.*, 267(31): 22356-22361 (1992).
Ten Hagen et al., *J. Biol. Chem.*, 274(39): 27867-27874 (1999).
Tom et al., *AAPS Journal*, 9(2): E227-E234 (2007).
Uptima, Detergents: Solubilization of Biomolecules, Internet page from www.interchim.com/interchim/bio/produits_uptima/product_line/p1p_detergents.htm, 2001, printed Nov. 14, 2011.
Van Reis et al., *Biotechnol. Bioeng.*, 38(4): 413-422 (1991).
Veronese, *Biomaterials*, 22(5): 405-417 (2001).
Weston et al., *J. Biol. Chem.*, 267(6): 4152-4160 (1992).
Wong et al., *J. Org. Chem.*, 47(27): 5416-5418 (1982).
Yin et al., *Pharm. Res.*, 21(12): 2377-2383 (2004).
Zhang et al., *Biochim. Biophys. Acta*, 1425: 441-452 (1998).
Office Action dated Sep. 21, 2012 in U.S. Appl. No. 12/663,748.
Office Action dated Sep. 24, 2012 in U.S. Appl. No. 12/784,323.
Office Action dated Sep. 25, 2012 in U.S. Appl. No. 13/186,726.
Office Action dated Oct. 23, 2012 in U.S. Appl. No. 12/811,963.
Office Action dated Nov. 9, 2012 in U.S. Appl. No. 12/663,056.
Office Action dated Nov. 26, 2012 in U.S. Appl. No. 13/215,439.
Office Action dated Dec. 21, 2012 in U.S. Appl. No. 13/246,512.
Office Action dated Jan. 17, 2013 in U.S. Appl. No. 13/541,185.
Office Action dated Mar. 6, 2013 in U.S. Appl. No. 13/157,575.
Office Action dated Mar. 13, 2013 in U.S. Appl. No. 12/811,963.
Office Action dated Mar. 14, 2013 in U.S. Appl. No. 12/784,323.
Perrin et al., "Common Physical Techniques Used in Purification," in *Purification of Laboratory Chemicals*, pp. 30-31, Pergamon (1980).
Song et al., *Mar. Drugs*, 1: 34-45 (2003).
Ajisaka et al., *Biosci. Biotechnol. Biochem.*, 65(5): 1240-1243 (2001).
Andree et al., *Biochim. Biophys. Acta*, 544(3): 489-495 (1978).
Apicella et al., *Infect. Immun.*, 55(8): 1755-1761 (1987).
Arsequell et al., *Tetrahedron: Asymmetry*, 10(16): 3045-3094 (1999).
ATCC Catalog of Bacteria and Bacteriophages, 17th ed., p. 150-151 (1989).
Auge et al., *Carbohydr. Res.*, 151: 147-156 (1986).
Auge et al., *Carbohydr. Res.*, 200: 257-268 (1990).
Avigad et al., *J. Biol. Chem.*, 237(9): 2736-2743 (1962).
Barker et al., *J. Biol. Chem.*, 247(22): 7135-7147 (1972).
Bayer et al., *Glycobiology*, 13(11): 890-891 (2003).
Bertozzi et al., *J. Am. Chem. Soc.*, 114(26): 10639-10641 (1992).
Biemann et al., *Science*, 237(4818): 992-998 (1987).
Binder et al., *Tetrahedron*, 50(35): 10407-10418 (1994).
Bishop et al., *Endocrinology*, 136(6): 2635-2640 (1995).
Bocci, *Adv. Drug Deliv. Rev.*, 4(2): 149-169 (1989).
Borman, *Chem. Eng. News*, 84(36): 13-22 (2006).
Breton et al., *Curr. Opin. Struct. Biol.*, 9(5): 563-571 (1999).
Breton et al., *Biochimie*, 83(8): 713-718 (2001).
Brinkman-Van der Linden et al., *J. Biol. Chem.*, 271(24): 14492-14495 (1996).
Broquet et al., *Eur. J. Biochem.* 123(1): 9-13 (1982).
Burczak et al., *Biochim. Biophys. Acta*, 804(4): 442-449 (1984).
Burns et al., *J. Org. Chem.*, 56(8): 2648-2650 (1991).
Calvet, *Pediatr. Nephrol.*, 5(6): 751-757 (1991).
Carlson et al., *J. Biol. Chem.*, 248(16): 5742-5750 (1973).
Chang et al, *Biotechnol. Bioprocess Eng.*, 3(1): 40-43 (1998).
Chang et al., *Biochemistry*, 38(34): 10940-10948 (1999).
Clogston et al., *J. Chromatogr. A*, 637(1): 55-62 (1993).
Corfield, "Analysis of Sugar Sequences in Glycoproteins by Glycosidase Digestion and Gel Filtration," *Methods in Molecular Biology*, 19: 269-286 (1993).
Dabkowski et al., *Transplant Proc.*, 25(5): 2921 (1993).
Danaher et al., *J. Bacteriol.*, 177(24): 7275-7279 (1995).
Datta et al., *J. Biol. Chem.*, 270(4): 1497-1500 (1995).
David et al., *Pure Appl. Chem.*, 59(11): 1501-1508 (1987).
Davis et al., *Synlett 1999*, (9): 1495-1507 (1999).
De Rosa et al., *Phytochemistry*, 42(4): 1031-1034 (1996).
DeAngelis et al., *Biochemistry*, 33(31): 9033-9039 (1994).
DeLuca et al., *J. Am. Chem. Soc.*, 117(21): 5869-5870 (1995).
Dennis et al., *J. Biol. Chem.*, 277(38): 35035-35043 (2002).
Dickinson et al., *Proc. Natl. Acad. Sci. USA*, 93(25): 14379-14384 (1996).
Dreyfus et al., *Anal. Biochem.*, 249(1): 67-78 (1997).
Dudas et al., *Infect. Immun.*, 56(2): 499-504 (1988).
Dudziak et al., *Tetrahedron*, 56(32): 5865-5869 (2000).
Edano et al., *Biol. Pharm. Bull.*, 21(4): 382-385 (1998).
Ellis, "Vaccines" Plotkin et al. (eds.), Chapter 29, W.B. Saunders Co., Philadelphia. p. 568-575 (1988).
EMBL Accession No. M80599 and M86935 (Jan. 23, 1992).
EMBL Accession No. S56361 (May 4, 1993).
EMBL Accession No. 000039 (Jun. 2, 1994).
Ernst et al., *Glycoconj. J.*, 16(2): 161-170 (1999).
Fu et al., *Bioconjug. Chem.*, 12(2): 271-279 (2001).
Fujita et al., *Biochim. Biophys. Acta*, 1528(1): 9-14 (2001).
GE Healthcare Instructions 28-9064-05 AA (2006).
GE Healthcare Instructions 28-9064-05 AC (2006).
Genbank Accession No. AAA98726, "Factor IX," pp. 1-3 (Apr. 14, 2009).
Genbank Accession No. CAA01607, "Factor IX of *Homo sapiens*," pp. 1-2 (Apr. 14, 2009).
Genbank Accession No. D49915 (Sep. 1, 1995).
Genbank Accession No. U02304 (Mar. 8, 1994).
Genbank Accession No. U18918 (Oct. 1, 1995).
Gibson et al., *J. Bacteriol.*, 175(9): 2702-2712 (1993).
Gilbert, "Methods in Enzymology" Packer (ed.), 2(251): 8-28, Biothiols Part A,Elsevier (1995).
Gilbert et al., "The Synthesis of Sialylated Oligosaccharides Using a CMP-Neu5Ac Synthetase/Sialyltransferase Fusion," *Nature Biotechnology*, 16: 769-772 (1998).

(56) References Cited

OTHER PUBLICATIONS

Gillespie et al., *FASEB Journal*, 4(7): A2068 [Abstract No. 2173] (1990).
Gillespie et al., *J. Biol. Chem.*, 267(29): 21004-21010 (1992).
Goodson et al., *Biotechnology* (N.Y.), 8(4): 343-346 (1990).
Greenwell et al., *Blood Group A Synthesising Activity of the Blood Group B Gene Specified .alpha.-3-D-Galactosyl Transferase*, p. 268-269 (1979).
Greenwell et al., *Carbohydr. Res.*, 149(1): 149-170 (1986).
Gross et al., *Eur. J. Biochem.*, 168(3): 595-602 (1987).
Grundmann et al., *Nucleic Acids Res.*, 18(3): 667 (1990).
Gu et al., *FEBS Lett.*, 275(1-2): 83-86 (1990).
Guivisdalsky et al., *J. Med. Chem.*, 33(9): 2614-2621 (1990).
Hakomori et al., "Methods in Enzymology" Fleischer et al. (eds.), 33(32): 345-367, Biomembranes Part B, Elsevier USA. (1974).
Hedner et al., "Recombinant Activated Factor VII in the Treatment of Bleeding Episodes in Patients With Inherited and Acquired Bleeding Disorders," *Transfusion Medicine Reviews*, VII(2): 78-83 (1993).
Heimgartner et al., "Reversible and Irreversible Cross-Linking of Immunoglobulin Heavy Chains Through Their Carbohydrate Residues," *Biochem. J.*, 267: 585-591 (1990).
Helling et al., *Cancer Res.*, 54(1): 197-203 (1994).
Higa et al., *J. Biol. Chem.*, 260(15): 8838-8849 (1985).
Higashi et al., *J. Biol. Chem.*, 272(41): 25724-25730 (1997).
High et al., *Mol. Microbiol.*, 9(6): 1275-1282 (1993).
Hoffman et al., *Thromb. Haemost.*, 85(6): 958-965 (2001).
Ichikawa et al., *J. Am. Chem. Soc.*, 113(12): 4698-4700 (1991).
Ichikawa et al., *J. Am. Chem. Soc.*, 113(16): 6300-6302 (1991).
Ito et al., *J. Am. Chem. Soc.*, 115(4): 1603-1605 (1993).
Japanese Biochemical Society, "New Course in Biochemistry Experiments 3, Sugars I, Glycoproteins (top)," Tokyo Kagaku Dojin K.K., First Edition, p. 340 (1990).
Jennemann et al., *J. Biochem.*, 115(6): 1047-1052 (1994).
Jennings et al., *Mol. Microbiol.*, 10(2): 361-369 (1993).
John et al., *J. Biol. Chem.*, 266(29): 19303-19311 (1991).
Jonsson et al., *EMBO J.*, 10(2): 477-488 (1991).
Joziasse et al., *J. Biol. Chem.*, 260(8): 4941-4951 (1985).
Joziasse et al., *J. Biol. Chem.*, 264(24): 14290-14297 (1989).
Kawai et al., *J. Lipid Res.*, 26(3): 338-343 (1985).
Kerwood et al., *Biochemistry*, 31(51): 12760-12768 (1992).
Khidekel et al., *J. Am. Chem. Soc.*, 125(52): 16162-16163 (2003).
Kitagawa et al., *Biochem. Biophys. Res. Commun.*, 194(1): 375-382 (1993).
Kitagawa et al., *J. Biol. Chem.*, 269(27): 17872-17878 (1994).
Knight et al., *Mol. Microbiol.*, 6(11): 1565-1573 (1992).
Koeller et al., "Complex Carbohydrate Synthesis Tools for Glycobiologists: Enzyme-Based Approach and Programmable One-Pot Strategies," *Glycobiology*, 10(11): 1157-1169 (2000).
Kogan, *Synth. Commun.*, 22(16): 2417-2424 (1992).
Koike et al., *Carbohydr. Res.*, 162(2): 237-246 (1987).
Kurosawa et al., *Eur. J. Biochem.*, 219(1-2): 375-381 (1994).
Larsen et al, *Proc. Natl. Acad. Sci. USA*, 86(21): 8227-8231 (1989).
Lee et al., *Science*, 239(4845): 1288-1291 (1988).
Lidholt et al, *Biochem. J.*, 261(3): 999-1007 (1989).
Livingston et al., *J. Biol. Chem.*, 268(16): 11504-11507 (1993).
Lundstrom-Ljung et al., *J. Biol. Chem.*, 270(14): 7822-7828 (1995).
Luo et al., "Spontaneous Calcification of Arteries and Cartilage in Mice Lacking Matrix GLA Protein," *Nature*, 386: 78-81 (1997).
Maccioni et al., *Biochim Biophys Acta.*, 1437(2): 101-118 (1999).
Mackenzie et al., *J. Am. Chem. Soc.*, 120(22): 5583-5584 (1998).
Madnick et al., *Arch. Biochem. Biophys.*, 212(2): 432-442 (1981).
Mandrell et al., *J. Exp. Med.*, 168(1): 107-126 (1988).
Mandrell et al., *J. Exp. Med.*, 171(5): 1649-1664 (1990).
Mandrell et al., *J. Bacteriol.*, 173(9): 2823-2832 (1991).
Mandrell, *Infect. Immun.*, 60(7): 3017-3020 (1992).
Manfioletti et al., "The Protein Encoded by a Growth Arrest-Specific Gene (gas6) Is a New Member of the Vitamin K-Dependent Proteins Related to Protein S, a Negative Coregulator in the Blood Coagulation Cascade," *Mol. Cell. Bio.*, 13(8): 4976-4985 (1993).
Marinier et al., *J. Med. Chem.*, 40(20): 3234-3247 (1997).
Mathews et al., *J. Biol. Chem.*, 262(16): 7537-7545 (1987).
Mizuguchi et al., *Thromb. Haemost.*, Abstract 1474: 466, Suppl. (Aug. 1999).
Muramatsu et al., *Comprehensive Research on Clinical Organ Xenotransplantation by Genetic Regulation*, p. 10-12. (1997).
Nelsestuen et al., "Vitamin K-Dependent Proteins," *Vitamins and Hormones*, 58: 355-389 (2000).
Nemansky et al., *FEBS Lett.*, 312(1): 31-36 (1992).
Nilsson, *Trends Biotechnol.*, 6(10): 256-264 (1988).
Nucci et al., *Adv. Drug Deliv. Rev.*, 6(2): 133-151 (1991).
Nunez et al., *Biochemistry*, 15(17): 3843-3847 (1976).
Palcic et al., *Glycobiology*, 1(2): 205-209 (1991).
Parsons et al., *Microb. Pathog.*, 7(1): 63-72 (1989).
Patra et al., *Protein Expr. Purif.*, 18(2): 182-192 (2000).
Paulson et al., *Chemical Abstracts*, 86(25): 213 [Abstract No. 185016b] (1977).
Paulson et al., *J. Biol. Chem.*, 252(7): 2356-2362 (1977).
Paulson et al., *J. Biol. Chem.*, 264(19):10931-10934 (1989).
Pfaffli et al., *Carbohydr. Res.*, 23(2): 195-206 (1972).
Pradel et al., *J. Bacteriol.*, 174(14): 4736-4745 (1992).
Preuss et al., *J. Biol. Chem.*, 268(35): 26273-26278 (1993).
Probert et al., *Tetrahedron Lett.*, 38(33): 5861-5864 (1997).
Raju et al., "Glycoengineering of Therapeutic Glycoproteins: In Vitro Galactosylation and Sialylation of Glycoproteins with Terminal N-Acetylglucosamine and Galactose Residues," *Biochemistry*, 40(30): 8868-8876 (2001).
Rao et al., *Protein Sci.*, 8(11): 2338-2346 (1999).
Rearick et al., *J. Biol. Chem.*, 254(11): 4444-4451 (1979).
Rice et al., *J. Biol. Chem.*, 265(30): 18423-18428 (1990).
Robertson et al., *Mol. Microbiol.*, 8(5): 891-901 (1993).
Rosevear et al., *Biochemistry*, 21(6): 1421-1431 (1982).
Sadler et al., *J. Biol. Chem.*, 254(11): 4434-4442 (1979).
Sadler et al., *J. Biol. Chem.*, 254(13): 5934-5941 (1979).
Saenko et al., *Haemophilia*, 12(suppl. 3): 42-51 (2006).
Sambrook et al., "Molecular Cloning: A Laboratory Manual" 2nd ed., Cold Spring Harbor Laboratory Press, Cold Spring Harbor, New York, p. 9.50-9.51 (1989).
Sandlin et al., *J. Bacteriol.*, 176(10): 2930-2937 (1994).
Schmidt et al., *Trends Cardiovasc. Med.*, 13(1): 39-45 (2003).
Schneider et al., *Infect. Immun.*, 56(4): 942-946 (1988).
Schneider et al., *J. Exp. Med.*, 174(6): 1601-1605 (1991).
Schram et al., *Biochim. Biophys. Acta*, 482(1): 138-144 (1977).
Sears et al., *Science*, 291(5512): 2344-2350 (2001).
Shames et al., *Glycobiology*, 1(2): 187-191 (1991).
Shao et al., *Glycobiology*, 12(11): 763-770 (2002).
Simon et al., *J. Am. Chem. Soc.*, 110(21): 7159-7163 (1988).
Sogin et al., *Biochemistry* 19(23): 5417-5420 (1980).
Sorensen et al., "Incorporation of an Active Site Inhibitor in Factor VIIa Alters the Affinity for Tissue Factor," *J. Biol. Chem.*, 272(18): 11863-11868 (1997).
Stamenkovic et al., *J. Exp. Med.*, 172(2): 641-643 (1990).
Stennicke et al., *Anal. Biochem.*, 248(1): 141-148 (1997).
Stephens et al., *Infect Immun.*, 62(7): 2947-2952 (1994).
Stoolmiller et al., *J. Biol. Chem.*, 244(2): 236-246 (1969).
Suzuki et al., *J. Biol. Chem.*, 260(3): 1362-1365 (1985).
Swiss-Prot Accession No. P19817 (Feb. 1, 1991).
Swiss-Prot Accession No. P25740 (May 1, 1992).
Swiss-Prot Accession No. P27129 (Aug. 1, 1992).
Takegawa et al., *J. Biol. Chem.*, 270(7): 3094-3099 (1995).
Takeya et al., *J. Biol. Chem.*, 263(29): 14868-14877 (1988).
Takeya et al., *Jpn. J. Med. Sci. Biol.*, 46(1): 1-15 (1993).
Tarui et al., *J. Biosci. Bioeng.*, 90(5): 508-514 (2000).
Toone et al., *Tetrahedron*, 45(17): 5365-5422 (1989).
Tsai et al., *Infect. Immun.*, 59(10): 3604-3609 (1991).
Tsuboi et al., "6'-Sulfo Sialyl Le$^x$ but Not 6-Sulfo Sialyl Le$^x$ Expressed on the Cell Surface Supports L-selectin-mediated Adhesion," *J. Biol. Chem.*, 271(44): 27213-27216 (1996).
Tsuji, "Molecular Cloning and Functional Analysis of Sialyltransferases," *J. Biochemistry*, 120: 1-13 (1996).
Tsujihara et al., *Chem. Pharm. Bull.*, (Tokyo) 29(11): 3262-3273 (1981).
Van den Eijnden et al., *J. Biol. Chem.*, 256(7): 3159-3162 (1981).
Van den Eijnden et al., *J. Biol. Chem.*, 258(6): 3435-3437 (1983).

(56) References Cited

OTHER PUBLICATIONS

Van Putten et al., *EMBO J.*, 12(11): 4043-4051 (1993).
Van Roey al., *Biochemistry*, 33(47): 13989-13996 (1994).
Vann et al., *J Biol Chem.*, 262(36): 17556-17562 (1987.
Verheul et al., *Microbiol. Rev.*, 57(1): 34-49 (1993).
Vijay et al., *J. Biol. Chem.*, 250(1): 164-170 (1975).
Waddling et al., *Biochemistry*, 39(27): 7878-7885 (2000).
Wakarchuk et al., *J. Biol. Chem.*, 271(32): 19166-19173 (1996).
Wang et al., *Protein Eng.*, 10(4): 405-411 (1997).
Webster et al., *J. Biol. Chem.*, 258(17): 10637-10641 (1983).
Weinstein et al., *J. Biol. Chem.*, 257(22): 13835-13844 (1982).
Weinstein et al., *J. Biol. Chem.*, 257(22): 13845-13853 (1982).
Wen et al., *FASEB Journal*, 6(1): A231 [abstract No. 1329] (1992).
Wen et al., *J. Biol. Chem.*, 267(29): 21011-21019 (1992).
Whisstock et al., *Q. Rev. Biophys.*, 36(3): 307-340 (2003).
Wikipedia Image:Ceramide.svg, http://en.wikipedia.org/wiki/Ceramide, pp. 1-2 (2007, updated).
Wong et al., *J. Org. Chem.*, 57(16): 4343-4344 (1992).
Xiao et al., *J. Biol. Chem.*, 280(22): 21099-21106 (2005).
Yamamoto et al., *J. Biol. Chem.*, 265(31): 19257-19262 (1990).
Yamamoto et al., *Nature*, 345(6272): 229-233 (1990).
Yamasaki et al., *J. Bacteriol.*, 175(14): 4565-4568 (1993).
Yoshikawa et al., *Phytochemistry*, 34(5): 1431-1433 (1993).
Zalipsky et al., *Polymer Prepr.*, 27(1): 1-2 (1986).
Zalipsky et al., *Int. J. Pept. Protein Res.*, 30(6): 740-783 (1987).
Zapata et al., *J. Biol. Chem.*, 264(25): 14769-14774 (1989).
Zhou et al., *J. Biol. Chem.*, 269(15): 11162-11169 (1994).
Drucker et al., "Glucagon Gene Expression in Vertebrate Brain," *J. Biol. Chem.*, 263(27): 13475-13478 (1988).
Monfardini et al., "A Branched Monomethoxypoly (ethylene glycol) for Protein Modification," *Bioconjug. Chem.*, 6(1): 62-69 (1995).
Moscatelli et al., "Enzymatic Properties of a β-Glucanase from *Bacillus subtilis*," *J. Biol. Chem.*, 236(11): 2858-2862 (1961).
Rabina et al., "Analysis of Nucleotide Sugars from Cell Lysates by Ion-Pair Solid-Phase Extraction and Reversed-Phase High-Performance Liquid Chromatography," *Glycoconj. J.*, 18(10): 799-805 (2001).
Office Action dated Mar. 21, 2013 in U.S. Appl. No. 13/541,185.
Office Action dated May 9, 2013 in U.S. Appl. No. 12/594,326.
Office Action dated May 21, 2013 in U.S. Appl. No. 12/811,963.
Office Action dated Jun. 6, 2013 in U.S. Appl. No. 11/701,949.
Office Action dated Jul. 11, 2013 in U.S. Appl. No. 11/652,467.
Office Action dated Jul. 17, 2013 in U.S. Appl. No. 13/215,439.
Office Action dated Jul. 30, 2013 in U.S. Appl. No. 13/246,512.
Office Action dated Aug. 12, 2013 in U.S. Appl. No. 13/541,185.
Office Action dated Sep. 6, 2013 in U.S. Appl. No. 12/784,323.
Office Action dated Sep. 16, 2013 in U.S. Appl. No. 11/781,885.
Office Action dated Sep. 17, 2013 in U.S. Appl. No. 11/781,888.
Office Action dated Sep. 25, 2013 in U.S. Appl. No. 12/663,748.
Office Action dated Oct. 10, 2013 in U.S. Appl. No. 10/581,538.
Office Action dated Oct. 16, 2013 in U.S. Appl. No. 11/597,258.
Office Action dated Nov. 7, 2013 in U.S. Appl. No. 12/811,963.
Office Action dated Dec. 5, 2013 in U.S. Appl. No. 10/565,331.
Weerapana et al., "Investigating Bacterial N-Linked Glycosylation: Synthesis and Glycosyl Acceptor Activity of the Undecaprenyl Pyrophosphate-Linked Bacillosamine," *J. Am. Chem. Soc.*, 127(40): 13766-13767 (2005).

\* cited by examiner

CMP-Glycil Sialic Acid Process Flow Chart

CMP-SA-PEG Process Flow Diagram chST6GalNac Purification Process Overview

FIGURE 7A

| Protein | Organism | EC# | GenBank / GenPept | | SwissProt | PDB / 3D |
|---|---|---|---|---|---|---|
| At1g08280 | Arabidopsis thaliana | n.d. | AC011438 BT004583 NC_003070 | AAF18241.1 AAO42829.1 NP_172305.1 | Q84W00 Q9SGD2 | |
| At1g08660/F22O13.14 | Arabidopsis thaliana | n.d. | AC003981 AY064135 AY124807 NC_003070 NM_180609 | AAF99778.1 AAL36042.1 AAM70516.1 NP_172342.1 NP_850940.1 | Q8VZJ0 Q9FRR9 | |
| At3g48820/T21J18_90 | Arabidopsis thaliana | n.d. | AY080589 AY133816 AL132963 NM_114741 | AAL85966.1 AAM91750.1 CAB87910.1 NP_190451.1 | Q8RY00 Q9M301 | |
| α-2,3-sialyltransferase (ST3GAL-IV) | Bos taurus | n.d. | AJ584673 | CAE48298.1 | | |
| α-2,3-sialyltransferase (St3Gal-V) | Bos taurus | n.d. | AJ585768 | CAE51392.1 | | |
| α-2,6-sialyltransferase (Siat7b) | Bos taurus | n.d. | AJ620651 | CAF05850.1 | | |
| α-2,8-sialyltransferase (SIAT8A) | Bos taurus | 2.4.99.8 | AJ699418 | CAG27880.1 | | |
| α-2,8-sialyltransferase (Siat8D) | Bos taurus | n.d. | AJ699421 | CAG27883.1 | | |
| α-2,8-sialyltransferase ST8Siα-III (Siat8C) | Bos taurus | n.d. | AJ704563 | CAG28696.1 | | |
| CMP α-2,6-sialyltransferase (ST6Gal I) | Bos taurus | 2.4.99.1 | Y15111 NM_177517 | CAA75385.1 NP_803483.1 | O18974 | |
| sialyltransferase 8 (fragment) | Bos taurus | n.d. | AF450088 | AAL47018.1 | Q8WN13 | |
| sialyltransferase ST3Gal-II (Siat4B) | Bos taurus | n.d. | AJ748841 | CAG44450.1 | | |
| sialyltransferase ST3Gal-III (Siat6) | Bos taurus | n.d. | AJ748842 | CAG44451.1 | | |
| sialyltransferase ST3Gal-VI (Siat10) | Bos taurus | n.d. | AJ748843 | CAG44452.1 | | |
| ST3Gal I | Bos taurus | n.d. | AJ305086 | CAC24698.1 | Q9BEG4 | |
| St6GalNAc-VI | Bos taurus | n.d. | AJ620949 | CAF06586.1 | | |
| CDS4 | Branchiostoma floridae | n.d. | AF391289 | AAM18873.1 | Q8T771 | |
| polysialyltransferase (PST) (fragment) ST8Sia IV | Cercopithecus aethiops | 2.4.99.- | AF210729 | AAF17105.1 | Q9TT09 | |
| polysialyltransferase (STX) (fragment) ST8Sia II | Cercopithecus aethiops | 2.4.99.- | AF210318 | AAF17104.1 | Q9TT10 | |
| α-2,3-sialyltransferase ST3Gal I (Siat4) | Ciona intestinalis | n.d. | AJ626815 | CAF25173.1 | | |
| α-2,3-sialyltransferase ST3Gal I (Siat4) | Ciona savignyi | n.d. | AJ626814 | CAF25172.1 | | |
| α-2,8-polysialyltransferase ST8Sia IV | Cricetulus griseus | 2.4.99.- | Z46801 | AAE28634 CAA86822.1 | Q64690 | |
| Gal β-1,3/4-GlcNAc α-2,3-sialyltransferase St3Gal I | Cricetulus griseus | n.d. | AY266675 | AAP22942.1 | Q80WL0 | |
| Gal β-1,3/4-GlcNAc α-2,3-sialyltransferase St3Gal II (fragment) | Cricetulus griseus | n.d. | AY266676 | AAP22943.1 | Q80WK9 | |
| α-2,3-sialyltransferase ST3Gal I (Siat4) | Danio rerio | n.d. | AJ783740 | CAH04017.1 | | |
| α-2,3-sialyltransferase ST3Gal II (Siat5) | Danio rerio | n.d. | AJ783741 | CAH04018.1 | | |

FIGURE 7B

| Protein | Organism | EC# | GenBank / GenPept | | SwissProt | PDB / 3D |
|---|---|---|---|---|---|---|
| α-2,3-sialyltransferase ST3Gal III (Siat6) | Danio rerio | n.d. | AJ626821 | CAF25179.1 | | |
| α-2,3-sialyltransferase ST3Gal IV (Siat4c) | Danio rerio | n.d. | AJ744809 | CAG32845.1 | | |
| α-2,3-sialyltransferase ST3Gal V-r (Siat5-related) | Danio rerio | n.d. | AJ783742 | CAH04019.1 | | |
| α-2,6-sialyltransferase ST6Gal I (Siat1) | Danio rerio | n.d. | AJ744801 | CAG32837.1 | | |
| α-2,6-sialyltransferase ST6GalNAc II (Siat7B) | Danio rerio | n.d. | AJ634459 | CAG25680.1 | | |
| α-2,6-sialyltransferase ST6GalNAc V (Siat7E) (fragment) | Danio rerio | n.d. | AJ646874 | CAG26703.1 | | |
| α-2,6-sialyltransferase ST6GalNAc VI (Siat7F) (fragment) | Danio rerio | n.d. | AJ646883 | CAG26712.1 | | |
| α-2,8-sialyltransferase ST8Sia I (Siat 8A) (fragment) | Danio rerio | n.d. | AJ715535 | CAG29374.1 | | |
| α-2,8-sialyltransferase ST8Sia III (Siat 8C) (fragment) | Danio rerio | n.d. | AJ715543 | CAG29382.1 | | |
| α-2,8-sialyltransferase ST8Sia IV (Siat 8D) (fragment) | Danio rerio | n.d. | AJ715545 | CAG29384.1 | | |
| α-2,8-sialyltransferase ST8Sia V (Siat 8E) (fragment) | Danio rerio | n.d. | AJ715546 | CAG29385.1 | | |
| α-2,8-sialyltransferase ST8Sia VI (Siat 8F) (fragment) | Danio rerio | n.d. | AJ715551 | CAG29390.1 | | |
| β-galactosamide α-2,6-sialyltransferase II (ST6Gal II) | Danio rerio | n.d. | AJ627627 | CAF29495.1 | | |
| N-glycan α-2,8-sialyltransferase | Danio rerio | n.d. | BC050483 AY055462 NM_153662 | AAH50483.1 AAL17875.1 NP_705948.1 | Q7ZU51 Q8QH83 | |
| ST3Gal III-related (siat6r) | Danio rerio | n.d. | BC053179 AJ626820 NM_200355 | AAH53179.1 CAF25178.1 NP_956649.1 | Q7T3B9 | |
| St3Gal-V | Danio rerio | n.d. | AJ619960 | CAF04061.1 | | |
| st6GalNAc-VI | Danio rerio | n.d. | BC060932 AJ620947 | AAH60932.1 CAF06584.1 | | |
| α-2,6-sialyltransferase (CG4871) ST6Gal I | Drosophila melanogaster | 2.4.99.1 | AE003465 AF218237 AF397532 AE003465 NM_079129 NM_166684 | AAF47256.1 AAG13185.1 AAK92126.1 AAM70791.1 NP_523853.1 NP_726474.1 | Q9GU23 Q9W121 | |
| α-2,3-sialyltransferase (ST3Gal-VI) | Gallus gallus | n.d. | AJ585767 AJ627204 | CAE51391.1 CAF25503.1 | | |
| α-2,3-sialyltransferase ST3Gal I | Gallus gallus | 2.4.99.4 | X80503 NM_205217 | CAA56666.1 NP_990548.1 | Q11200 | |
| α-2,3-sialyltransferase ST3Gal IV (fragment) | Gallus gallus | 2.4.99.- | AF035250 | AAC14163.1 | O73724 | |
| α-2,3-sialyltransferase (ST3GAL-II) | Gallus gallus | n.d. | AJ585761 | CAE51385.2 | | |
| α-2,6-sialyltransferase (Siat7b) | Gallus gallus | n.d. | AJ620653 | CAF05852.1 | | |
| α-2,6-sialyltransferase ST6Gal I | Gallus gallus | 2.4.99.1 | X75558 NM_205241 | CAA53235.1 NP_990572.1 | Q92182 | |
| α-2,6-sialyltransferase | Gallus gallus | 2.4.99.3 | - | AAE68028.1 | Q92183 | |

FIGURE 7C

| Protein | Organism | EC# | GenBank / GenPept | | SwissProt | PDB / 3D |
|---|---|---|---|---|---|---|
| ST6GalNAc I | | | X74946<br>NM_205240 | AAE68029.1<br>CAA52902.1<br>NP_990571.1 | | |
| α-2,6-sialyltransferase ST6GalNAc II | Gallus gallus | 2.4.99.- | X77775<br>NM_205233 | AAE68030.1<br>CAA54813.1<br>NP_990564.1 | Q92184 | |
| α-2,6-sialyltransferase ST6GalNAc III (SIAT7C) (fragment) | Gallus gallus | n.d. | AJ634455 | CAG25677.1 | | |
| α-2,6-sialyltransferase ST6GalNAc V (SIAT7E) (fragment) | Gallus gallus | n.d. | AJ646877 | CAG26706.1 | | |
| α-2,8-sialyltransferase (GD3 Synthase) ST8Sia I | Gallus gallus | 2.4.99.- | U73176 | AAC28888.1 | P79783 | |
| α-2,8-sialyltransferase (SIAT8B) | Gallus gallus | n.d. | AJ699419 | CAG27881.1 | | |
| α-2,8-sialyltransferase (SIAT8C) | Gallus gallus | n.d. | AJ699420 | CAG27882.1 | | |
| α-2,8-sialyltransferase (SIAT8F) | Gallus gallus | n.d. | AJ699424 | CAG27886.1 | | |
| α-2,8-syalyltransferase ST8Siα-V (SIAT8C) | Gallus gallus | n.d. | AJ704564 | CAG28697.1 | | |
| β-galactosamide α-2,6-sialyltransferase II (ST6Gal II) | Gallus gallus | n.d. | AJ627629 | CAF29497.1 | | |
| GM3 synthase (SIAT9) | Gallus gallus | 2.4.99.9 | AY515255 | AAS83519.1 | | |
| polysialyltransferase ST8Sia IV | Gallus gallus | 2.4.99.- | AF008194 | AAB95120.1 | O42399 | |
| α-2,3-sialyltransferase ST3Gal I | Homo sapiens | 2.4.99.4 | L29555<br>AF059321<br>L13972<br>AF155238<br>AF186191<br>BC018357<br>NM_003033<br>NM_173344 | AAA36612.1<br>AAC17874.1<br>AAC37574.1<br>AAD39238.1<br>AAG29876.1<br>AAH18357.1<br>NP_003024.1<br>NP_775479.1 | Q11201<br>O60677<br>Q9UN51 | |
| α-2,3-sialyltransferase ST3Gal II | Homo sapiens | 2.4.99.4 | U63090<br>BC036777<br>X96667<br>NM_006927 | AAB40389.1<br>AAH36777.1<br>CAA65447.1<br>NP_008858.1 | Q16842<br>O00654 | |
| α-2,3-sialyltransferase ST3Gal III (SiaT6) | Homo sapiens | 2.4.99.6 | L23768<br>BC050380<br>AF425851<br>AF425852<br>AF425853<br>AF425854<br>AF425855<br>AF425856<br>AF425857<br>AF425858<br>AF425859<br>AF425860<br>AF425861<br>AF425862<br>AF425863<br>AF425864<br>AF425865<br>AF425866<br>AF425867<br>AY167992<br>AY167993<br>AY167994 | AAA35778.1<br>AAH50380.1<br>AAO13859.1<br>AAO13860.1<br>AAO13861.1<br>AAO13862.1<br>AAO13863.1<br>AAO13864.1<br>AAO13865.1<br>AAO13866.1<br>AAO13867.1<br>AAO13868.1<br>AAO13869.1<br>AAO13870.1<br>AAO13871.1<br>AAO13872.1<br>AAO13873.1<br>AAO13874.1<br>AAO13875.1<br>AAO38806.1<br>AAO38807.1<br>AAO38808.1 | Q11203<br>Q86UR6<br>Q86UR7<br>Q86UR8<br>Q86UR9<br>Q86US0<br>Q86US1<br>Q86US2<br>Q8IX43<br>Q8IX44<br>Q8IX45<br>Q8IX46<br>Q8IX47<br>Q8IX48<br>Q8IX49<br>Q8IX50<br>Q8IX51<br>Q8IX52<br>Q8IX53<br>Q8IX54<br>Q8IX55<br>Q8IX56 | |

FIGURE 7D

| Protein | Organism | EC# | GenBank / GenPept | | SwissProt | PDB / 3D |
|---|---|---|---|---|---|---|
| | | | AY167995 | AAO38809.1 | Q8IX57 | |
| | | | AY167996 | AAO38810.1 | Q8IX58 | |
| | | | AY167997 | AAO38811.1 | | |
| | | | AY167998 | AAO38812.1 | | |
| | | | NM_006279 | NP_006270.1 | | |
| | | | NM_174964 | NP_777624.1 | | |
| | | | NM_174965 | NP_777625.1 | | |
| | | | NM_174966 | NP_777626.1 | | |
| | | | NM_174967 | NP_777627.1 | | |
| | | | NM_174969 | NP_777629.1 | | |
| | | | NM_174970 | NP_777630.1 | | |
| | | | NM_174972 | NP_777632.1 | | |
| α-2,3-sialyltransferase ST3Gal IV | Homo sapiens | 2.4.99.- | L23767 | AAA16460.1 | Q11206 | |
| | | | AF035249 | AAC14162.1 | O60497 | |
| | | | BC010645 | AAH10645.1 | Q96QQ9 | |
| | | | AY040826 | AAK93790.1 | Q8N6A6 | |
| | | | AF516602 | AAM66431.1 | Q8N6A7 | |
| | | | AF516603 | AAM66432.1 | Q8NFD3 | |
| | | | AF516604 | AAM66433.1 | Q8NFG7 | |
| | | | AF525084 | AAM81378.1 | | |
| | | | X74570 | CAA52662.1 | | |
| | | | CR456858 | CAG33139.1 | | |
| | | | NM_006278 | NP_006269.1 | | |
| α-2,3-sialyltransferase ST3Gal VI | Homo sapiens | 2.4.99.4 | AF119391 | AAD39131.1 | Q9Y274 | |
| | | | BC023312 | AAH23312.1 | | |
| | | | AB022918 | BAA77609.1 | | |
| | | | AX877828 | CAE89895.1 | | |
| | | | AX886023 | CAF00161.1 | | |
| | | | NM_006100 | NP_006091.1 | | |
| α-2,6-sialyltransferase (ST6Gal II ; KIAA1877) | Homo sapiens | n.d. | BC008680 | AAH08680.1 | Q86Y44 | |
| | | | AB058780 | BAB47506.1 | Q8IUG7 | |
| | | | AB059555 | BAC24793.1 | Q96HE4 | |
| | | | AJ512141 | CAD54408.1 | Q96JF0 | |
| | | | AX795193 | CAE48260.1 | | |
| | | | AX795193 | CAE48261.1 | | |
| | | | NM_032528 | NP_115917.1 | | |
| α-2,6-sialyltransferase (ST6GALNAC III) | Homo sapiens | n.d. | BC059363 | AAH59363.1 | Q8N259 | |
| | | | AY358540 | AAQ88904.1 | Q8NDV1 | |
| | | | AK091215 | BAC03611.1 | | |
| | | | AJ507291 | CAD45371.1 | | |
| | | | NM_152996 | NP_694541.1 | | |
| α-2,6-sialyltransferase (ST6GalNAc V) | Homo sapiens | n.d. | BC001201 | AAH01201.1 | Q9BVH7 | |
| | | | AK056241 | BAB71127.1 | | |
| | | | AL035409 | CAB72344.1 | | |
| | | | AJ507292 | CAD45372.1 | | |
| | | | NM_030965 | NP_112227.1 | | |
| α-2,6-sialyltransferase (SThM) ST6GalNAc II | Homo sapiens | 2.4.99.- | U14550 | AAA52228.1 | Q9UJ37 | |
| | | | BC040455 | AAH40455.1 | Q12971 | |
| | | | AJ251053 | CAB61434.1 | | |
| | | | NM_006456 | NP_006447.1 | | |
| α-2,6-sialyltransferase ST6Gal I | Homo sapiens | 2.4.99.1 | BC031476 | AAH31476.1 | P15907 | |
| | | | BC040009 | AAH40009.1 | | |
| | | | A17362 | CAA01327.1 | | |
| | | | A23699 | CAA01686.1 | | |
| | | | X17247 | CAA35111.1 | | |
| | | | X54363 | CAA38246.1 | | |
| | | | X62822 | CAA44634.1 | | |
| | | | NM_003032 | NP_003023.1 | | |
| | | | NM_173216 | NP_775323.1 | | |
| α-2,6-sialyltransferase ST6GalNAc I | Homo sapiens | 2.4.99.3 | BC022462 | AAH22462.1 | Q8TBJ6 | |
| | | | AY096001 | AAM22800.1 | Q9NSC7 | |
| | | | AY358918 | AAQ89277.1 | Q9NXQ7 | |
| | | | AK000113 | BAA90953.1 | | |
| | | | Y11339 | CAA72179.2 | | |

FIGURE 7E

| Protein | Organism | EC# | GenBank / GenPept | | SwissProt | PDB / 3D |
|---|---|---|---|---|---|---|
| | | | NM_018414 | NP_060884.1 | | |
| α-2,8-polysialyltransferase ST8Sia IV | Homo sapiens | 2.4.99.- | L41680 BC027866 BC053657 NM_005668 | AAC41775.1 AAH27866.1 AAH53657.1 NP_005659.1 | Q8N1F4 Q92187 Q92693 | |
| α-2,8-sialyltransferase (GD3 synthase) ST8Sia I | Homo sapiens | 2.4.99.8 | L32867 L43494 BC046158 - AY569975 D26360 X77922 NM_003034 | AAA62366.1 AAC37586.1 AAH46158.1 AAQ53140.1 AAS75783.1 BAA05391.1 CAA54891.1 NP_003025.1 | Q86X71 Q92185 Q93064 | |
| α-2,8-sialyltransferase ST8Sia II | Homo sapiens | 2.4.99.- | L29556 U82762 U33551 BC069584 NM_006011 | AAA36613.1 AAB51242.1 AAC24458.1 AAH69584.1 NP_006002.1 | Q92186 Q92470 Q92746 | |
| α-2,8-sialyltransferase ST8Sia III | Homo sapiens | 2.4.99.- | AF004668 AF003092 NM_015879 | AAB87642.1 AAC15901.2 NP_056963.1 | O43173 Q9NS41 | |
| α-2,8-sialyltransferase ST8Sia V | Homo sapiens | 2.4.99.- | U91641 CR457037 NM_013305 | AAC51727.1 CAG33318.1 NP_037437.1 | O15466 | |
| ENSP00000020221 (fragment) | | n.d. | AC023295 | - | | |
| lactosylceramide α-2,3-sialyltransferase (ST3Gal V) | Homo sapiens | 2.4.99.9 | AF105026 AF119415 BC065936 AY152815 AAP65066 AY359105 AB018356 AX876536 NM_003896 | AAD14634.1 AAF66146.1 AAH65936.1 AAO16866.1 AAP65066.1 AAQ89463.1 BAA33950.1 CAE89320.1 NP_003887.2 | Q9UNP4 O94902 | |
| N-acetylgalactosaminide α-2,6-sialyltransferase (ST6GalNAc VI) | Homo sapiens | 2.4.99.- | BC006564 BC007802 BC016299 AY358672 AB035173 AK023900 AJ507293 AX880950 CR457318 NM_013443 | AAH06564.1 AAH07802.1 AAH16299.1 AAQ89035.1 BAA87035.1 BAB14715.1 CAD45373.1 CAE91145.1 CAG33599.1 NP_038471.2 | Q969X2 Q9H8A2 Q9ULB8 | |
| N-acetylgalactosaminide α-2,6-sialyltransferase IV (ST6GalNAc IV) | Homo sapiens | 2.4.99.- | AF127142 BC036705 - AB035172 AK000600 Y17461 AJ271734 AX061620 AX068265 AX969252 NM_014403 NM_175039 | AAF00102.1 AAH36705.1 AAP63349.1 BAA87034.1 BAA91281.1 CAB44354.1 CAC07404.1 CAC24981.1 CAC27250.1 CAF14360.1 NP_055218.3 NP_778204.1 | Q9H4F1 Q9NWU6 Q9UKU1 Q9ULB9 Q9Y3G3 Q9Y3G4 | |
| ST8SIA-VI (fragment) | Homo sapiens | n.d. | AJ621583 XM_291725 | CAF21722.1 XP_291725.2 | | |
| unnamed protein product | Homo sapiens | n.d. | AK021929 AX881696 | BAB13940.1 CAE91353.1 | Q9HAA9 | |
| Gal β-1,3/4-GlcNAc α- | Mesocricetus | 2.4.99.6 | AJ245699 | CAB53394.1 | Q9QXF6 | |

FIGURE 7F

| Protein | Organism | EC# | GenBank / GenPept | | SwissProt | PDB / 3D |
|---|---|---|---|---|---|---|
| 2,3-sialyltransferase (ST3Gal III) | auratus | | | | | |
| Gal β-1,3/4-GlcNAc α-2,3-sialyltransferase (ST3Gal IV) | Mesocricetus auratus | 2.4.99.6 | AJ245700 | CAB53395.1 | Q9QXF5 | |
| GD3 synthase (fragment) ST8Sia I | Mesocricetus auratus | n.d. | AF141657 | AAD33879.1 | Q9WUL1 | |
| polysialyltransferase (ST8Sia IV) | Mesocricetus auratus | 2.4.99.- | AJ245701 | CAB53396.1 | Q9QXF4 | |
| α-2,3-sialyltransferase ST3Gal I | St3gal1 | Mus musculus | 2.4.99.4 | AF214028<br>AK031344<br>AK078469<br>X73523<br>NM_009177 | AAF60973.1<br>BAC27356.1<br>BAC37290.1<br>CAA51919.1<br>NP_033203.1 | P54751<br>Q11202<br>Q9JL30 |
| α-2,3-sialyltransferase ST3Gal II | St3gal2 | Mus musculus | 2.4.99.4 | BC015264<br>BC066064<br>AK034554<br>AK034863<br>AK053827<br>X76989<br>NM_009179<br>NM_178048 | AAH15264.1<br>AAH66064.1<br>BAC28752.1<br>BAC28859.1<br>BAC35543.1<br>CAA54294.1<br>NP_033205.1<br>NP_835149.1 | Q11204<br>Q8BPL0<br>Q8BSA0<br>Q8BSE9<br>Q91WH6 |
| α-2,3-sialyltransferase ST3Gal III | St3gal3 | Mus musculus | 2.4.99.- | BC006710<br>AK005053<br>AK013016<br>X84234<br>NM_009176 | AAH06710.1<br>BAB23779.1<br>BAB28598.1<br>CAA59013.1<br>NP_033202.2 | P97325<br>Q922X5<br>Q9CZ48<br>Q9DBB6 |
| α-2,3-sialyltransferase ST3Gal IV | St3gal4 | Mus musculus | 2.4.99.4 | BC011121<br>BC050773<br>D28941<br>AK008543<br>AB061305<br>X95809<br>NM_009178 | AAH11121.1<br>AAH50773.1<br>BAA06068.1<br>BAB25732.1<br>BAB47508.1<br>CAA65076.1<br>NP_033204.2 | P97354<br>Q61325<br>Q91Y74<br>Q921R5<br>Q9CVE8 |
| α-2,3-sialyltransferase ST3Gal VI | St3gal6 | Mus musculus | 2.4.99.4 | AF119390<br>BC052338<br>AB063326<br>AK033562<br>AK041173<br>NM_018784 | AAD39130.1<br>AAH52338.1<br>BAB79494.1<br>BAC28360.1<br>BAC30851.1<br>NP_061254 | Q80UR7<br>Q8BLV1<br>Q8VIB3<br>Q9WVG2 |
| α-2,6-sialyltransferase ST6GalNAc II | St6galnac2 | Mus musculus | 2.4.99.- | NM_009180<br>BC010208<br>AB027198<br>AK004613<br>X93999<br>X94000<br>NM_009180 | 6677963<br>AAH10208.1<br>BAB00637.1<br>BAB23410.1<br>CAA63821.1<br>CAA63822.1<br>NP_033206.2 | P70277<br>Q9DC24<br>Q9JJM5 |
| α-2,6-sialyltransferase ST6Gal I | St6gal1 | Mus musculus | 2.4.99.1 | -<br>BC027833<br>D16106<br>AK034768<br>AK084124<br>NM_145933 | AAE68031.1<br>AAH27833.1<br>BAA03680.1<br>BAC28828.1<br>BAC39120.1<br>NP_666045.1 | Q64685<br>Q8BM62<br>Q8K1L1 |
| α-2,6-sialyltransferase ST6Gal II | St6gal2 | Mus musculus | n.d. | AK082566<br>AB095093<br>AK129462<br>NM_172829 | BAC38534.1<br>BAC87752.1<br>BAC98272.1<br>NP_766417.1 | Q8BUU4 |
| α-2,6-sialyltransferase ST6GalNAc I | St6galnac1 | Mus musculus | 2.4.99.3 | Y11274<br>NM_011371 | CAA72137.1<br>NP_035501.1 | Q9QZ39<br>Q9JJP5 |
| α-2,6-sialyltransferase ST6GalNAc III | St6galnac3 | Mus musculus | n.d. | BC058387<br>AK034804<br>Y11342<br>Y11343 | AAH58387.1<br>BAC28836.1<br>CAA72181.2<br>CAB95031.1 | Q9WUV2<br>Q9JHP5 |

FIGURE 7G

| Protein | Organism | EC# | GenBank / GenPept | | SwissProt | PDB / 3D |
|---|---|---|---|---|---|---|
| | | | NM_011372 | NP_035502 | | |
| α-2,6-sialyltransferase ST6GalNAc IV | St6galnac4 | Mus musculus | 2.4.99.7 | BC056451 | AAH56451.1 | Q8C3J2 | |
| | | | AK085730 | BAC39523.1 | Q9JHP2 | |
| | | | AJ007310 | CAA07446.1 | Q9R2B6 | |
| | | | Y15779 | CAB43507.1 | O88725 | |
| | | | Y15780 | CAB43514.1 | Q9JHP0 | |
| | | | Y19055 | CAB93946.1 | Q9QUP9 | |
| | | | Y19057 | CAB93948.1 | Q9R2B5 | |
| | | | NM_011373 | NP_035503.1 | | |
| α-2,8-sialyltransferase (GD3 synthase) ST8Sia I | St8sia1 | Mus musculus | 2.4.99.8 | L38677 | AAA91869.1 | Q64468 | |
| | | | BC024821 | AAH24821.1 | Q64687 | |
| | | | AK046188 | BAC32625.1 | Q8BL76 | |
| | | | AK052444 | BAC34994.1 | Q8BWI0 | |
| | | | X84235 | CAA59014.1 | Q8K1C1 | |
| | | | AJ401102 | CAC20706.1 | Q9EPK0 | |
| | | | NM_011374 | NP_035504.1 | | |
| α-2,8-sialyltransferase (ST8Sia VI) | St8sia6 | Mus musculus | n.d. | AB059554 | BAC01265.1 | Q8BI43 | |
| | | | AK085105 | BAC39367.1 | Q8K4T1 | |
| | | | NM_145838 | NP_665837.1 | | |
| α-2,8-sialyltransferase ST8Sia II | St8sia2 | Mus musculus | 2.4.99.- | X83562 | CAA58548.1 | O35696 | |
| | | | X99646 | CAA67965.1 | | |
| | | | X99647 | CAA67965.1 | | |
| | | | X99648 | CAA67965.1 | | |
| | | | X99649 | CAA67965.1 | | |
| | | | X99650 | CAA67965.1 | | |
| | | | X99651 | CAA67965.1 | | |
| | | | NM_009181 | NP_033207.1 | | |
| α-2,8-sialyltransferase ST8Sia IV | St8sia4 | Mus musculus | 2.4.99.8 | BC060112 | AAH60112.1 | Q64692 | |
| | | | AK003690 | BAB22941.1 | Q8BY70 | |
| | | | AK041723 | BAC31044.1 | | |
| | | | AJ223956 | CAA11685.1 | | |
| | | | X86000 | CAA59992.1 | | |
| | | | Y09484 | CAA70692.1 | | |
| | | | NM_009183 | NP_033209.1 | | |
| α-2,8-sialyltransferase ST8Sia V | St8sia5 | Mus musculus | 2.4.99.- | BC034855 | AAH34855.1 | P70126 | |
| | | | AK078670 | BAC37354.1 | P70127 | |
| | | | X98014 | CAA66642.1 | P70128 | |
| | | | X98014 | CAA66643.1 | Q8BJW0 | |
| | | | X98014 | CAA66644.1 | Q8JZQ3 | |
| | | | NM_013666 | NP_038694.1 | | |
| | | | NM_153124 | NP_694764.1 | | |
| | | | NM_177416 | NP_803135.1 | | |
| α-2,8-sialytransferase ST8Sia III | St8sia3 | Mus musculus | 2.4.99.- | BC075645 | AAH75645.1 | Q64689 | |
| | | | AK015874 | BAB30012.1 | Q9CUJ6 | |
| | | | X80502 | CAA56665.1 | | |
| | | | NM_009182 | NP_033208.1 | | |
| GD1 synthase (ST6GalNAc V) | St6galnac5 | Mus musculus | n.d. | BC055737 | AAH55737.1 | Q8CAM7 | |
| | | | AB030836 | BAA85747.1 | Q8CBX1 | |
| | | | AB028840 | BAA89292.1 | Q9QYJ1 | |
| | | | AK034387 | BAC28693.1 | Q9R0K6 | |
| | | | AK038434 | BAC29997.1 | | |
| | | | AK042683 | BAC31331.1 | | |
| | | | NM_012028 | NP_036158.2 | | |
| GM3 synthase (α-2,3-sialyltransferase) ST3Gal V | St3gal5 | Mus musculus | 2.4.99.9 | AF119416 | AAF66147.1 | O88829 | |
| | | | - | AAP65063.1 | Q9CZ65 | |
| | | | AB018048 | BAA33491.1 | Q9QWF9 | |
| | | | AB013302 | BAA76467.1 | | |
| | | | AK012961 | BAB28571.1 | | |
| | | | Y15003 | CAA75235.1 | | |
| | | | NM_011375 | NP_035505.1 | | |
| N-acetylgalactosaminide α-2,6-sialyltransferase (ST6GalNAc VI) | St6galnac6 | Mus musculus | 2.4.99.- | BC036985 | AAH36985.1 | Q8CDC3 | |
| | | | AB035174 | BAA87036.1 | Q8JZW3 | |
| | | | AB035123 | BAA95940.1 | Q9JM95 | |
| | | | AK030648 | BAC27064.1 | Q9R0G9 | |

FIGURE 7H

| Protein | Organism | EC# | GenBank / GenPept | | SwissProt | PDB / 3D |
|---|---|---|---|---|---|---|
| | | | NM_016973 | NP_058669.1 | | |
| M138L | Myxoma virus | n.d. | U46578<br>AF170726<br>NC_001132 | AAD00069.1<br>AAE61323.1<br>AAE61326.1<br>AAF15026.1<br>NP_051852.1 | | |
| α-2,3-sialyltransferase (St3Gal-I) | Oncorhynchus mykiss | n.d. | AJ585760 | CAE51384.1 | | |
| α-2,6-sialyltransferase (Siat1) | Oncorhynchus mykiss | n.d. | AJ620649 | CAF05848.1 | | |
| α-2,8-polysialyltransferase IV (ST8Sia IV) | Oncorhynchus mykiss | n.d. | AB094402 | BAC77411.1 | Q7T2X5 | |
| GalNAc α-2,6-sialyltransferase (RtST6GalNAc) | Oncorhynchus mykiss | n.d. | AB097943 | BAC77520.1 | Q7T2X4 | |
| α-2,3-sialyltransferase ST3Gal IV | Oryctolagus cuniculus | 2.4.99.- | AF121967 | AAF28871.1 | Q9N257 | |
| OJ1217_F02.7 | Oryza sativa (japonica cultivar-group) | n.d. | AP004084 | BAD07616.1 | | |
| OSJNBa0043L24.2 or OSJNBb0002J11.9 | Oryza sativa (japonica cultivar-group) | n.d. | AL731626<br>AL662969 | CAD41185.1<br>CAE04714.1 | | |
| P0683f02.18 or P0489B03.1 | Oryza sativa (japonica cultivar-group) | n.d. | AP003289<br>AP003794 | BAB63715.1<br>BAB90552.1 | | |
| α-2,6-sialyltransferase ST6GalNAc V (Siat7E) (fragment) | Oryzias latipes | n.d. | AJ646876 | CAG26705.1 | | |
| α-2,3-sialyltransferase ST3Gal I (Siat4) | Pan troglodytes | n.d. | AJ744803 | CAG32839.1 | | |
| α-2,3-sialyltransferase ST3Gal II (Siat5) | Pan troglodytes | n.d. | AJ744804 | CAG32840.1 | | |
| α-2,3-sialyltransferase ST3Gal III (Siat6) | Pan troglodytes | n.d. | AJ626819 | CAF25177.1 | | |
| α-2,3-sialyltransferase ST3Gal IV (Siat4c) | Pan troglodytes | n.d. | AJ626824 | CAF25182.1 | | |
| α-2,3-sialyltransferase ST3Gal VI (Siat10) | Pan troglodytes | n.d. | AJ744808 | CAG32844.1 | | |
| α-2,6-sialyltransferase (Sia7A) | Pan troglodytes | n.d. | AJ748740 | CAG38615.1 | | |
| α-2,6-sialyltransferase (Sia7B) | Pan troglodytes | n.d. | AJ748741 | CAG38616.1 | | |
| α-2,6-sialyltransferase ST6GalNAc III (Siat7C) | Pan troglodytes | n.d. | AJ634454 | CAG25676.1 | | |
| α-2,6-sialyltransferase ST6GalNAc IV (Siat7D) (fragment) | Pan troglodytes | n.d. | AJ646870 | CAG26699.1 | | |
| α-2,6-sialyltransferase ST6GalNAc V (Siat7E) | Pan troglodytes | n.d. | AJ646875 | CAG26704.1 | | |
| α-2,6-sialyltransferase ST6GalNAc VI (Siat7F) (fragment) | Pan troglodytes | n.d. | AJ646882 | CAG26711.1 | | |
| α-2,8-sialyltransferase 8A (Siat8A) | Pan troglodytes | 2.4.99.8 | AJ697658 | CAG26896.1 | | |
| α-2,8-sialyltransferase 8B (Siat8B) | Pan troglodytes | n.d. | AJ697659 | CAG26897.1 | | |
| α-2,8-sialyltransferase 8C (Siat8C) | Pan troglodytes | n.d. | AJ697660 | CAG26898.1 | | |
| α-2,8-sialyltransferase 8D (Siat8D) | Pan troglodytes | n.d. | AJ697661 | CAG26899.1 | | |
| α-2,8-sialyltransferase | Pan troglodytes | n.d. | AJ697662 | CAG26900.1 | | |

FIGURE 7I

| Protein | Organism | EC# | GenBank / GenPept | | SwissProt | PDB / 3D |
|---|---|---|---|---|---|---|
| 8E (Siat8E) | | | | | | |
| α-2,8-sialyltransferase 8F (Siat8F) | Pan troglodytes | n.d. | AJ697663 | CAG26901.1 | | |
| β-galactosamide α-2,6-sialyltransferase I (ST6Gal I; Siat1) | Pan troglodytes | 2.4.99.1 | AJ627624 | CAF29492.1 | | |
| β-galactosamide α-2,6-sialyltransferase II (ST6Gal II) | Pan troglodytes | n.d. | AJ627625 | CAF29493.1 | | |
| GM3 synthase ST3Gal V (Siat9) | Pan troglodytes | n.d. | AJ744807 | CAG32843.1 | | |
| S138L | Rabbit fibroma virus Kasza | n.d. | NC_001266 | NP_052025 | | |
| α-2,3-sialyltransferase ST3Gal III | Rattus norvegicus | 2.4.99.6 | M97754 NM_031697 | AAA42146.1 NP_113885.1 | Q02734 | |
| α-2,3-sialyltransferase ST3Gal IV (Siat4c) | Rattus norvegicus | n.d. | AJ626825 | CAF25183.1 | | |
| α-2,3-sialyltransferase ST3Gal VI | Rattus norvegicus | n.d. | AJ626743 | CAF25053.1 | | |
| α-2,6-sialyltransferase ST3Gal II | Rattus norvegicus | 2.4.99.- | X76988 NM_031695 | CAA54293.1 NP_113883.1 | Q11205 | |
| α-2,6-sialyltransferase ST6Gal I | Rattus norvegicus | 2.4.99.1 | M18769 M83143 | AAA41196.1 AAB07233.1 | P13721 | |
| α-2,6-sialyltransferase ST6GalNAc I (Siat7A) | Rattus norvegicus | n.d. | AJ634458 | CAG25684.1 | | |
| α-2,6-sialyltransferase ST6GalNAc II (Siat7B) | Rattus norvegicus | n.d. | AJ634457 | CAG25679.1 | | |
| α-2,6-sialyltransferase ST6GalNAc III | Rattus norvegicus | 2.4.99.- | L29554 BC072501 NM_019123 | AAC42086.1 AAH72501.1 NP_061996.1 | Q64686 | |
| α-2,6-sialyltransferase ST6GalNAc IV (Siat7D) (fragment) | Rattus norvegicus | n.d. | AJ646871 | CAG26700.1 | | |
| α-2,6-sialyltransferase ST6GalNAc V (Siat7E) | Rattus norvegicus | n.d. | AJ646872 | CAG26701.1 | | |
| α-2,6-sialyltransferase ST6GalNAc VI (Siat7F) (fragment) | Rattus norvegicus | n.d. | AJ646881 | CAG26710.1 | | |
| α-2,8-sialyltransferase (GD3 synthase) ST8Sia I | Rattus norvegicus | 2.4.99.- | U53883 D45255 | AAC27541.1 BAA08213.1 | P70554 P97713 | |
| α-2,8-sialyltransferase (SIAT8E) | Rattus norvegicus | n.d. | AJ699422 | CAG27884.1 | | |
| α-2,8-sialyltransferase (SIAT8F) | Rattus norvegicus | n.d. | AJ699423 | CAG27885.1 | | |
| α-2,8-sialyltransferase ST8Sia II | Rattus norvegicus | 2.4.99.- | L13445 NM_057156 | AAA42147.1 NP_476497.1 | Q07977 Q64688 | |
| α-2,8-sialyltransferase ST8Sia III | Rattus norvegicus | 2.4.99.- | U55938 NM_013029 | AAB50061.1 NP_037161.1 | P97877 | |
| α-2,8-sialyltransferase ST8Sia IV | Rattus norvegicus | 2.4.99.- | U90215 | AAB49989.1 | O08563 | |
| β-galactosamide α-2,6-sialyltransferase II (ST6Gal II) | Rattus norvegicus | n.d. | AJ627626 | CAF29494.1 | | |
| GM3 synthase ST3Gal V | Rattus norvegicus | n.d. | AB018049 NM_031337 | BAA33492.1 NP_112627.1 | O88830 | |

FIGURE 7J

| Protein | Organism | EC# | GenBank / GenPept | | SwissProt | PDB / 3D |
|---|---|---|---|---|---|---|
| sialyltransferase ST3Gal-I (Siat4A) | Rattus norvegicus | n.d. | AJ748840 | CAG44449.1 | | |
| α-2,3-sialyltransferase (St3Gal-II) | Silurana tropicalis | n.d. | AJ585763 | CAE51387.1 | | |
| α-2,6-sialyltransferase (Siat7b) | Silurana tropicalis | n.d. | AJ620650 | CAF05849.1 | | |
| α-2,6-sialyltransferase (St6galnac) | Strongylocentrotus purpuratus | n.d. | AJ699425 | CAG27887.1 | | |
| α-2,3-sialyltransferase (ST3GAL-III) | Sus scrofa | n.d. | AJ585765 | CAE51389.1 | | |
| α-2,3-sialyltransferase (ST3GAL-IV) | Sus scrofa | n.d. | AJ584674 | CAE48299.1 | | |
| α-2,3-sialyltransferase ST3Gal I | Sus scrofa | 2.4.99.4 | M97753 | AAA31125.1 | Q02745 | |
| α-2,6-sialyltransferase (fragment) ST6Gal I | Sus scrofa | 2.4.99.1 | AF136746 | AAD33059.1 | Q9XSG8 | |
| β-galactosamide α-2,6-sialyltransferase (ST6GalNAc-V) | Sus scrofa | n.d. | AJ620948 | CAF06585.2 | | |
| sialyltransferase (fragment) ST6Gal I | sus scrofa | n.d. | AF041031 | AAC15633.1 | O62717 | |
| ST6GALNAC-V | Sus scrofa | n.d. | AJ620948 | CAF06585.1 | | |
| α-2,3-sialyltransferase (Siat5-r) | Takifugu rubripes | n.d. | AJ744805 | CAG32841.1 | | |
| α-2,3-sialyltransferase ST3Gal I (Siat4) | Takifugu rubripes | n.d. | AJ626816 | CAF25174.1 | | |
| α-2,3-sialyltransferase ST3Gal II (Siat5) (fragment) | Takifugu rubripes | n.d. | AJ626817 | CAF25175.1 | | |
| α-2,3-sialyltransferase ST3Gal III (Siat6) | Takifugu rubripes | n.d. | AJ626818 | CAF25176.1 | | |
| α-2,6-sialyltransferase ST6Gal I (Siat1) | Takifugu rubripes | n.d. | AJ744800 | CAG32836.1 | | |
| α-2,6-sialyltransferase ST6GalNAc II (Siat7B) | Takifugu rubripes | n.d. | AJ634460 | CAG25681.1 | | |
| α-2,6-sialyltransferase ST6GalNAc II B (Siat7B-related) | Takifugu rubripes | n.d. | AJ634461 | CAG25682.1 | | |
| α-2,6-sialyltransferase ST6GalNAc III (Siat7C) (fragment) | Takifugu rubripes | n.d. | AJ634456 | CAG25678.1 | | |
| α-2,6-sialyltransferase ST6GalNAc IV (siat7D) (fragment) | Takifugu rubripes | 2.4.99.3 | Y17466 AJ646869 | CAB44338.1 CAG26698.1 | Q9W6U6 | |
| α-2,6-sialyltransferase ST6GalNAc V (Siat7E) (fragment) | Takifugu rubripes | n.d. | AJ646873 | CAG26702.1 | | |
| α-2,6-sialyltransferase ST6GalNAc VI (Siat7F) (fragment) | Takifugu rubripes | n.d. | AJ646880 | CAG26709.1 | | |
| α-2,8-sialyltransferase ST8Sia I (Siat 8A) (fragment) | Takifugu rubripes | n.d. | AJ715534 | CAG29373.1 | | |
| α-2,8-sialyltransferase ST8Sia II (Siat 8B) (fragment) | Takifugu rubripes | n.d. | AJ715538 | CAG29377.1 | | |
| α-2,8-sialyltransferase ST8Sia III (Siat 8C) (fragment) | Takifugu rubripes | n.d. | AJ715541 | CAG29380.1 | | |
| α-2,8-sialyltransferase ST8Sia IIIr (Siat 8Cr) | Takifugu rubripes | n.d. | AJ715542 | CAG29381.1 | | |
| α-2,8-sialyltransferase ST8Sia V (Siat 8E) | Takifugu rubripes | n.d. | AJ715547 | CAG29386.1 | | |

FIGURE 7K

| Protein | Organism | EC# | GenBank / GenPept | | SwissProt | PDB / 3D |
|---|---|---|---|---|---|---|
| (fragment) | | | | | | |
| α-2,8-sialyltransferase ST8Sia VI (Siat 8F) (fragment) | Takifugu rubripes | n.d. | AJ715549 | CAG29388.1 | | |
| α-2,8-sialyltransferase ST8Sia VIr (Siat 8Fr) | Takifugu rubripes | n.d. | AJ715550 | CAG29389.1 | | |
| α-2,3-sialyltransferase (Siat5-r) | Tetraodon nigroviridis | n.d. | AJ744806 | CAG32842.1 | | |
| α-2,3-sialyltransferase ST3Gal I (Siat4) | Tetraodon nigroviridis | n.d. | AJ744802 | CAG32838.1 | | |
| α-2,3-sialyltransferase ST3Gal III (Siat6) | Tetraodon nigroviridis | n.d. | AJ626822 | CAF25180.1 | | |
| α-2,6-sialyltransferase ST6GalNAc II (Siat7B) | Tetraodon nigroviridis | n.d. | AJ634462 | CAG25683.1 | | |
| α-2,6-sialyltransferase ST6GalNAc V (Siat7E) (fragment) | Tetraodon nigroviridis | n.d. | AJ646879 | CAG26708.1 | | |
| α-2,8-sialyltransferase ST8Sia I (Siat 8A) (fragment) | Tetraodon nigroviridis | n.d. | AJ715536 | CAG29375.1 | | |
| α-2,8-sialyltransferase ST8Sia II (Siat 8B) (fragment) | Tetraodon nigroviridis | n.d. | AJ715537 | CAG29376.1 | | |
| α-2,8-sialyltransferase ST8Sia III (Siat 8C) (fragment) | Tetraodon nigroviridis | n.d. | AJ715539 | CAG29378.1 | | |
| α-2,8-sialyltransferase ST8Sia IIIr (Siat 8Cr) (fragment) | Tetraodon nigroviridis | n.d. | AJ715540 | CAG29379.1 | | |
| α-2,8-sialyltransferase ST8Sia V (Siat 8E) (fragment) | Tetraodon nigroviridis | n.d. | AJ715548 | CAG29387.1 | | |
| α-2,3-sialyltransferase (St3Gal-II) | Xenopus laevis | n.d. | AJ585762 | CAE51386.1 | | |
| α-2,3-sialyltransferase (St3Gal-VI) | Xenopus laevis | n.d. | AJ585766 | CAE51390.1 | | |
| α-2,3-sialyltransferase St3Gal-III (Siat6) | Xenopus laevis | n.d. | AJ585764 AJ626823 | CAE51388.1 CAF25181.1 | | |
| α-2,8-polysialyltransferase | Xenopus laevis | 2.4.99.- | AB007468 | BAA32617.1 | O93234 | |
| α-2,8-sialyltransferase ST8Siα-I (Siat8A;GD3 synthase) | Xenopus laevis | n.d. | AY272056 AY272057 AJ704562 | AAQ16162.1 AAQ16163.1 CAG28695.1 | | |
| Unknown (protein for MGC:81265) | Xenopus laevis | n.d. | BC068760 | AAH68760.1 | | |
| α-2,3-sialyltransferase (3Gal-VI) | Xenopus tropicalis | n.d. | AJ626744 | CAF25054.1 | | |
| α-2,3-sialyltransferase (Siat4c) | Xenopus tropicalis | n.d. | AJ622908 | CAF22058.1 | | |
| α-2,6-sialyltransferase ST6GalNAc V (Siat7E) (fragment) | Xenopus tropicalis | n.d. | AJ646878 | CAG26707.1 | | |
| α-2,8-sialyltransferase ST8Sia III (Siat 8C) (fragment) | Xenopus tropicalis | n.d. | AJ715544 | CAG29383.1 | | |
| β-galactosamide α-2,6-sialyltransferase II (ST6Gal II) | Xenopus tropicalis | n.d. | AJ627628 | CAF29496.1 | | |
| sialytransferase St8Sial | Xenopus tropicalis | n.d. | AY652775 | AAT67042 | | |
| poly-α-2,8-sialosyl sialyltransferase (NeuS) | Escherichia coli K1 | 2.4.-.- | M76370 X60598 | AAA24213.1 CAA43053.1 | Q57269 | |
| polysialyltransferase | Escherichia coli K92 | 2.4.-.- | M88479 | AAA24215.1 | Q47404 | |

FIGURE 7L

| Protein | Organism | EC# | GenBank / GenPept | | SwissProt | PDB / 3D |
|---|---|---|---|---|---|---|
| α-2,8 polysialyltransferase SiaD | Neisseria meningitidis B1940 | 2.4.-.- | M95053 X78068 | AAA20478.1 CAA54985.1 | Q51281 Q51145 | |
| SynE | Neisseria meningitidis FAM18 | n.d. | U75650 | AAB53842.1 | O06435 | |
| polysialyltransferase (SiaD)(fragment) | Neisseria meningitidis M1019 | n.d. | AY234192 | AAO85290.1 | | |
| SiaD (fragment) | Neisseria meningitidis M209 | n.d. | AY281046 | AAP34769.1 | | |
| SiaD (fragment) | Neisseria meningitidis M3045 | n.d. | AY281044 | AAP34767.1 | | |
| polysialyltransferase (SiaD)(fragment) | Neisseria meningitidis M3315 | n.d. | AY234191 | AAO85289.1 | | |
| SiaD (fragment) | Neisseria meningitidis M3515 | n.d. | AY281047 | AAP34770.1 | | |
| polysialyltransferase (SiaD)(fragment) | Neisseria meningitidis M4211 | n.d. | AY234190 | AAO85288.1 | | |
| SiaD (fragment) | Neisseria meningitidis M4642 | n.d. | AY281048 | AAP34771.1 | | |
| polysialyltransferase (SiaD)(fragment) | Neisseria meningitidis M5177 | n.d. | AY234193 | AAO85291.1 | | |
| SiaD | Neisseria meningitidis M5178 | n.d. | AY281043 | AAP34766.1 | | |
| SiaD (fragment) | Neisseria meningitidis M980 | n.d. | AY281045 | AAP34768.1 | | |
| NMB0067 | Neisseria meningitidis MC58 | n.d. | NC_003112 | NP_273131 | | |
| Lst | Aeromonas punctata Sch3 | n.d. | AF126256 | AAS66624.1 | | |
| ORF2 | Haemophilus influenzae A2 | n.d. | M94855 | AAA24979.1 | | |
| HI1699 | Haemophilus influenzae Rd | n.d. | U32842 NC_000907 | AAC23345.1 NP_439841.1 | Q48211 | |
| α-2,3-sialyltransferase | Neisseria gonorrhoeae F62 | 2.4.99.4 | U60664 | AAC44539.1 AAE67205.1 | P72074 | |
| α-2,3-sialyltransferase | Neisseria meningitidis 126E, NRCC 4010 | 2.4.99.4 | U60662 | AAC44544.2 | | |
| α-2,3-sialyltransferase | Neisseria meningitidis 406Y, NRCC 4030 | 2.4.99.4 | U60661 | AAC44543.1 | | |
| α-2,3-sialyltransferase (NMB0922) | Neisseria meningitidis MC58 | 2.4.99.4 | U60660 AE002443 NC_003112 | AAC44541.1 AAF41330.1 NP_273962.1 | P72097 | |
| NMA1118 | Neisseria meningitidis Z2491 | n.d. | AL162755 NC_003116 | CAB84380.1 NP_283887.1 | Q9JUV5 | |
| PM0508 | Pasteurella multocida PM70 | n.d. | AE006086 NC_002663 | AAK02592.1 NP_245445.1 | Q9CNC4 | |
| WaaH | Salmonella enterica SARB25 | n.d. | AF519787 | AAM82550.1 | Q8KS93 | |
| WaaH | Salmonella enterica SARB3 | n.d. | AF519788 | AAM82551.1 | Q8KS92 | |
| WaaH | Salmonella enterica SARB39 | n.d. | AF519789 | AAM82552.1 | | |
| WaaH | Salmonella enterica SARB53 | n.d. | AF519790 | AAM82553.1 | | |
| WaaH | Salmonella enterica SARB57 | n.d. | AF519791 | AAM82554.1 | Q8KS91 | |
| WaaH | Salmonella enterica SARB71 | n.d. | AF519793 | AAM82556.1 | Q8KS89 | |
| WaaH | Salmonella enterica | n.d. | AF519792 | AAM82555.1 | Q8KS90 | |

FIGURE 7M

| Protein | Organism | EC# | GenBank / GenPept | | SwissProt | PDB / 3D |
|---|---|---|---|---|---|---|
| | SARB8 | | | | | |
| WaaH | Salmonella enterica SARC10V | n.d. | AF519779 | AAM88840.1 | Q8KS99 | |
| WaaH (fragment) | Salmonella enterica SARC12 | n.d. | AF519781 | AAM88842.1 | | |
| WaaH (fragment) | Salmonella enterica SARC13I | n.d. | AF519782 | AAM88843.1 | Q8KS98 | |
| WaaH (fragment) | Salmonella enterica SARC14I | n.d. | AF519783 | AAM88844.1 | Q8KS97 | |
| WaaH | Salmonella enterica SARC15II | n.d. | AF519784 | AAM88845.1 | Q8KS96 | |
| WaaH | Salmonella enterica SARC16II | n.d. | AF519785 | AAM88846.1 | Q8KS95 | |
| WaaH (fragment) | Salmonella enterica SARC3I | n.d. | AF519772 | AAM88834.1 | Q8KSA4 | |
| WaaH (fragment) | Salmonella enterica SARC4I | n.d. | AF519773 | AAM88835.1 | Q8KSA3 | |
| WaaH | Salmonella enterica SARC5IIa | n.d. | AF519774 | AAM88836.1 | | |
| WaaH | Salmonella enterica SARC6IIa | n.d. | AF519775 | AAM88837.1 | Q8KSA2 | |
| WaaH | Salmonella enterica SARC8 | n.d. | AF519777 | AAM88838.1 | Q8KSA1 | |
| WaaH | Salmonella enterica SARC9V | n.d. | AF519778 | AAM88839.1 | Q8KSA0 | |
| UDP-glucose : α-1,2-glucosyltransferase (WaaH) | Salmonella enterica subsp. arizonae SARC 5 | 2.4.1.- | AF511116 | AAM48166.1 | | |
| bifunctional α-2,3/-2,8-sialyltransferase (Cst-II) | Campylobacter jejuni ATCC 43449 | n.d. | AF401529 | AAL06004.1 | Q93CZ5 | |
| Cst | Campylobacter jejuni 81-176 | n.d. | AF305571 | AAL09368.1 | | |
| α-2,3-sialyltransferase (Cst-III) | Campylobacter jejuni ATCC 43429 | 2.4.99.- | AY044156 | AAK73183.1 | | |
| α-2,3-sialyltransferase (Cst-III) | Campylobacter jejuni ATCC 43430 | 2.4.99.- | AF400047 | AAK85419.1 | | |
| α-2,3-sialyltransferase (Cst-II) | Campylobacter jejuni ATCC 43432 | 2.4.99.- | AF215659 | AAG43979.1 | Q9F0M9 | |
| α-2,3/8-sialyltransferase (CstII) | Campylobacter jejuni ATCC 43438 | n.d. | AF400048 | AAK91725.1 | Q93MQ0 | |
| α-2,3-sialyltransferase cst-II | Campylobacter jejuni ATCC 43446 | 2.4.99.- | AF167344 | AAF34137.1 | | |
| α-2,3-sialyltransferase (Cst-II) | Campylobacter jejuni ATCC 43456 | 2.4.99.- | AF401528 | AAL05990.1 | Q93D05 | |
| α-2,3-/α-2,8-sialyltransferase (CstII) | Campylobacter jejuni ATCC 43460 | 2.4.99.- | AY044868 | AAK96001.1 | Q938X6 | |
| α-2,3/8-sialyltransferase (Cst-II) | Campylobacter jejuni ATCC 700297 | n.d. | AF216647 | AAL36462.1 | | |
| ORF | Campylobacter jejuni GB11 | n.d. | AY422197 | AAR82875.1 | | |
| α-2,3-sialyltransferase cstIII | Campylobacter jejuni MSC57360 | 2.4.99.- | AF195055 | AAG29922.1 | | |
| α-2,3-sialyltransferase cstIII Cj1140 | Campylobacter jejuni NCTC 11168 | 2.4.99.- | AL139077 NC_002163 | CAB73395.1 NP_282288.1 | Q9PNF4 | |
| α-2,3/α-2,8-sialyltransferase II (cstII) | Campylobacter jejuni O:10 | n.d. | - AX934427 | AAO96669.1 CAF04167.1 | | |
| α-2,3/α-2,8-sialyltransferase II (CstII) | Campylobacter jejuni O:19 | n.d. | AX934431 | CAF04169.1 | | |
| α-2,3/α-2,8-sialyltransferase II (CstII) | Campylobacter jejuni O:36 | n.d. | AX934436 | CAF04171.1 | | |
| α-2,3/α-2,8- | Campylobacter | n.d. | AX934434 | CAF04170.1 | | |

FIGURE 7N

| Protein | Organism | EC# | GenBank / GenPept | | SwissProt | PDB / 3D | |
|---|---|---|---|---|---|---|---|
| sialyltransferase II (CstII) | jejuni O:4 | | | | | | |
| α-2,3/α-2,8-sialyltransferase II (CstII) | Campylobacter jejuni O:41 | n.d. | -<br>AX934429 | AAO96670.1<br>AAT17967.1<br>CAF04168.1 | | | |
| α-2,3-sialyltransferase cst-I | Campylobacter jejuni OH4384 | 2.4.99.- | AF130466<br>- | AAF13495.1<br>AAS36261.1 | Q9RGF1 | | |
| bifunctional α-2,3/-2,8-sialyltransferase (Cst-II) | Campylobacter jejuni OH4384 | 2.4.99.- | AF130984<br>AX934425 | AAF31771.1<br>CAF04166.1 | | 1RO7<br>1RO8 | C<br>A |
| HI0352 (fragment) | Haemophilus influenzae Rd | n.d. | U32720<br>X57315<br>NC_000907 | AAC22013.1<br>CAA40567.1<br>NP_438516.1 | P24324 | | |
| PM1174 | Pasteurella multocida PM70 | n.d. | AE006157<br>NC_002663 | AAK03258.1<br>NP_246111.1 | Q9CLP3 | | |
| Sequence 10 from patent US 6503744 | Unknown. | n.d. | - | AAO96672.1 | | | |
| Sequence 10 from patent US 6699705 | Unknown. | n.d. | - | AAT17969.1 | | | |
| Sequence 12 from patent US 6699705 | Unknown. | n.d. | - | AAT17970.1 | | | |
| Sequence 2 from patent US 6709834 | Unknown. | n.d. | - | AAT23232.1 | | | |
| Sequence 3 from patent US 6503744 | Unknown. | n.d. | - | AAO96668.1 | | | |
| Sequence 3 from patent US 6699705 | Unknown. | n.d. | - | AAT17965.1 | | | |
| Sequence 34 from patent US 6503744 | Unknown. | n.d. | - | AAO96684.1 | | | |
| Sequence 35 from patent US 6503744 (fragment) | Unknown. | n.d. | - | AAO96685.1<br>AAS36262.1 | | | |
| Sequence 48 from patent US 6699705 | Unknown. | n.d. | - | AAT17988.1 | | | |
| Sequence 5 from patent US 6699705 | Unknown. | n.d. | - | AAT17966.1 | | | |
| Sequence 9 from patent US 6503744 | Unknown. | n.d. | - | AAO96671.1 | | | |

NUCLEOTIDE SUGAR PURIFICATION USING MEMBRANES

CROSS-REFERENCE TO RELATED APPLICATIONS

The present application is a divisional of copending U.S. patent application Ser. No. 12/092,563 filed Jun. 18, 2008 which represents the U.S. national phase application of International Patent Application PCT/US2006/043048 filed Nov. 3, 2006, which claims the benefit of U.S. Provisional Patent Application No. 60/829,242, filed Oct. 12, 2006, U.S. Provisional Patent Application No. 60/823,538, filed Aug. 25, 2006, U.S. Provisional Patent Application No. 60/746,754, filed May 8, 2006, U.S. Provisional Patent Application No. 60/796,281, filed Apr. 28, 2006, and U.S. Provisional Patent Application No. 60/733,975, filed Nov. 3, 2005, all of which are incorporated herein by reference for all purposes.

BACKGROUND OF THE INVENTION

Increased understanding of the role of carbohydrates as recognition elements on the surface of cells has led to increased interest in the production of carbohydrate molecules of defined structure. For instance, compounds comprising the oligosaccharide moiety, sialyl lactose, have been of interest as neutralizers for enterotoxins from bacteria such as *Vibrio cholerae, Escherichia coli*, and *Salmonella* (see, e.g., U.S. Pat. No. 5,330,975). Sialyl lactose has also been investigated for the treatment of arthritis and related autoimmune diseases. In particular, sialyl lactose is thought to inhibit or disrupt the degree of occupancy of the Fc carbohydrate binding site on IgG, and thus prevent the formation of immune complexes (see, U.S. Pat. No. 5,164,374). Recently, sialyl-α(2,3)galactosides, sialyl lactose and sialyl lactosamine have been proposed for the treatment of ulcers, and Phase I clinical trials have begun for the use of the former compound in this capacity. See, Balkonen et al., *FEMS Immunology and Medical Microbiology* 7:29 (1993) and BioWorld Today, p. 5, Apr. 4, 1995. As another example, compounds comprising the sialyl Lewis ligands, sialyl Lewis$^x$ and sialyl Lewis$^a$ are present in leukocyte and non-leukocyte cell lines that bind to receptors such as the ELAM-1 and GMP 140 receptors. Polley et al., *Proc. Natl. Acad. Sci., USA,* 88:6224 (1991) and Phillips et al., *Science,* 250:1130 (1990), see, also, U.S. Ser. No. 08/063,181.

Because of interest in making desired carbohydrate structures, glycosyltransferases and their role in enzyme-catalyzed synthesis of carbohydrates are presently being extensively studied. The use of glycosyltransferases for enzymatic synthesis of carbohydrate offers advantages over chemical methods due to the virtually complete stereoselectivity and linkage specificity offered by the enzymes (Ito et al., *Pure Appl. Chem.,* 65:753 (1993) U.S. Pat. Nos. 5,352,670, and 5,374,541). Consequently, glycosyltransferases are increasingly used as enzymatic catalysts in synthesis of a number of carbohydrates used for therapeutic and other purposes.

Carbohydrate compounds produced by enzymatic synthesis or by other methods are often obtained in the form of complex mixtures that include not only the desired compound but also contaminants such as unreacted sugars, salts, pyruvate, phosphate, PEP, nucleosides, nucleotides, and proteins, among others. The presence of these contaminants is undesirable for many applications for which the carbohydrate compounds are useful. Previously used methods for purifying oligosaccharides, such as chromatography, i.e., ion exchange and size exclusion chromatography, have several disadvantages. For example, chromatographic purification methods are not amenable to large-scale purifications, thus precluding their use for commercial production of saccharides. Moreover, chromatographic purification methods are expensive. Therefore, a need exists for purification methods that are faster, more efficient, and less expensive than previously used methods. The present invention fulfills this and other needs.

SUMMARY OF THE INVENTION

The present invention provides methods of purifying a carbohydrate compound from a feed solution containing a contaminant. The methods involve contacting the feed solution with a nanofiltration or reverse osmosis membrane under conditions such that the membrane retains the desired carbohydrate compound while a majority of the contaminant passes through the membrane. The invention provides methods for purifying carbohydrate compounds such as sialyl lactosides, sialic acid, lacto-N-neotetraose (LNnT) and GlcNAcβ1,3Galβ1,4Glc (LNT-2), NeuAcα(2→3)Galβ(1→4)(Fucα1→3)Glc(R$^1$)β1-OR$^2$, wherein R$^1$ is OH or NAc; R$^2$ is a hydrogen, an alkoxy, a saccharide, an oligosaccharide or an aglycon group having at least one carbon atom; and Galα(1→3)Galβ(1→4)Glc(R$^1$)β-O—R$^3$, wherein R$^1$ is OH or NAc; R$^3$ is —(CH$_2$)$_n$—COX, with X=OH, OR$^4$, —NHNH$_2$, R$^4$ being a hydrogen, a saccharide, an oligosaccharide or an aglycon group having at least one carbon atom, and n=an integer from 2 to 18.

Also provided are methods for purifying carbohydrate compounds having a formula NeuAcα(2→3)Galβ(1→4)GlcN(R$^1$)β-OR$^2$, NeuAcα(2→3)Galβ(1→4)GlcN(R$^1$)β(1→3)Galβ-OR$^2$, NeuAcα(2→3)Galβ(1→4) (Fucα1→3) GlcN(R$^1$)β-OR$^2$, or NeuAcα(2→3)Galβ(1→4) (Fucα1→3) GlcN(R$^1$)β(1→3)Galβ-OR$^2$, wherein R$^1$ is alkyl or acyl from 1-18 carbons, 5,6,7,8-tetrahydro-2-naphthamido; benzamido; 2-naphthamido; 4-aminobenzamido; or 4-nitrobenzamido, and R$^2$ is a hydrogen, a saccharide, an oligosaccharide or an aglycon group having at least one carbon atom.

In another embodiment, the invention provides methods of purifying a carbohydrate compound from a feed solution comprising a reaction mixture used to synthesize the carbohydrate compound. The synthesis can be enzymatic or chemical, or a combination thereof. The methods involve removing any proteins present in the feed solution by contacting the feed solution with an ultrafiltration membrane so that proteins are retained the membrane while the carbohydrate compound passes through the membrane as a permeate. The permeate from the ultrafiltration step is then contacted with a nanofiltration or reverse osmosis membrane under conditions such that the nanofiltration or reverse osmosis membrane retains the carbohydrate compound while a majority of an undesired contaminant passes through the membrane.

Another embodiment of the invention provides methods for purifying nucleotides, nucleosides, and nucleotide sugars by contacting a feed solution containing the nucleotide or related compound with a nanofiltration or reverse osmosis membrane under conditions such that the membrane retains the nucleotide or related compound while a majority of the contaminant passes through the membrane.

The present invention also provides methods for removing one or more contaminants from a solution that contains a carbohydrate of interest. The methods involve contacting the solution with a first side of a semipermeable membrane having rejection coefficients so as to retain the carbohydrate while allowing the contaminant to pass through the membrane. The membrane is selected from the group consisting of an ultrafiltration membrane, a nanofiltration membrane, and a reverse osmosis membrane, depending on the size and charge of the carbohydrate of interest relative to those of the contaminants. The membrane separates a feed solution containing a carbohydrate into a retentate portion and a permeate portion. If the rejection coefficient of the membrane is greater for the carbohydrate than for the contaminant, the retentate portion will have a lower concentration of the contaminant relative to the contaminant concentration in the feed solution, and generally also a higher ratio of the carbohydrate to the undesired contaminant. Conversely, a membrane having a rejection coefficient for the carbohydrate that is lesser than that for the contaminant will effect a separation wherein the concentration of the contaminant is lower in the permeate than in the feed solution, and the permeate will have a higher ratio of carbohydrate to contaminant than the feed solution. If desired, the fraction containing the carbohydrate can be recycled through the membrane system for further purification.

Examples of contaminants that can be removed from solutions containing the compound of interest using the methods of the invention include, but are not limited to, unreacted sugars, inorganic ions, pyruvate, phosphate, phosphoenolpyruvate, and proteins.

BRIEF DESCRIPTION OF THE DRAWINGS

FIG. 7, which includes FIGS. 7A-7N, is a table of exemplary sialyltransferases.

DESCRIPTION OF THE PREFERRED EMBODIMENTS

Definitions

Figure 1:
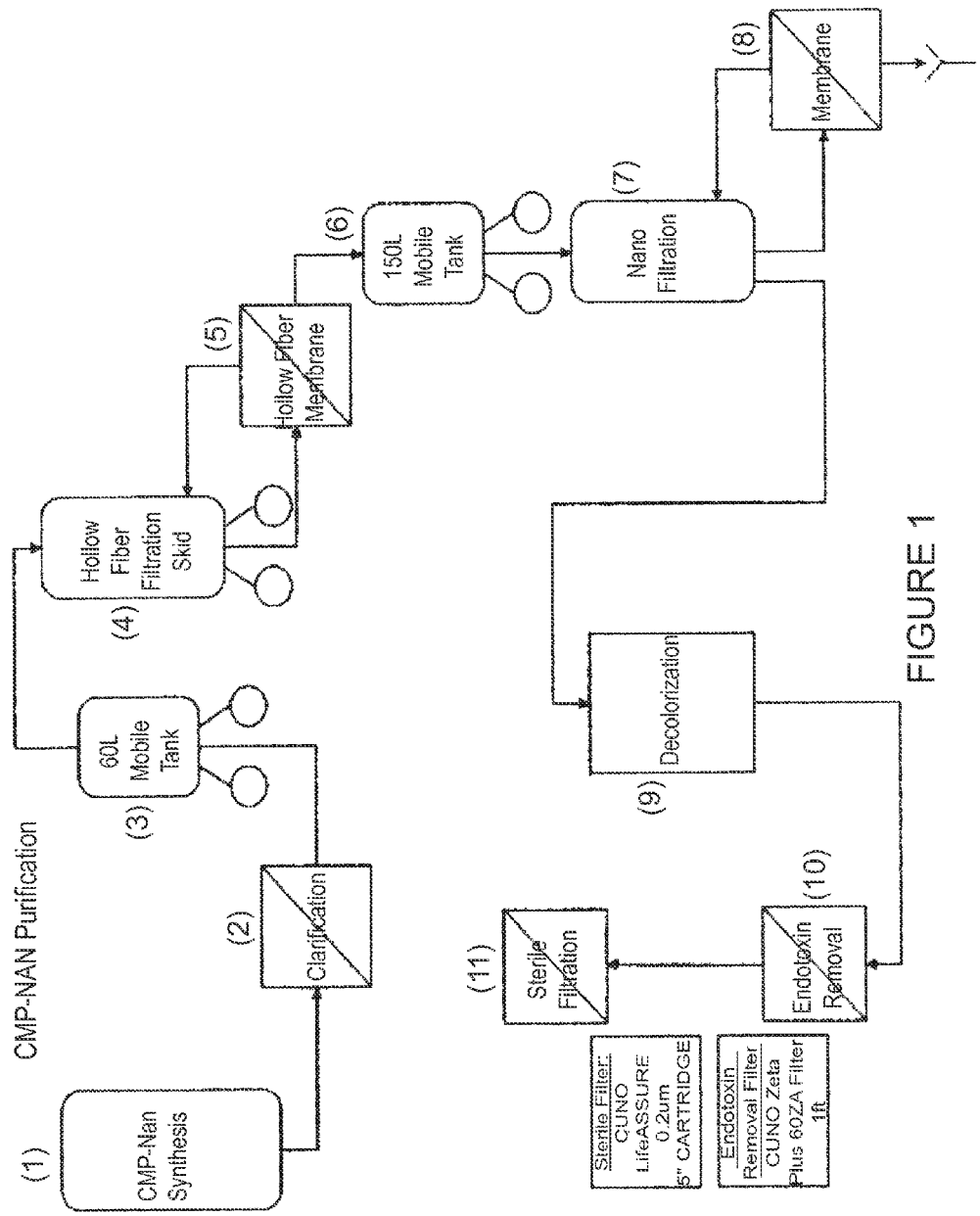
FIG. 1 is a diagram of an exemplary purification of a nucleotide sugar.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_5$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

As used herein, the term "modified sugar," refers to a naturally- or non-naturally-occurring carbohydrate. The modified sugar is preferably selected from a number of enzyme substrates including, but not limited to sugar nucleotides (mono-, di-, and tri-phosphates), activated sugars (e.g., glycosyl halides, glycosyl mesylates) and sugars that are neither activated nor nucleotides. The "modified sugar" is covalently functionalized with a "modifying group." Useful modifying groups include, but are not limited to, water-soluble polymers, targeting moieties therapeutic moieties, diagnostic moieties, radioactive moieties, cytotoxic moieties, biomolecules and the like. The modifying group is preferably not a naturally occurring, or an unmodified carbohydrate. The locus of functionalization with the modifying group is preferably selected such that it does not prevent the "modified sugar" from being added enzymatically to a peptide.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like. Peptides can have mixed sequences of be composed of a single amino acid, e.g., poly(lysine). An exemplary polysaccharide is poly(sialic acid). An exemplary poly(ether) is poly(ethylene glycol), e.g., m-PEG. Poly(ethylene imine) is an exemplary polyamine, and poly(acrylic) acid is a representative poly(carboxylic acid).

The polymer backbone of the water-soluble polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly (ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as $R(-PEG-OH)_m$ in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of from about 100 Da to about 100,000 Da, often from about 6,000 Da to about 80,000 Da.

The term "targeting moiety," as used herein, refers to species that will selectively localize in a particular tissue or region of the body. The localization is mediated by specific recognition of molecular determinants, molecular size of the targeting agent or conjugate, ionic interactions, hydrophobic interactions and the like. Other mechanisms of targeting an agent to a particular tissue or region are known to those of skill in the art. Exemplary targeting moieties include antibodies, antibody fragments, transferrin, HS-glycoprotein, coagulation factors, serum proteins, β-glycoprotein, G-CSF, GM-CSF, M-CSF, EPO and the like.

As used herein, "therapeutic moiety" means any agent useful for therapy including, but not limited to, antibiotics, anti-inflammatory agents, anti-tumor drugs, cytotoxins, and radioactive agents. "Therapeutic moiety" includes prodrugs of bioactive agents, constructs in which more than one therapeutic moiety is bound to a carrier, e.g., multivalent agents. Therapeutic moiety also includes proteins and constructs that include proteins. Exemplary proteins include, but are not limited to, Erythropoietin (EPO), Granulocyte Colony Stimulating Factor (GCSF), Granulocyte Macrophage Colony Stimulating Factor (GMCSF), Interferon (e.g., Interferon-α, -β, -γ), Interleukin (e.g., Interleukin II), serum proteins (e.g., Factors VII, VIIa, VIII, IX, and X), Human Chorionic Gonadotropin (HCG), Follicle Stimulating Hormone (FSH) and Lutenizing Hormone (LH) and antibody fusion proteins (e.g. Tumor Necrosis Factor Receptor ((TNFR)/Fc domain fusion protein)).

As used herein, "anti-tumor drug" means any agent useful to combat cancer including, but not limited to, cytotoxins and agents such as antimetabolites, alkylating agents, anthracyclines, antibiotics, antimitotic agents, procarbazine, hydroxyurea, asparaginase, corticosteroids, interferons and radioactive agents. Also encompassed within the scope of the term "anti-tumor drug," are conjugates of peptides with anti-tumor activity, e.g. TNF-α. Conjugates include, but are not limited to those formed between a therapeutic protein and a glycoprotein of the invention. A representative conjugate is that formed between PSGL-1 and TNF-α.

As used herein, "a cytotoxin or cytotoxic agent" means any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracinedione, mitoxantrone, mithramycin, actinomycin D, 1-dehydrotestosterone, glucocorticoids, procaine, tetracaine, lidocaine, propranolol, and puromycin and analogs or homologs thereof. Other toxins include, for example, ricin, CC-1065 and analogues, the duocarmycins. Still other toxins include diptheria toxin, and snake venom (e.g., cobra venom).

As used herein, "a radioactive agent" includes any radioisotope that is effective in diagnosing or destroying a tumor. Examples include, but are not limited to, indium-111, cobalt-60. Additionally, naturally occurring radioactive elements such as uranium, radium, and thorium, which typically represent mixtures of radioisotopes, are suitable examples of a radioactive agent. The metal ions are typically chelated with an organic chelating moiety.

Many useful chelating groups, crown ethers, cryptands and the like are known in the art and can be incorporated into the compounds of the invention (e.g., EDTA, DTPA, DOTA, NTA, HDTA, etc. and their phosphonate analogs such as DTPP, EDTP, HDTP, NTP, etc). See, for example, Pitt et al., "The Design of Chelating Agents for the Treatment of Iron Overload," In, INORGANIC CHEMISTRY IN BIOLOGY AND MEDICINE; Martell, Ed.; American Chemical Society, Washington, D.C., 1980, pp. 279-312; Lindoy, THE CHEMISTRY OF MACROCYCLIC LIGAND COMPLEXES; Cambridge University Press, Cambridge, 1989; Dugas, BIOORGANIC CHEMISTRY; Springer-Verlag, New York, 1989, and references contained therein.

Additionally, a manifold of routes allowing the attachment of chelating agents, crown ethers and cyclodextrins to other molecules is available to those of skill in the art. See, for example, Meares et al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, et al., Eds., American Chemical Society, Washington, D.C., 1982, pp. 370-387; Kasina et al., *Bioconjugate Chem.*, 9: 108-117 (1998); Song et al., *Bioconjugate Chem.*, 8: 249-255 (1997).

A compound is "substantially purified" from an undesired component in a solution if the concentration of the undesired component after purification is no greater than about 40% of the concentration of the component prior to purification. Preferably, the post-purification concentration of the undesired component will be less than about 20% by weight, and more preferably less than about 10%, and still more preferably less than about 5% of the pre-purification concentration.

The term "pharmaceutically pure," as used herein, refers to a compound that is sufficiently purified from undesired contaminants that the compound is suitable for administration as a pharmaceutical agent. Preferably, the compound is purified such that the undesired contaminant is present after purification in an amount that is about 5% by weight or less of the pre-purification concentration of the contaminant in the feed solution. More preferably, the post-purification concentration of the contaminant is about 1% or less of the pre-purification contaminant concentration, and most preferably about 0.5% or less of the pre-purification concentration of contaminant.

A "feed solution" refers to any solution that contains a compound to be purified. For example, a reaction mixture used to synthesize an oligosaccharide can be used as a feed solution from which the desired reaction product is purified using the methods of the invention.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "alkyl," by itself or as part of another substituent means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkylencamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R"')$_d$—, where s and d are independently integers of from 0 to 3, and X is —O—, —NR'—, —S—, —S(O)—, —S(O)$_2$—, or —S(O)$_2$NR'—. The substituents R, R', R" and R"' are preferably independently selected from hydrogen or substituted or unsubstituted ($C_1$-$C_6$)alkyl.

As used herein, the term "heteroatom" is meant to include oxygen (O), nitrogen (N), sulfur (S) and silicon (Si).

EMBODIMENTS OF THE INVENTION

The present invention provides methods for rapidly and efficiently purifying specific carbohydrate and oligosaccharide structures to a high degree of purity using semipermeable membranes such as reverse osmosis and/or nanofiltration membranes. The methods are particularly useful for separating desired oligosaccharide compounds from reactants and other contaminants that remain in a reaction mixture after synthesis or breakdown of the oligosaccharides. For example, the invention provides methods for separating oligosaccharides from enzymes and/or other components of reaction mixtures used for enzymatic synthesis or enzymatic degradation of oligosaccharides, nucleotide sugars, glycolipids, liposaccharides, nucleotides, nucleosides, and other saccharide-containing compounds. Also provided are methods for removing salts, sugars and other components from feed solutions using ultrafiltration, nanofiltration or reverse osmosis. Using these techniques, the saccharides (e.g., sialyl lactose, SLe$^x$, and many others) can be produced at up to essentially 100% purity. Moreover, the purification methods of the invention are more efficient, rapid, and amenable to large-scale purifications than previously known carbohydrate purification methods.

Often, a desired purification can be effected in a single step; additional purification steps such as crystallization and the like are generally not required. Accordingly, the invention provides single-step methods for purifying saccharide-containing compounds.

To purify saccharides according to the methods of the invention, a membrane is selected that is appropriate for separating the desired carbohydrate from the undesired components (contaminants) of the solution from which the carbohydrate is to be purified. The goal in selecting a membrane is to optimize for a particular application the molecular weight cutoff (MWCO), membrane composition, permeability, and rejection characteristics, that is, the membrane's total capacity to retain specific molecules while allowing other species, e.g., salts and other, generally smaller or opposite charged molecules, to pass through. The percent retention of a component i ($R_i$) is given by the formula $R_i = (1 - C_{ip}/C_{ir}) \times 100\%$, wherein $C_{ip}$ is the concentration of component i in the permeate and $C_{ir}$ is the concentration of component i in the retentate, both expressed in weight percent. The percent retention of a component is also called the retention characteristic or the membrane rejection coefficient.

In and exemplary embodiment, a membrane is chosen that has a high rejection ratio for the saccharide of interest relative to the rejection ratio for compounds from which separation is desired. If a membrane has a high rejection ratio for a first compound relative to a second compound, the concentration of the first compound in the permeate solution which passes through the membrane is decreased relative to that of the second compound. Conversely, the concentration of the first compound increases relative to the concentration of the second compound in the retentate. If a membrane does not reject a compound, the concentration of the compound in both the permeate and the reject portions will remain essentially the same as in the feed solution. It is also possible for a membrane to have a negative rejection rate for a compound if the compound's concentration in the permeate becomes greater than the compound's concentration in the feed solution. A general review of membrane technology is found in "Membranes and Membrane Separation Processes," in Ullmann's *Encyclopedia of Industrial Chemistry* (VCH, 1990); see also, Noble and Stem, *Membrane Separations Technology: Principles and Applications* (Elsevier, 1995).

As a starting point, one will generally choose a membrane having a molecular weight cut-off (MWCO, which is often related to membrane pore size) that is expected to retain the desired compounds while allowing an undesired compound present in the feed stream to pass through the membrane. The desired MWCO is generally less than the molecular weight of the compound being purified, and is typically greater than the molecular weight of the undesired contaminant that is to be removed from the solution containing the compound being purified. For example, to purify a compound having a molecular weight of 200 Da, one would choose a membrane that has a MWCO of less than about 200 Da. A membrane with a MWCO of 100 Da, for example, would also be a suitable candidate. The membranes that find use in the present invention are classified in part on the basis of their MWCO as ultrafiltration (UF) membranes, nanofiltration (NF) membranes, or reverse osmosis (RO) membranes, depending on the desired separation. For purposes of this invention, UF, NF, and RO membranes are classified as defined in the *Pure Water*

Handbook, Osmonics, Inc. (Minnetonka Minn.). RO membranes typically have a nominal MWCO of less than about 200 Da and reject most ions, NF membranes generally have a nominal MWCO of between about 150 Da and about 5 kDa, and UF membranes generally have a nominal MWCO of between about 1 kDa and about 300 kDa (these MWCO ranges assume a saccharide-like molecule).

A second parameter that is considered in choosing an appropriate membrane for a particular separation is the polymer type of the membrane. Exemplary membranes of use in the invention are made of conventional membrane material whether inorganic, organic, or mixed inorganic and organic. Typical inorganic materials include glasses, ceramics, cermets, metals and the like. Ceramic membranes, which are preferred for the UF zone, may be made, for example, as described in U.S. Pat. No. 4,692,354 to Asaeda et al, U.S. Pat. No. 4,562,021 to Alary et al., and others. The organic materials which are preferred for the NF and RO applications, are typically polymers, whether isotropic, or anisotropic with a thin layer or "skin" on either the bore side or the shell side of the fibers. Preferred materials for fibers are polyamides, polybenzamides, polysulfones (including sulfonated polysulfone and sulfonated polyether sulfone, among others), polystyrenes, including styrene-containing copolymers such as acrylo-nitrile-styrene, butadiene-styrene and styrene-vinylbenzylhalide copolymers, polycarbonates, cellulosic polymers including cellulose acetate, polypropylene, poly(vinyl chloride), poly(ethylene terephthalate), polyvinyl alcohol, fluorocarbons, and the like, such as those disclosed in U.S. Pat. Nos. 4,230,463, 4,806,244, and 4,259,183. The NF and RO membranes often consist of a porous support substrate in addition to the polymeric discrimination layer.

Of particular importance in selecting a suitable membrane composition is the membrane surface charge. Within the required MWCO range, a membrane is selected that has a surface charge that is appropriate for the ionic charge of the carbohydrate and that of the contaminants. While MWCO for a particular membrane is generally invariable, changing the pH of the feed solution can affect separation properties of a membrane by altering the membrane surface charge. For example, a membrane that has a net negative surface charge at neutral pH can be adjusted to have a net neutral charge simply by lowering the pH of the solution. An additional effect of adjusting solution pH is to modulate the ionic charge on the contaminants and on the carbohydrate of interest. Therefore, by choosing a suitable membrane polymer type and pH, one can obtain a system in which both the contaminant and the membrane are neutral, facilitating pass-through of the contaminant. If, for instance, a contaminant is negatively charged at neutral pH, it is often desirable to lower the pH of the feed solution to protonate the contaminant. For example, removal of phosphate is facilitated by lowering the pH of the solution to about 3, which protonates the phosphate anion, allowing passage through a membrane. For purification of an anionic carbohydrate, the pH will generally between about pH 1 and about pH 7. Conversely, if contaminant has a positive surface charge, the pH of the feed solution can be adjusted to between about pH 7 and about pH 14. For example, increasing the pH of a solution containing a contaminant having an amino group ($—NH_3^+$) will make the amino group neutral, thus facilitating its passage through the membrane. Thus, one aspect of the invention involves modulating a separation by adjusting the pH of a solution in contact with the membrane; this can change the ionic charge of a contaminant and can also affect the surface charge of the membrane, thus facilitating purification if the desired carbohydrate. Of course, the manufacturer's instructions must be followed as to acceptable pH range for a particular membrane to avoid damage to the membrane.

For some applications, a mixture is first subjected to nanofiltration or reverse osmosis at one pH, after which the retentate containing the saccharide of interest is adjusted to a different pH and subjected to an additional round of membrane purification. For example, filtration of a reaction mixture used to synthesize sialyl lactose through an Osmonics MX07 membrane (a nanofiltration membrane having a MWCO of about 500 Da) at pH 3.0 will retain the sialyl lactose and remove most phosphate, pyruvate, salt and manganese from the solution, while also removing some of the GlcNAc, lactose, and sialic acid. Further recirculation through the MX07 membrane after adjusting the pH of the retentate to 7.4 will remove most of the remaining phosphate, all of the pyruvate, all of the lactose, some of the sialic acid, and substantial amounts of the remaining manganese.

If a saccharide is to be purified from a mixture that contains proteins, such as enzymes used to synthesize a desired oligosaccharide or nucleotide sugar, it is often desirable to remove the proteins as a first step of the purification procedure. For a saccharide that is smaller than the proteins, this separation is accomplished by choosing a membrane that has an MWCO which is less than the molecular mass of the protein or other macromolecule to be removed from the solution, but is greater than the molecular mass of the oligosaccharide being purified (i.e., the rejection ratio in this case is higher for the protein than for the desired saccharide). Proteins and other macromolecules that have a molecular mass greater than the MWCO will thus be rejected by the membrane, while the saccharide will pass through the membrane. Conversely, if an oligosaccharide or nucleotide sugar is to be purified from proteins that are smaller than the oligosaccharide or nucleotide sugar, a membrane is used that has a MWCO that is larger than the molecular mass of the protein but smaller than that of the oligosaccharide or nucleotide sugar. Generally, separation of proteins from carbohydrates will employ membranes that are commonly referred to as ultrafiltration (UF) membranes. UF membranes that are suitable for use in the methods of the invention are available from several commercial manufacturers, including Millipore Corp. (Bedford, Mass.), Osmonics, Inc. (Minnetonka, Minn.), Filmtec (Minneapolis, Minn.), UOP, Desalination Systems, Advanced Membrane Technologies, and Nitto.

The invention also provides methods for removing salts and other low molecular weight components from a mixture containing a saccharide of interest by using a nanofiltration (NF) or a reverse osmosis (RO) membrane. Nanofiltration membranes are a class of membranes for which separation is based both on molecular weight and ionic charge. These membranes typically fall between reverse osmosis and ultrafiltration membranes in terms of the size of species that will pass through the membrane. Nanofiltration membranes typically have micropores or openings between chains in a swollen polymer network. Molecular weight cut-offs for non-ionized molecules are typically in the range from 100-20,000 Daltons. For ions of the same molecular weight, membrane rejections (retentions) will increase progressively for ionic charges of 0, 1, 2, 3 etc. for a particular membrane because of increasing charge density (see, e.g., Eriksson, P., "Nanofiltration Extends the Range of Membrane Filtration," *Environmental Progress*, 7: 58-59 (1988)). Nanofiltration is also described in *Chemical Engineering Progress*, pp. 68-74 (March 1994), Rautenbach et al., *Desalination* 77: 73 (1990), and U.S. Pat. No. 4,806,244). In a typical application, saccharides of interest will be retained by the nanofiltration membrane and contaminating salts and other undesired components will pass through. A nanofiltration membrane useful in the methods of the invention will typically have a retention characteristic for the saccharide of interest of from about 40% to about 100%, preferably from about 70% to about 100%, more preferably from about 90% to about 100%. The nanofilter membranes used in the invention can be any one of the conventional nanofilter membranes, with polyamide membranes being particularly suitable. Several commercial manufacturers, including Millipore Corp. (Bedford, Mass.), Osmonics, Inc. (Minnetonka, Minn.), Filmtec, UOP, Advanced Membrane Technologies, Desalination Systems, and Nitto, among others, distribute nanofiltration membranes that are suitable for use in the methods of the invention. For example, suitable membranes include the Osmonics MX07, YK, GH (G-10), GE (G-5), and HL membranes, among others.

Reverse osmosis (RO) membranes also allow a variety of aqueous solutes to pass through them while retaining selected molecules. Generally, osmosis refers to a process whereby a pure liquid (usually water) passes through a semipermeable membrane into a solution (usually sugar or salt and water) to dilute the solution and achieve osmotic equilibrium between the two liquids. In contrast, reverse osmosis is a pressure driven membrane process wherein the application of external pressure to the membrane system results in a reverse flux with the water molecules passing from a saline or sugar solution compartment into the pure water compartment of the membrane system. A RO membrane, which is semipermeable and non-porous, requires an aqueous feed to be pumped to it at a pressure above the osmotic pressure of the substances dissolved in the water. An RO membrane can effectively remove low molecular weight molecules (<200 Daltons) and also ions from water. Preferably, the reverse osmosis membrane will have a retention characteristic for the saccharide of interest of from about 40% to about 100%, preferably from about 70% to about 100%, and more preferably from about 90% to about 100%. Suitable RO membranes include, but are not limited to, the Filmtec BW-30, Filmtec SW-30, Filmtec SW-30HR, UOP RO membranes, Desal RO membranes, Osmonics RO membranes, Advanced Membrane Technologies RO membranes, and the Nitto RO membranes, among others. One example of a suitable RO membrane is Millipore Cat. No. CDRN500 60 (Millipore Corp., Bedford Mass.).

The membranes used in the invention may be employed in any of the known membrane constructions. For example, the membranes can be flat, plate and frame, tubular, spiral wound, hollow fiber, and the like. In a preferred embodiment, the membrane is spiral wound. The membranes can be employed in any suitable configuration, including either a cross-flow or a depth configuration. In "cross-flow" filtration, which is preferred for ultrafiltration, nanofiltration and reverse osmosis purifications according to the invention, the "feed" or solution from which the carbohydrate of interest is to be purified flows through membrane channels, either parallel or tangential to the membrane surface, and is separated into a retentate (also called recycle or concentrate) stream and a permeate stream. To maintain an efficient membrane, the feed stream should flow, at a sufficiently high velocity, parallel to the membrane surface to create shear forces and/or turbulence to sweep away accumulating particles rejected by the membrane. Cross-flow filtration thus entails the flow of three streams—feed, permeate and retentate. In contrast, a "dead end" or "depth" filter has only two streams—feed and filtrate (or permeate). The recycle or retentate stream, which retains all the particles and large molecules rejected by the membrane, can be entirely recycled to the membrane module in which the recycle stream is generated, or can be partially removed from the system. When the methods of the invention are used to purify saccharides from lower molecular weight components, for example, the desired saccharides are contained in the retentate stream (or feed stream, for a depth filter), while the permeate stream contains the removed contaminants.

The purification methods of the invention can be further optimized by adjusting the pressure, flow rate, and temperature at which the filtration is carried out. UF, NF, and RO generally require increasing pressures above ambient to overcome the osmotic pressure of the solution being passed through the membrane. The membrane manufacturers' instructions as to maximum and recommended operating pressures can be followed, with further optimization possible by making incremental adjustments. For example, the recommended pressure for UF will generally be between about 25 and about 100 psi, for NF between about 50 psi and about 1500 psi, and for RO between about 100 and about 1500 psi. Flow rates of both the concentrate (feed solution) and the permeate can also be adjusted to optimize the desired purification. Again, the manufacturers' recommendations for a particular membrane serve as a starting point from which to begin the optimization process by making incremental adjustments. Typical flow rates for the concentrate ($P_c$) will be between about 1 and about 15 gallons per minute (GPM), and more preferably between about 3 and about 7 GPM. For the permeate, flow rates ($P_f$) of between about 0.05 GPM and about 10 GPM are typical, with flow rates between about 0.2 and about 1 GPM being preferred. The temperature at which the purification is carried out can also influence the efficiency and speed of the purification. Temperatures of between about 0 and about 100° C. are typical, with temperatures between about 20 and 40° C. being preferred for most applications. Higher temperatures can, for some membranes, result in an increase in membrane pore size, thus providing an additional parameter that one can adjust to optimize a purification.

In a preferred embodiment, the filtration is performed in a membrane purification machine which provides a means for automating control of flow rate, pressure, temperature, and other parameters that can affect purification. For example, the Osmonics 213T membrane purification machine is suitable for use in the methods of the invention, as are machines manufactured by other companies listed above.

The membranes can be readily cleaned either after use or after the permeability of the membrane diminishes. Cleaning can be effected at a slightly elevated temperature if so desired, by rinsing with water or a caustic solution. If the streams contain small amounts of enzyme, rinsing in the presence of small amounts of surfactant, for instance ULTRASIL, is useful. Also, one can use prefilters (100-200 μm) to protect the more expensive nanofiltration membranes. Other cleaning agents can, if desired, be used. The choice of cleaning method will depend on the membrane being cleaned, and the membrane manufacturer's instructions should be consulted. The cleaning can be accomplished with a forward flushing or a backward flushing.

The purification methods of the invention can be used alone or in combination with other methods for purifying carbohydrates. For example, an ion exchange resin can be used to remove particular ions from a mixture containing a saccharide of interest, either before or after nanofiltration/reverse osmosis, or both before and after filtration. Ion exchange is particularly desirable if it is desired to remove ions such as phosphate and nucleotides that remain after a first round of nanofiltration or reverse osmosis. In the case of sialyl lactose synthesis as discussed above, this can be accomplished, for example, by adding an anion exchange resin such as AG1X-8 (acetate form, BioRad; see, e.g., BioRad catalog for other ion exchange resins) to a retentate that is at about pH 3.0 or lower until the phosphate concentration is reduced as desired. In this process, acetic acid is released, so one may wish to follow the ion exchange with an additional purification through the nanofiltration or reverse osmosis system. For example, one can circulate the pH 3.0 or lower solution through an Osmonics MX07 or similar membrane until the conductivity of the permeate is low and stabilized. The pH of the solution can then be raised to 7.4 with NaOH and the solution recirculated through the same membrane to remove remaining sodium acetate and salt. Cations can be removed in a similar manner; for example, to remove $Mn^{2+}$, an acidic ion exchange resin can be used, such as AG50WX8 ($H^+$) (Bio-Rad).

As discussed above, the present invention provides methods of purifying a sugar nucleotide or conjugate thereof having any desired carbohydrate structure, e.g., modified with a polymeric moiety, from contaminants resulting from synthesis of the sugar nucleotide or conjugate thereof. Exemplary sugar nucleotides and conjugates based on these sugar structures are substituted with the polymeric modifying moiety at any desired position. In an exemplary embodiment, the sugar is a furanose that is substituted with a linker or modifying group attached through a linker at one or more of C-1, C-2, C-3, C-4 or C-5. In another embodiment, the invention provides a pyranose that is substituted with a linker or modifying group attached to the sugar through a linker at one or more of C-1, C-2, C-3, C-4, C-5 or C-6. Preferably, the linker and/or modifying group is attached directly to an oxygen, nitrogen or sulfur pendent from the carbon of the sugar.

In a presently preferred embodiment, the polymeric linker or modifying group is appended to a position that is selected such that the resulting conjugate functions as a substrate for an enzyme used to ligate the modified sugar moiety to another species, e.g., peptide, glycopeptide, lipid, glycolipid, etc. Exemplary enzymes are known in the art and include glycosyl transferases (sialyl transferases, glucosyl transferases, galactosyl transferases, N-acetylglucosyl transferases, N-acetylgalactosyl transferases, mannosyl transferases, fucosyl transferases, etc.). Exemplary sugar nucleotide and activated sugar conjugates of the invention also include substrates for mutant glycosidases and mutant glycoceramidases that are modified to have synthetic, rather than hydrolytic activity.

In an exemplary embodiment, the conjugate purified by a method of the invention includes a sugar, activated sugar or nucleotide sugar that is conjugated to one or more polymer, e.g. a branched polymer. Exemplary polymers include both water-soluble and water-insoluble species.

In an exemplary embodiment, the sugar nucleotide purified by a method of the invention has a formula selected from:

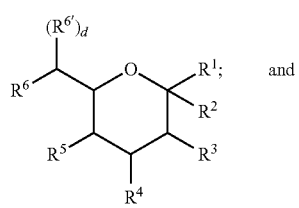

I and

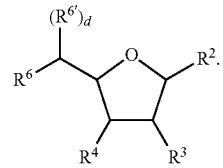

II

In Formulae I and II, $R^1$ is H, $CH_2OR^7$, $COOR^7$ or $OR^7$, in which $R^7$ represents H, substituted or unsubstituted alkyl or substituted or unsubstituted heteroalkyl. $R^2$ is H, OH, NH or a moiety that includes a nucleotide. An exemplary $R^2$ species according to this embodiment has the formula:

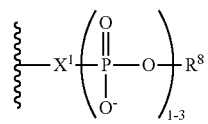

in which $X^1$ represents O or NH and $R^8$ is a nucleoside.

The symbols $R^3$, $R^4$, $R^5$, $R^6$ and $R^{6'}$ independently represent H, substituted or unsubstituted alkyl, $OR^9$, $NHC(O)R^{10}$. The index d is 0 or 1. $R^9$ and $R^{10}$ are independently selected from H, substituted or unsubstituted alkyl, substituted or unsubstituted heteroalkyl or sialic acid. At least one of $R^3$, $R^4$, $R^5$, $R^6$, and $R^{6'}$ includes the linker or linker-modifying group, e.g., PEG. In an exemplary embodiment, $R^6$ and $R^{6'}$, together with the carbon to which they are attached are components of the side chain of sialic acid. In still a further exemplary embodiment, this side chain is modified with the linker or linker-modifying moiety at one or more of C-6, C-7 or C-9.

In an exemplary embodiment, the linker arm has the structure below when w is 0, and when w is greater than 0, a modifying group is joined to the sugar core through the linker:

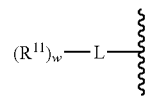

in which $R^{11}$ is the polymeric moiety and L is selected from a bond and a linking group, and w is an integer from 1-6, preferably 1-3 and more preferably, 1-2.

When L is a bond it is formed between a reactive functional group on a precursor of $R^{11}$ and a reactive functional group of complementary reactivity on a precursor of L. As set forth herein, the selection and preparation of precursors with appropriate reactive functional groups is within the ability of those skilled in the art. Moreover, combining the precursors proceeds by chemistries that are well-understood in the art.

In an exemplary embodiment L is a linking group that is formed from an amino acid, an amino acid mimetic, or small peptide (e.g., 1-4 amino acid residues) providing a modified sugar. In another embodiment, the modifying group is attached through the linker, e.g., a polymeric modifying moiety is attached through a substituted alkyl linker. The linker is formed through reaction of an amine moiety and carboxylic acid (or a reactive derivative, e.g., active ester, acid halide, etc.) of the amino acid with groups of complementary reactivity on the precursors to L and $R^{11}$. The elements of the conjugate can be conjugated in essentially any convenient order. For example the precursor to L can be in place on the saccharide core prior to conjugating the precursors of $R^{11}$ and L. Alternatively, an $R^{11}$-L cassette, bearing a reactive functionality on L can be prepared and subsequently linked to the saccharide through a reactive functional group of complementary reactivity on this species.

In an exemplary embodiment, the linker and/or modifying moiety is $R^3$ and/or $R^6$. In another exemplary embodiment, $R^3$ and/or $R^6$ includes both the polymeric modifying moiety and a linker, L, joining the polymeric moiety to the remainder of the molecule. In another exemplary embodiment, the modifying moiety is $R^3$. In a further exemplary embodiment, $R^3$ includes both the modifying group and a linker, L, joining the modifying group to the remainder of the molecule. In yet another exemplary embodiment in which the sugar is a sialic acid, the linker and/or modifying group is at $R^5$ or attached at a position of the sialic acid side chain, e.g., C-9.

In an exemplary embodiment, the present invention provides a method of purifying a sugar or activated sugar conjugate or nucleotide sugar conjugate that is formed between a linear polymer, such as a water-soluble or water-insoluble polymer. In these conjugates, the polymer is attached to a sugar, activated sugar or sugar nucleotide. As discussed herein, the polymer is linked to the sugar moiety, either directly or through a linker.

An exemplary compound according to this embodiment has a structure according to Formulae I or II, in which at least one of $R^1$, $R^3$, $R^4$, $R^5$ or $R^6$ has the formula:

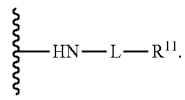

$R^{11}$ is present or absent. In this embodiment, an exemplary linker is derived from a natural or unnatural amino acid, amino acid analogue or amino acid mimetic, or a small peptide formed from one or more such species. For example, certain branched polymers found in the compounds purified by methods of the invention have the formula:

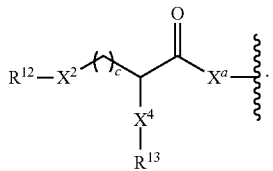

$X^a$ is a linking moiety that is formed by the reaction of a reactive functional group on a precursor of the branched polymeric modifying moiety and the sugar moiety, or a precursor to a linker. For example, when $X^3$ is a carboxylic acid, it can be activated and bound directly to an amine group pendent from an amino-saccharide (e.g., GalNH$_2$, GlcNH$_2$, ManNH$_2$, etc.), forming an $X^a$ that is an amide. Additional exemplary reactive functional groups and activated precursors are described hereinbelow. The index c represents an integer from 1 to 10. The other symbols have the same identity as those discussed above.

In another exemplary embodiment, $X^a$ is a linking moiety formed with another linker:

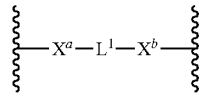

in which $X^b$ is a linking moiety and is independently selected from those groups set forth for $X^a$, and $L^1$ is a bond, substituted or unsubstituted alkyl or substituted or unsubstituted heteroalkyl.

Exemplary species for $X^a$ and $X^b$ include S, SC(O)NH, HNC(O)S, SC(O)O, O, NH, NHC(O), (O)CNH and NHC(O)O, and OC(O)NH.

Another example according to this embodiment has the formula:

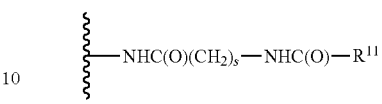

in which s is an integer from 0 to 20 and C(O)$R^{11}$ is present or absent and, when present, $R^{11}$ is a modifying group.

When the modifying group is a PEG moiety, the PEG moieties can have any molecular weight, e.g., 2 Kda, 5 Kda, 10 Kda, 20 Kda, 30 Kda and 40 Kda are of use in the present invention.

Exemplary nucleosides include AMP, UMP, GMP, CMP, TMP, ADP, UDP, GDP, CDP, TDP, ATP, UTP, GTP, CTP, TTP, cAMP and cGMP.

In a preferred embodiment, the sugar purified by the method of the invention includes a sialic acid modified with a linker group. Preferred sites for such modification are $R^5$, $R^6$ or $R^{6'}$. Thus, in a preferred embodiment, at least one of $R^1$ and $R^2$ includes a linker. An exemplary linker is a glycyl linker.

In another preferred embodiment, the nucleotide sugar purified by the methods set forth herein has the formula:

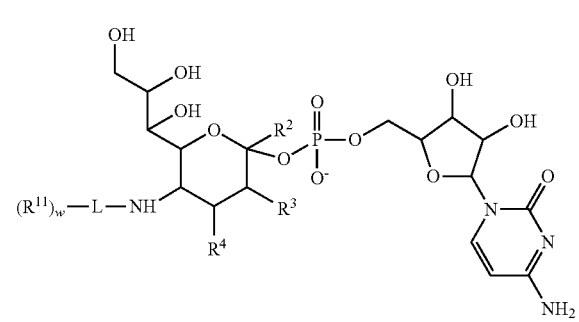

in which the radicals are as discussed above, and $R^{11}$ is a modifying group which is present or absent.

In a preferred embodiment, the modified sialic acid has the following structure:

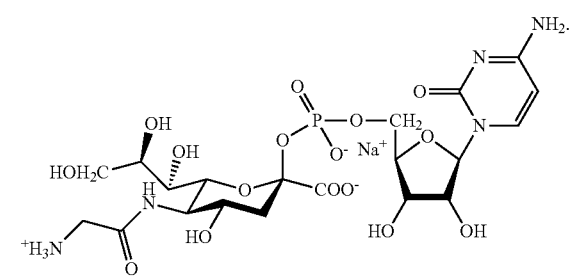

In yet another preferred embodiment, a modifying group is attached to the sialic acid through the linker. An exemplary species according to this description includes a modifying group attached through the free amine moiety of the linker. A presently preferred modifying group is a water-soluble polymer. Poly(ethylene glycol) is a preferred water-soluble polymer.

In another preferred embodiment, the compound purified by the instant method has the formula:

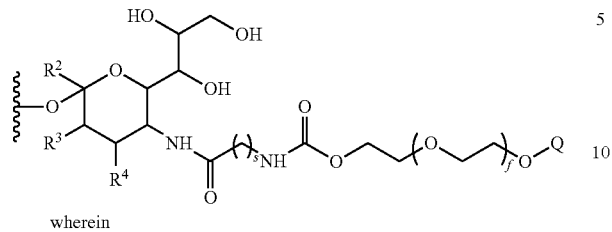

wherein

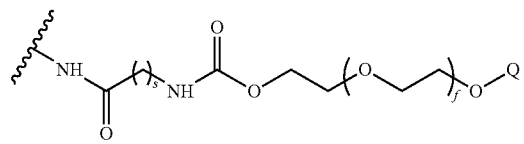

is a linker-modifying group. The index s is an integer selected from 1 to 20. The index f is an integer selected from 1 to 2500. Q is a member selected from H and substituted or unsubstituted $C_1$-$C_6$ alkyl.

Exemplary PEG moieties included as modifying groups in the compounds purified by the methods of the invention include, but are not limited to:

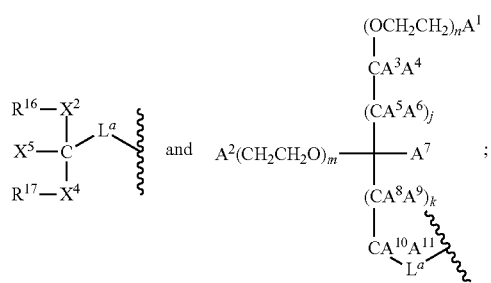

wherein $L^a$ is a linker selected from a bond, substituted or unsubstituted alkyl and substituted or unsubstituted heteroalkyl. The symbols $X^5$, $R^{16}$ and $R^{17}$ independently represent polymeric moieties and non-reactive groups. $X^2$ and $X^4$ represent independently selected linkage fragments joining polymeric moieties $R^{16}$ and $R^{17}$ to C. The indices m and n are integers independently selected from 0 to 5000.

The symbols $A^1, A^2, A^3, A^4, A^5, A^6, A^7, A^8, A^9, A^{10}$ and $A^{11}$ represent H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $-NA^{12}A^{13}$, $-OA^{12}$ or $-SiA^{12}A^{13}$. $A^{12}$ and $A^{13}$ are members independently selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

Exemplary linkage fragments for $X^2$ and $X^4$ include S, SC(O)NH, HNC(O)S, SC(O)O, O, NH, NHC(O), (O)CNH and NHC(O)O, and OC(O)NH, $CH_2S$, $CH_2O$, $CH_2CH_2O$, $CH_2CH_2S$, $(CH_2)_aO$, $(CH_2)_aS$ or $(CH_2)_aY'$-PEG or $(CH_2)_aY'$-PEG wherein $Y'$ is S or O and a is an integer from 1 to 50.

In an exemplary embodiment, the polymeric modifying group has a structure according to the following formulae:

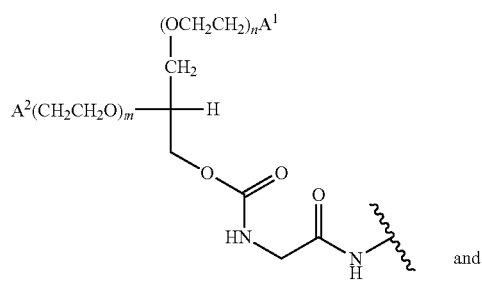

In another exemplary embodiment according to the formula above, the polymeric modifying group has a structure according to the following formula:

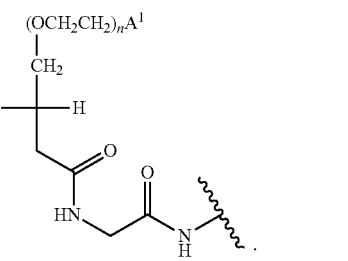

In an exemplary embodiment, $A^1$ and $A^2$ are each members selected from $-OH$ and $-OCH_3$.

Exemplary linker-polymeric modifying groups according to this embodiment include:

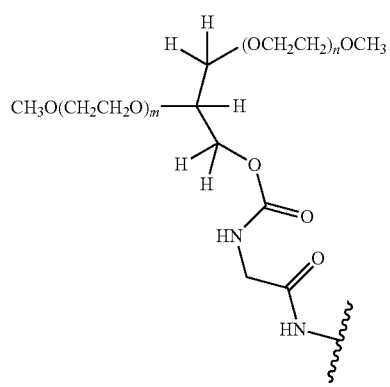

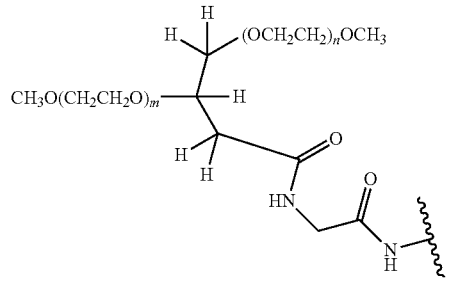

Further specific embodiments of linear and branched polymers, e.g., PEGs, of use in the invention include:

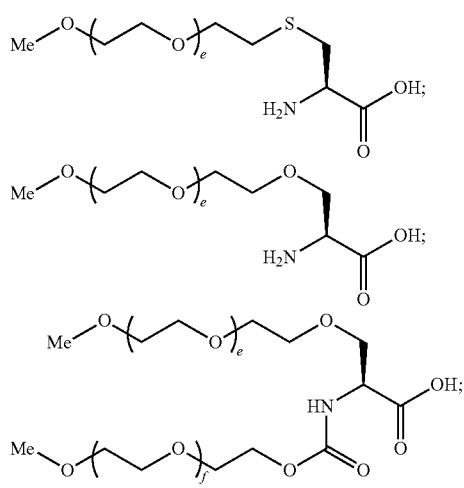

and carbonates and active esters of these species, such as:

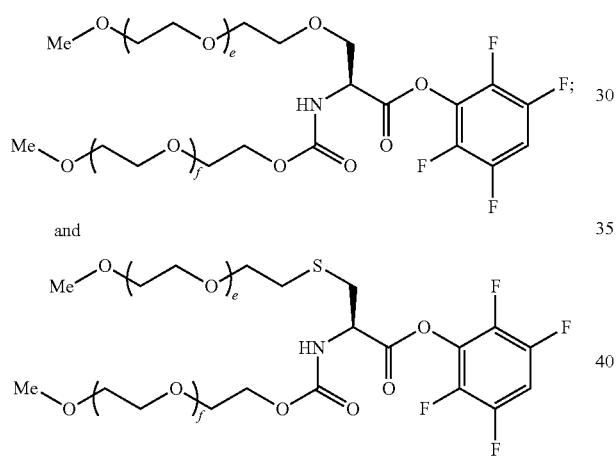

and can be used to form the linear and branched polymeric species, linker arm conjugates of these species and conjugates between these compounds and sugars and nucleotide sugars.

Other exemplary activating, or leaving groups, appropriate for activating linear PEGs of use in preparing the compounds set forth herein include, but are not limited to the species:

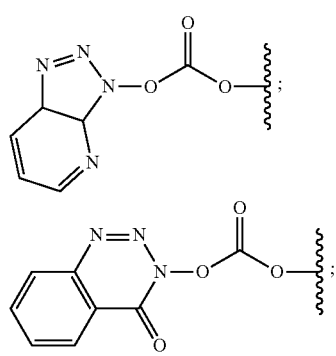

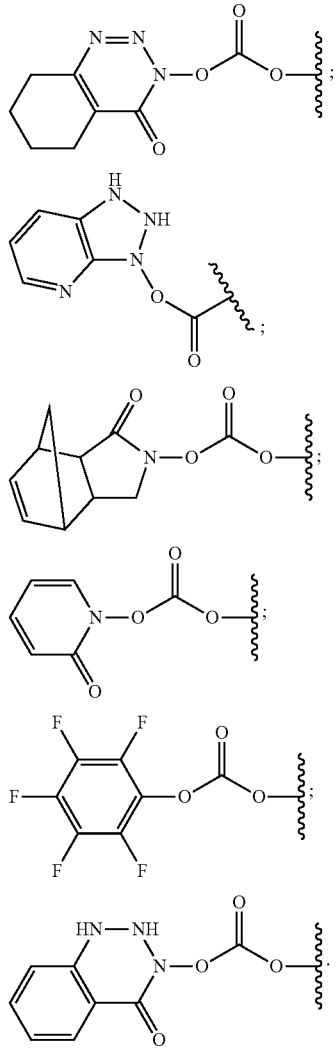

It is well within the abilities of those of skill in the art to select an appropriate activating group for a selected moiety on the precursor to the polymeric modifying moiety.

PEG molecules that are activated with these and other species and methods of making the activated PEGs are set forth in WO 04/083259.

In exemplary embodiments, the branched polymer is a PEG is based upon a cysteine, serine, lysine, di- or tri-lysine core. Thus, further exemplary branched PEGs include:

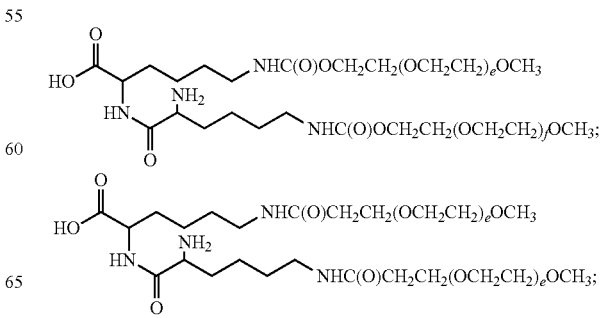

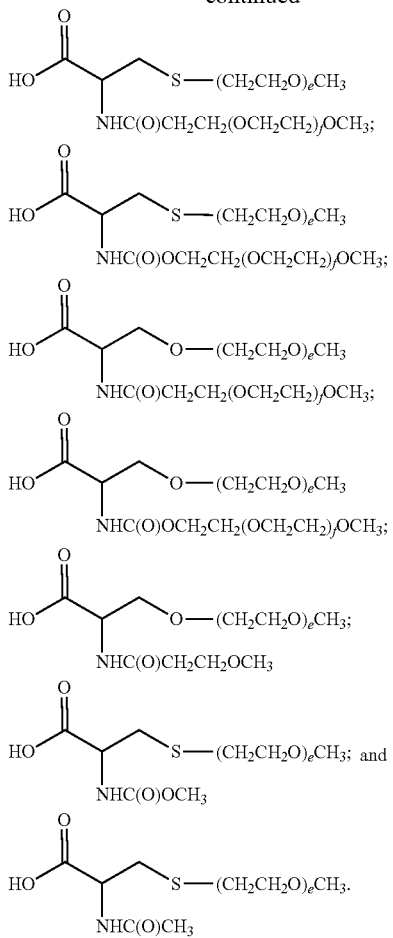

In yet another embodiment, the branched PEG moiety is based upon a tri-lysine peptide. The tri-lysine can be mono-, di-, tri-, or tetra-PEG-ylated. Exemplary species according to this embodiment have the formulae:

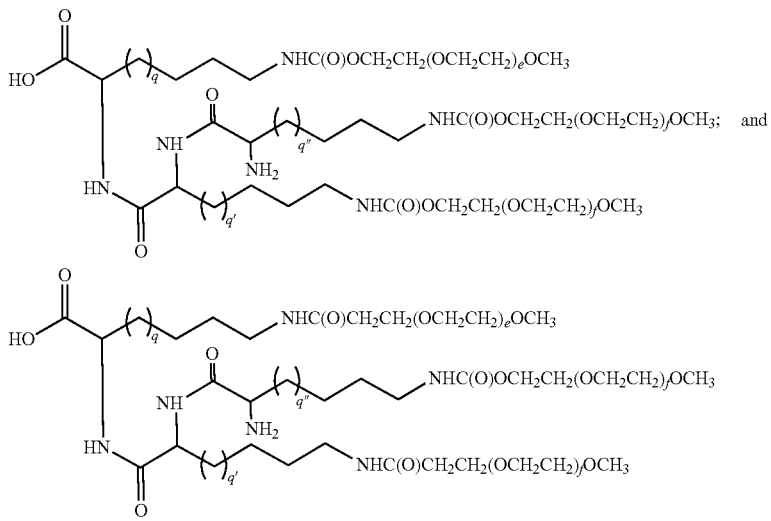

in which e, f and f' are independently selected integers from 1 to 2500; and q, q' and q" are independently selected integers from 1 to 20.

In exemplary embodiments of the invention, the PEG is m-PEG (5 kD, 10 kD, or 20 kD). An exemplary branched PEG species is a serine- or cysteine-(m-PEG)$_2$ in which the m-PEG is a 20 kD m-PEG.

As will be apparent to those of skill, the branched polymers of use in the invention include variations on the themes set forth above. For example the di-lysine-PEG conjugate shown above can include three polymeric subunits, the third bonded to the α-amine shown as unmodified in the structure above. Similarly, the use of a tri-lysine functionalized with three or four polymeric subunits is within the scope of the invention.

Those of skill in the art will appreciate that one or more of the m-PEG arms of the branched polymer can be replaced by a PEG moiety with a different terminus, e.g., OH, COOH, NH$_2$, C$_2$-C$_{10}$-alkyl, etc. Moreover, the structures above are readily modified by inserting alkyl linkers (or removing carbon atoms) between the α-carbon atom and the functional group of the side chain. Thus, "homo" derivatives and higher homologues, as well as lower homologues are within the scope of cores for branched PEGs of use in the present invention.

In an exemplary embodiment, $L^a$ is attached to a free amine moiety of the linker arm, e.g., glycyl linker, through an amine, amide or urethane bond.

In another exemplary embodiment, the PEG is a linear PEG. Similar to the branched PEG species, the linear PEG can be attached to an amine moiety of the linker arm through an amine, amide or urethane linkage.

Linear and branched PEGs preferably have a molecular weight of at least 1 Kd, preferably at least 5 Kd, more preferably at least 10 Kd, still more preferably at least 20 Kd, even more preferably at least 30 Kd, 40 Kd, 50 Kd and even more preferably at least 100 Kd.

The purification methods of the invention are particularly useful for purifying oligosaccharides, modified saccharides, nucleotide sugars and modified nucleotide sugars prepared using enzymatic synthesis. Enzymatic synthesis using glycosyltransferases provides a powerful method for preparing oligosaccharides; for some applications it is desirable to purify the oligosaccharide from the enzymes and other reactants in the enzymatic synthesis reaction mixture. Preferred methods for producing many oligosaccharides involve glycosyl transferase cycles, which produce at least one mole of inorganic pyrophosphate for each mole of product formed and are typically carried out in the presence of a divalent metal ion. Examples of glycosyltransferase cycles are the sialyltransferase cycles, which use one or more enzymes as well as other reactants. See, e.g., U.S. Pat. No. 5,374,541 WO 9425615 A, PCT/US96/04790, and PCT/US96/04824. For example, a reaction used for synthesis of sialylated oligosaccharides can contain a sialyltransferase (FIG. 7), a CMP-sialic acid synthetase, a sialic acid, an acceptor for the sialyltransferase, CTP, and a soluble divalent metal cation. An exemplary α(2,3)sialyltransferase referred to as α(2,3)sialtransferase (EC 2.4.99.6) transfers sialic acid to the non-reducing terminal Gal of a Galβ163Glc disaccharide or glycoside. See, Van den Eijnden et al., *J. Biol. Chem.*, 256:3159 (1981), Weinstein et al., *J. Biol. Chem.*, 257:13845 (1982) and Wen et al., *J. Biol. Chem.*, 267:21011 (1992). Another exemplary α2,3-sialyltransferase (EC 2.4.99.4) transfers sialic acid to the non-reducing terminal Gal of the disaccharide or glycoside. See, Rearick et al., *J. Biol. Chem.*, 254:4444 (1979) and Gillespie et al., *J. Biol. Chem.*, 267:21004 (1992). Further exemplary enzymes include Gal-β-1,4-GlcNAc α-2,6 sialyltransferase (See, Kurosawa et al. *Eur. J. Biochem.* 219: 375-381 (1994)). The reaction mixture will also contain an acceptor for the sialyltransferase, preferably having a galactosyl unit. Suitable acceptors, include, for example, Galβ1→3GalNAc, lacto-N-tetraose, Galβ1-43GlcNAc, Galβ1→3Ara, Galβ1→6GlcNAc, Galβ1→4Glc (lactose), Galβ1→4Glcβ1→OCH₂CH₃, Galβ1→4Glcβ1-OCH₂CH₂CH₃, Galβ1→4Glcβ1-OCH₂C₆H₅, Galβ1→4GlcNAc, Galβ1-OCH₃, melibiose, raffinose, stachyose, and lacto-N-neotetraose (LNnT). The sialic acid present in the reaction mixture can include not only sialic acid itself (5-N-acetylneuraminic acid; 5-N-acetylamino-3,5-dideoxy-D-glycero-D-galacto-2-nonulosonic acid; NeuAc, and sometimes also abbreviated AcNeu or NANA), but also 9-substituted sialic acids such as a 9-O—C₁-C₆ acyl-NeuAc like 9-O-lactyl-NeuAc or 9-O-acetyl-NeuAc, 9-deoxy-9-fluoro-NeuAc and 9-azido-9-deoxy-NeuAc. The synthesis and use of these compounds in a sialylation procedure is described in international application WO 92/16640, published Oct. 1, 1992.

In preferred embodiments the reaction medium can further comprise a CMP-sialic acid recycling system comprising at least 2 moles of phosphate donor per each mole of sialic acid, and catalytic amounts of an adenine nucleotide, a kinase capable of transferring phosphate from the phosphate donor to nucleoside diphosphates, and a nucleoside monophosphate kinase capable of transferring the terminal phosphate from a nucleoside triphosphate to CMP. For example, a suitable CMP-sialic acid regenerating system comprises cytidine monophosphate (CMP), a nucleoside triphosphate (for example adenosine triphosphate (ATP), a phosphate donor (for example, phosphoenolpyruvate or acetyl phosphate), a kinase (for example, pyruvate kinase or acetate kinase) capable of transferring phosphate from the phosphate donor to nucleoside diphosphates and a nucleoside monophosphate kinase (for example, myokinase) capable of transferring the terminal phosphate from a nucleoside triphosphate to CMP. The previously discussed α(2,3)sialyltransferase and CMP-sialic acid synthetase can also be formally viewed as part of the CMP-sialic acid regenerating system. For those embodiments in which a CMP-sialic acid recycling system is not used, the reaction medium will preferably further comprise a phosphatase.

Pyruvate is a byproduct of the sialyltransferase cycle and can be made use of in another reaction in which N-acetylmannosamine (ManNAc) and pyruvate are reacted in the presence of NeuAc aldolase (EC 4.1.3.3) to form sialic acid. Alternatively, advantage can be taken of the isomerization of GlcNAc to ManNAc, and the less expensive GlcNAc can be used as the starting material for sialic acid generation. Thus, the sialic acid can be replaced by ManNAc (or GlcNAc) and a catalytic amount of NeuAc aldolase. Although NeuAc aldolase also catalyzes the reverse reaction (NeuAc to ManNAc and pyruvate), the produced NeuAc is irreversibly incorporated into the reaction cycle via CMP-NeuAc catalyzed by CMP-sialic acid synthetase. In addition, the starting material, ManNAc, can also be made by the chemical conversion of GlcNAc using methods known in the art (see, e.g., Simon et al., *J. Am. Chem. Soc.* 110:7159 (1988). The enzymatic synthesis of sialic acid and its 9-substituted derivatives and the use of a resulting sialic acid in a different sialylating reaction scheme is disclosed in International application WO 92/16640, published on Oct. 1, 1992, and incorporated herein by reference.

When a galactosyltransferase is used for enzymatic synthesis of an oligosaccharide, the reaction medium will preferably contain, in addition to a galactosyltransferase, donor substrate, acceptor sugar and divalent metal cation, a donor substrate recycling system comprising at least 1 mole of glucose-1-phosphate per each mole of acceptor sugar, a phosphate donor, a kinase capable of transferring phosphate from the phosphate donor to nucleoside diphosphates, and a pyrophosphorylase capable of forming UDP-glucose from UTP and glucose-1-phosphate and catalytic amounts of UDP and a UDP-galactose-4-epimerase. Exemplary galactosyltransferases include α(1,3) galactosyltransferase (E.C. No. 2.4.1.151, see, e.g., Dabkowski et al., *Transplant Proc.* 25: 2921 (1993) and Yamamoto et al., *Nature* 345:229-233 (1990)) and β(1,4) galactosyltransferase (E.C. No. 2.4.1.38).

Oligosaccharides synthesized by other enzymatic methods can also be purified by the methods of the invention. For example, the methods are useful for purifying oligosaccharides produced in non-cyclic or partially cyclic reactions such as simple incubation of an activated saccharide and an appropriate acceptor molecule with a glycosyltransferase under conditions effective to transfer and covalently bond the saccharide to the acceptor molecule. Glycosyltransferases, which include those described in, e.g., U.S. Pat. No. 5,180,674, and International Patent Publication Nos. WO 93/13198 and WO 95/02683, as well the glycosyltransferases encoded by the los locus of *Neisseria* (see, U.S. Pat. No. 5,545,553), can be bound to a cell surface or unbound. Oligosaccharides that can be obtained using these glycosyltransferases include, for example, Galα(1→4)Galβ(1→4)Glc, GlcNAcβ(1,3) Galβ(1,4)Glc, Galβ(1→4)GlcNAcβ(1→3)Galβ(1→4)Glc, and GalNAcβ(1→3)Galβ(1→4)GlcNAcβ(1→3) Galβ (1→4)Glc, among many others.

Among the compounds that one can purify using the described methods are sialic acid and any sugar having a sialic acid moiety. Exemplary species include sialic acid species modified with a linker (e.g., glycyl sialic acid) and with a polymer (e.g., poly(ethylene glycol). Other compounds include sialyl galactosides, including the sialyl lactosides, as well as compounds having the formula:

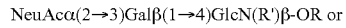

NeuAcα(2→3)Galβ(1→4)GlcN(R')β-OR or

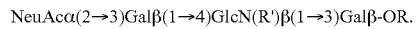

NeuAcα(2→3)Galβ(1→4)GlcN(R')β(1→3)Galβ-OR.

In these formulae, R' is alkyl or acyl from 1-18 carbons, 5,6,7,8-tetrahydro-2-naphthamido; benzamido; 2-naphthamido; 4-aminobenzamido; or 4-nitrobenzamido. R is a hydrogen, a alkyl $C_1$-$C_6$, a saccharide, an oligosaccharide or an aglycon group having at least one carbon atom. The term "aglycon group having at least one carbon atom" refers to a group -A-Z, in which A represents an alkylene group of from 1 to 18 carbon atoms optionally substituted with halogen, thiol, hydroxy, oxygen, sulfur, amino, imino, or alkoxy; and Z is hydrogen, —OH, —SH, —$NH_2$, —$NHR^1$, —$N(R^1)_2$, —$CO_2H$, —$CO_2R^1$, —$CONH_2$, —$CONHR^1$, —$CON(R^1)_2$, —$CONHNH_2$, or —$OR^1$ wherein each $R^1$ is independently alkyl of from 1 to 5 carbon atoms. In addition, R can be:

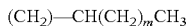

where n, m, and o are independently selected from the integers 1-18; $(CH_2)_n$—$R^2$ (in which n=0-18), wherein $R^2$ is a variously substituted aromatic ring, preferably, a phenyl group, being substituted with one or more alkoxy groups, preferably methoxy or $O(CH_2)_mCH_3$, (in which m=0-18), or a combination thereof. R can also be 3-(3,4,5-trimethoxyphenyl)propyl.

The present invention is also useful for purifying a variety of compounds that comprise selectin-binding carbohydrate moieties. These selectin-binding moieties have the general formula:

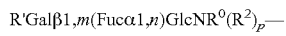

in which $R^0$ is $(C_1$-$C_8$ alkyl)carbonyl, $(C_1$-$C_8$ alkoxy)carbonyl, or $(C_2$-$C_9$ alkenyloxy)carbonyl, $R^1$ is an oligosaccharide or a group having the formula:

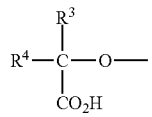

$R^3$ and $R^4$ may be the same or different and may be H, $C_1$-$C_8$ alkyl, hydroxy-($C_1$-$C_8$ alkyl), aryl-($C_1$-$C_8$ alkyl), or ($C_1$-$C_8$ alkoxy)-($C_1$-$C_8$alkyl), substituted or unsubstituted. $R^2$ may be H, $C_1$-$C_8$ alkyl, hydroxy-($C_1$-$C_8$ alkyl), aryl-($C_1$-$C_8$-alkyl), ($C_1$-$C_8$ alkyl)-aryl, alkylthio, α1,2Man, α1,6GalNAc, β1,3Galβ1,4Glc, α1,2Man-$R^8$, α1,6GalNAc—$R^8$, and β1,3Gal-$R^8$. $R^8$ may be H, $C_1$-$C_8$ alkyl, $C_1$-$C_8$ alkoxy, hydroxy-($C_1$-$C_8$ alkyl), aryl-($C_1$-$C_8$ alkyl), ($C_1$-$C_8$ alkyl)-aryl, or alkylthio. In the formula, m and n are integers and may be either 3 or 4; p may be zero or 1.

The substituted groups mentioned above may be substituted by hydroxy, hydroxy($C_1$-$C_4$ alkyl), polyhydroxy($C_1$-$C_4$ alkyl), alkanoamido, or hydroxyalknoamido substituents. Preferred substituents include hydroxy, polyhydroxy($C_3$ alkyl), acetamido and hydroxyacetamido. A substituted radical may have more than one substitution, which may be the same or different.

For embodiments in which $R^1$ is an oligosaccharide, the oligosaccharide is preferably a trisaccharide. Preferred trisaccharides include NeuAcα2,3Galβ1,4GlcNAβ1,3 or Neu-Gcα2,3Galβ1,4GlcNAcβ1,3.

For embodiments in which $R^1$ is the group having the formula

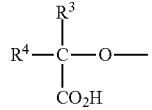

$R^3$ and $R^4$ preferably form a single radical having the formula

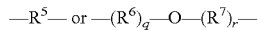

in which $R^5$ is $C_3$-$C_7$ divalent alkyl, substituted or unsubstituted, $R^6$ and $R^7$ are the same or different and are $C_1$-$C_6$ divalent alkyl, substituted or unsubstituted. In the formula, q and r are integers which may be the same or different and are either zero or 1. The sum of q and r is always at least 1.

A more preferred structure for a single radical formed by $R^3$ and $R^4$ is one having the formula

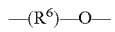

in which $R^6$ is $C_3$-$C_4$ divalent alkyl, substituted or unsubstituted. For instance, $R^6$ may have the formula —$CH_2$—$CH_2$—$CH_2$—$CH_2$—, preferably substituted. The radical can be substituted with hydroxy, polyhydroxy($C_3$ alkyl), and substituted or unsubstituted alkanoamido groups, such as acetamido or hydroxyacetamido. The substituted structure will typically form a monosaccharide, preferably a sialic acid such as NeuAc or NeuGc linked α2,3 to the Gal residue.

In the general formula, above, both m and n are integers and can be either 3 or 4. Thus, in one set of structures Gal is linked β1,4 and Fuc is linked α1,3 to GlcNAc. This formula includes the $SLe^x$ tetrasaccharide. $SLe^x$ has the formula NeuAcα2,3Galβ1,4(Fucα1,3)GlcNAcβ1-. This structure is selectively recognized by LECCAM-bearing cells. $SLe^x$ compounds that can be purified using the methods of the invention include NeuAcα2,3Galβ1,4(Fucα1,3)GlcNAcβ1-Gal-OEt, NeuAcα2,3Galβ1,4(Fucα1,3)GlcNAcβ1,4Galβ1-OEt, and others that are described in international application WO 91/19502. Other compounds that one can purify using the methods include those described in U.S. Pat. No. 5,604,207 having the formula:

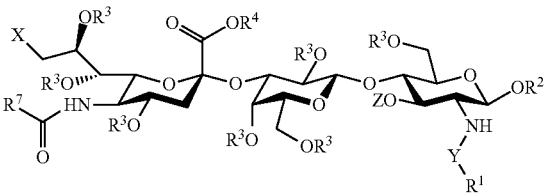

wherein Z is hydrogen, $C_1$-$C_6$ acyl or

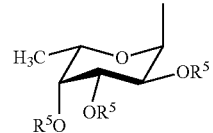

Y is selected from the group consisting of C(O), $SO_2$, HNC(O), OC(O) and SC(O). $R^1$ is selected from the group consisting of an aryl, a substituted aryl and a phenyl $C_1$-$C_3$ alkylene group, wherein said aryl substitutent is selected from the group consisting of a halo, trifluoromethyl, nitro, $C_1$-$C_{18}$ alkyl, $C_1$-$C_{18}$ alkoxy, amino, mono-$C_1$-$C_{18}$ alkylamino, di-$C_1$-$C_{18}$ alkylamino, benzylamino, $C_1$-$C_{18}$ alkylbenzylamino, $C_1$-$C_{18}$ thioaklyl and $C_1$-$C_{18}$ alkyl carboxamido groups, or $R^1Y$ is allyloxycarbonyl or chloroacetyl. $R^2$ is selected from the group consisting of monosaccharide (including β1,3Gal-OR, where R=H, alkyl, aryl or acyl), disaccharide, hydrogen, $C_1$-$C_{18}$ straight chain, branched chain or cyclic hydrocarbyl, $C_1$-$C_6$ alkyl, 3-(3,4,5-trimethoxyphenyl)propyl, $C_1$-$C_5$ alkylene-carboxylate, trisubstituted silyl $C_2$-$C_4$ alkylene wherein said trisubstituted silyl is a silyl group having three substituents independently selected from the group consisting of $C_1$-$C_4$ alkyl, phenyl, or $OR^2$ together form a $C_1$-$C_{18}$ straight chain, branched chain or cyclic hydrocarbyl carbamate; $R^3$ is hydrogen or $C_1$-$C_6$ acyl; $R^4$ is hydrogen, $C_1$-$C_6$ alkyl or benzyl. $R^5$ is selected from the group consisting of hydrogen, benzyl, methoxybenzyl, dimethoxybenzyl and $C_1$-$C_6$ acyl. $R^7$ is methyl or hydroxymethyl. X is selected from the group consisting of $C_1$-$C_6$ acyloxy, $C_2$-$C_6$ hydroxylacyloxy, hydroxy, halo and azido.

A related set of structures included in the general formula are those in which Gal is linked β1,3 and Fuc is linked α1,4. For instance, the tetrasaccharide, NeuAcα2,3Galβ1,3 (Fucα1,4)GlcNAcβ1-, termed here SLe$^a$, is recognized by selectin receptors. See, Berg et al., *J. Biol. Chem.*, 266:14869-14872 (1991). In particular, Berg et al. showed that cells transformed with E-selectin cDNA selectively bound neoglycoproteins comprising SLe$^a$.

The methods of the invention are also useful for purifying oligosaccharide compounds having the general formula Galα1,3Gal-, including Galα1,3Galβ1,4Glc(R)β-O—R$^1$, wherein R$^1$ is —(CH$_2$)$_n$—COX, with X=OH, OR$^2$, —NHNH$_2$, R=OH or NAc, and R$^2$ is a hydrogen, a saccharide, an oligosaccharide or an aglycon group having at least one carbon atom, and n=an integer from 2 to 18, more preferably from 2 to 10. For example, one can purify a compound having the formula Galα1,3Galβ1,4GlcNAcβ-O—(CH$_2$)$_5$—COOH using procedures such as those described in Examples 7-8. Also among the compounds that can be purified according to the invention are lacto-N-neotetraose (LNnT), GlcNAcβ1,3Galβ1,4Glc (LNT-2), sialyl(α2,3)-lactose, and sialyl(α2,6)-lactose.

In one embodiment, a modified sialic acid has the following structure:

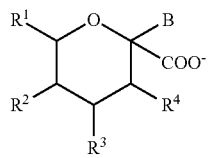

wherein, R$^1$, R$^2$, R$^3$ and R$^4$ are each independently selected from H, OR$^5$, NR$^6$R$^7$, substituted alkyl, unsubstituted alkyl, substituted heteroalkyl and unsubstituted heteroalkyl. R$^5$ is H, substituted alkyl, unsubstituted alkyl, substituted heteroalkyl or unsubstituted heteroalkyl. The symbols R$^6$ and R$^7$ independently represent H, substituted alkyl, unsubstituted alkyl, substituted heteroalkyl and unsubstituted heteroalkyl. B is a nucleoside. Exemplary nucleosides include AMP, UMP, GMP, CMP, TMP, ADP, UDP, GDP, CDP, TDP, ATP, UTP, GTP, CTP, TTP, cAMP and cGMP.

In a preferred embodiment, the sialic acid is modified with a linker group. Preferred sites for such modification are R$^1$ or R$^2$. Thus, in a preferred embodiment, at least one of R$^1$ and R$^2$ includes a linker. An exemplary linker is a glycyl linker.

In a preferred embodiment, the modified sialic acid has the following structure:

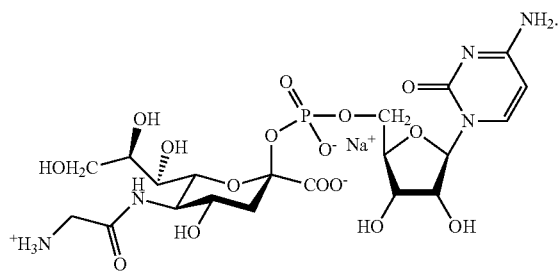

In yet another preferred embodiment, a modifying group is attached to the sialic acid through the linker. An exemplary species according to this description includes a modifying group attached through the free amine moiety of the linker in the figure above. A presently preferred modifying group is a water-soluble polymer. Poly(ethylene glycol) is a preferred water-soluble polymer.

The methods of the invention are useful not only for purifying carbohydrates (and modified carbohydrates and nucleotide sugars) that that are newly synthesized, but also those that are the products of degradation, e.g., enzymatic degradation. See, e.g., Sinnott, M. L., *Chem. Rev.* 90: 1171-1202 (1990) for examples of enzymes that catalyze degradation of oligosaccharides.

The invention also provides methods for purifying nucleotides, nucleotide sugars, and related compounds. For example, a nucleotide sugar such as GDP-fucose, GDP-mannose, CMP-NeuAc, UDP-glucose, UDP-galactose, UDP-N-acetylgalactosamine, and the like, can be purified by the methods described herein. The methods are also useful for purifying nucleotides and nucleotides in various states of phosphorylation (e.g., CMP, CDP, CTP, GMP, GDP, GTP, TMP, TDP, TTP, AMP, ADP, ATP, UMP, UDP, UTP), as well as the deoxy forms of these and other nucleotides, including modified nucleotides. The method of the invention can be used to prepare and purify nucleotide sugars to a high degree of purity on a multi-kilogram scale (e.g., at least about 1 kg, preferably at least about 1.5 kg, more preferably at least about 2 kg, and even more preferably, at least about 3 kg of purified sugar nucleotide per synthesis/purification run). An exemplary process flow chart is set forth in FIG. 1.

In the discussion that follows, focus is placed on the purification of nucleotide sugars. The methods set forth hereinbelow are equally applicable to the purification of sugars, modified sugars and modified nucleotides sugars (e.g., those bearing a linker arm (e.g., a glycl linker arm), a modifying group (e.g., a water-soluble polymer (e.g., PEG)), or a modifying group attached to the linker arm (e.g., PEG attached to the sugar through a glycyl linker).

The process of the invention routinely provides nucleotide sugars, e.g., CMP-NAN, in recovered yields of purified materials in greater that 40%, e.g., of from about 40% to about 80%. In a preferred embodiment, the yield of isolated CMP-NAN is from about 50% to about 70% of the theoretical synthesis yield.

In general, the process of the invention provides nucleotide sugars that are at least 80% pure, preferably at least 85% pure, more preferably, at least 90% pure and still more preferably, at least 95% pure.

In a representative embodiment, the nucleotide sugar is a CMP-sialic acid, e.g., CMP-NAN (N-acetylneuraminic acid). The generic process for purification of nucleotide sugars is exemplified in the context of CMP-sialic acid, however, this focus is for clarity of illustration and should not be construed as limiting the process to practice with CMP-sialic acids.

In a preferred embodiment, a membrane-based methodology is utilized to purify the nucleotide sugar from reaction components. In the case of CMP-sialic acid, exemplary reaction components include cytidine monophosphate and its active analogues, and cytidine diphosphate, unreacted sialic acid, salts (e.g., $PO_4^{3-}$, $Mn^{2+}$).

In a preferred embodiment, the amount of CMP, CDP and/or CTP of the product is less than about 20%, preferably, less than about 15%, more preferably, less than about 10% and still more preferably less than 5%.

In another preferred embodiment, the content of unreacted sialic acid, e.g., NAN, in the final product is less than about than about 20%, preferably, less than about 15%, more preferably, less than about 10%, still more preferably, less than about 5% and even more preferably, less than about 2%.

In yet another preferred embodiment, the phosphate content of the final product is less than about 5%, preferably, less than about 2%, and more preferably, about 0%.

The invention also provides methods for synthesizing and purifying nucleotide sugars. The nucleotide sugar is enzymatically synthesized from a nucleotide and a sugar in the presence of an enzyme. After the nucleotide sugar is synthesized, the nucleotide sugar is purified according to a method of the invention.

In one embodiment, following synthesis, a nucleotide sugar solution is optionally clarified by filtration. The nucleotide sugar solution passes through a membrane bag filter in which contaminating salts and other undesired contaminants are filtered out of the nucleotide sugar solution. The clarification step can be incorporated at any step of the process. In a preferred embodiment, the nucleotide sugar solution is clarified after synthesis of the nucleotide sugar. The nucleotide sugar solution may be clarified one or more times.

In another embodiment, the nucleotide sugar solution is purified using hollow fiber filtration. Hollow fiber filtration removes proteins introduced by the enzyme preparation of the nucleotide sugar. The hollow fiber membrane retains proteins from the enzyme preparation while allowing for passage of the nucleotide sugar solution through the membrane. In an exemplary embodiment, the hollow fiber membrane comprises a hollow fiber membrane with a tangential filtration skid. The hollow fiber filtration step can be incorporated at any step of the process. In one embodiment, the nucleotide sugar solution goes through hollow fiber filtration after clarification. In another embodiment, the nucleotide sugar solution goes through hollow fiber filtration after synthesis of the nucleotide sugar. The nucleotide sugar solution may be filtered one or more times using hollow fiber filtration.

In another embodiment, the nucleotide sugar solution is purified using nanofiltration. Nanofiltration removes salts and other low molecular weight components from a mixture. Nanofiltration membranes separate molecules based on molecular weight and ionic charge. Molecular weight-cutoffs for non-ionized molecules are typically in the range from 100-20,000 daltons. In an exemplary application, saccharides of interest will be retained by the nanofiltration membrane and contaminating salts and other undesired components will pass through. The nanofiltration step can be incorporated at any step of the process. In one embodiment, the nucleotide sugar solution goes through hollow-fiber filtration first and then nanofiltration. In another embodiment, the nucleotide sugar solution goes through nanofiltration first and then hollow fiber filtration. In the alternative, the nucleotide sugar solution may be purified using either hollow-fiber filtration or nanofiltration. In another embodiment, the nucleotide sugar solution goes through nanofiltration after clarification. In yet another embodiment, the nucleotide sugar solution goes through nanofiltration after synthesis of the nucleotide sugar. The nucleotide sugar solution may be filtered one or more times using nanofiltration. After nanofiltration, the purified nucleotide sugar solution may generally be stored or may undergo further purification.

In another embodiment, the nucleotide sugar solution may optionally be decolorized (e.g., by passing the solution over activate carbon). In a preferred embodiment, decolorization involves passing the nucleotide sugar solution over a pre-packed column of activated carbon attached to a chromatography system. Decolorization can be incorporated at any step of the process. In one embodiment, the nucleotide sugar solution is decolorized after nanofiltration. In another embodiment, the nucleotide sugar solution is decolorized after hollow-fiber filtration. In yet another embodiment, the nucleotide sugar solution is decolorized after clarification. The nucleotide sugar solution may be decolorized one or more times.

In another embodiment, the nucleotide sugar solution is purified using a charged depth media filter. The charged depth media filter removes endotoxins from the nucleotide sugar solution. Endotoxins are toxic, natural compounds such as lipopolysaccharides found inside pathogens on the outer cell wall of bacteria. Purification by a charged depth media filter can be incorporated at any step of the process. In one embodiment, the nucleotide sugar solution is filtered after decolorization. In another embodiment, the nucleotide sugar solution is purified by a charged depth media filter after nanofiltration. In yet another embodiment, the nucleotide sugar solution is purified by a charged depth media filter after hollow-fiber filtration. In another embodiment, the nucleotide sugar solution is purified by a charged depth media filter after clarification. In another embodiment, the nucleotide sugar solution is purified by a charged depth media filter after synthesis of the nucleotide sugar. The nucleotide sugar solution may be filtered one or more times using a charged depth media filter.

In another embodiment, the nucleotide sugar solution is purified using a sterile filter. The sterile filter removes contaminating salts and other undesired contaminants from the nucleotide sugar solution. In a more preferred embodiment, the sterile filter is pre-packaged and sterilized with a bag manifold system for final filtration and storage. Purification by a sterile filter can be incorporated at any step of the process. In one embodiment, the nucleotide sugar solution is filtered by a sterile filter after purification by a charged depth media filter. In another embodiment, the nucleotide sugar solution is purified by a sterile filter after decolorization. In yet another embodiment, the nucleotide sugar solution is purified by a sterile filter after nanofiltration. In another embodiment, the nucleotide sugar solution is purified by a sterile filter after hollow fiber filtration. In another embodiment, the nucleotide sugar solution is purified by a sterile filter after clarification. In another embodiment, the nucleotide sugar solution is purified by a sterile filter after synthesis of the nucleotide sugar. The nucleotide sugar solution may be filtered one or more times using a sterile filter.

An exemplary process of nucleotide sugar purification is described in FIG. 1. The nucleotide sugar is first synthesized (1) from a nucleotide and a sugar in the presence of an enzyme.

After the nucleotide sugar is synthesized, the nucleotide sugar is clarified by filtration (2) and transferred into a mobile tank (3). The clarified nucleotide sugar solution is concentrated using a hollow fiber filtration unit with a tangential flow filtration skid and diafiltered with purified water (4) and (5). The nucleotide sugar solution is transferred to a mobile tank (6) and the pH is adjusted.

The purified solution is concentrated again and diafiltered with purified water using a nanofiltration system (7) and (8). The nucleotide sugar solution is then decolorized in which the color is removed from the nucleotide sugar solution (9).

The nucleotide sugar solution subsequently undergoes two filtrations. First, the nucleotide sugar solution is filtered using a charged depth media filter in which endotoxins are removed (10). In an exemplary embodiment, the charged depth media filter is a CUNO Zeta Plus 60 ZA filter or an equivalent. After the nucleotide sugar solution is filtered through the charged depth media filter, the nucleotide sugar solution is optionally filtered using a 0.2 μm sterile filter (11). In an exemplary embodiment, the sterile filter is a CUNO LifeASSURE 0.2

μm sterile filter or an equivalent. The purified nucleotide sugar solution is appropriate for storage.

Exemplary nucleotide sugars that can be purified by the method described above include, but are not limited to, CMP-NAN, GDP-fucose, GDP-mannose, CMP-NeuAc, UDP-Glucose, UDP-galactose and UDP-N-acetylgalactosamine, and modified analogues thereof. In a preferred embodiment, the nucleotide sugar is CMP-NAN or a modified CMP-NAN.

The invention also provides methods for synthesizing and purification of a nucleotide-Glycyl Sialic Acid ("nucleotide-GSC").

In one embodiment, the synthesis of the nucleotide-GSC begins with the synthesis of the protected Fmoc-glycyl-mannosamine ("FGM"). In an exemplary embodiment, mannosamine and Fmoc-Glycyl-OSU are reacted in an aqueous solution under basic conditions. The aqueous solution may contain a base, e.g., sodium methoxide and an organic cosolvent, e.g., methanol, to facilitate the reaction.

The FGM is optionally purified. In an exemplary embodiment, FGM is purified by chromatography, e.g., silica gel chromatography. FGM may be chromatographed one or more times.

In another embodiment, FGM converted to the corresponding sialic acid analogue by reaction with pyruvate to form Fmoc-glycyl-sialic acid ("FSC"). This reaction is efficiently catalyzed by a sialic acid aldolase. Appropriate sialic acid aldolases are commercially available. In an exemplary embodiment, the reaction mixture includes at least the nucleotide, the aldolase, $MnCl_2$ and water. The resulting FSC is then coupled to a nucleotide in the presence of an enzyme to form the resulting product, nucleotide-FSC.

The nucleotide-FSC is optionally purified. In an exemplary embodiment, the nucleotide-FSC is purified by chromatography, e.g., reverse phase chromatography. In an exemplary embodiment, the reverse phase chromatography is C18 reverse phase chromatography. The nucleotide FSC can be filtered (e.g., 0.22 filter) prior to and/or after chromatography.

The nucleotide-FSC is preferably deprotected to produce the free amine analogue of the linker-nucleotide sugar construct. In an exemplary embodiment, deprotection is effected with methanol:water:dimethylamine. Deprotection results in a modified sialic acid, nucleotide-Glycyl-Sialic Acid ("GSC").

The GSC is optionally purified, filtered and/or lyophilized.

Figure 4:
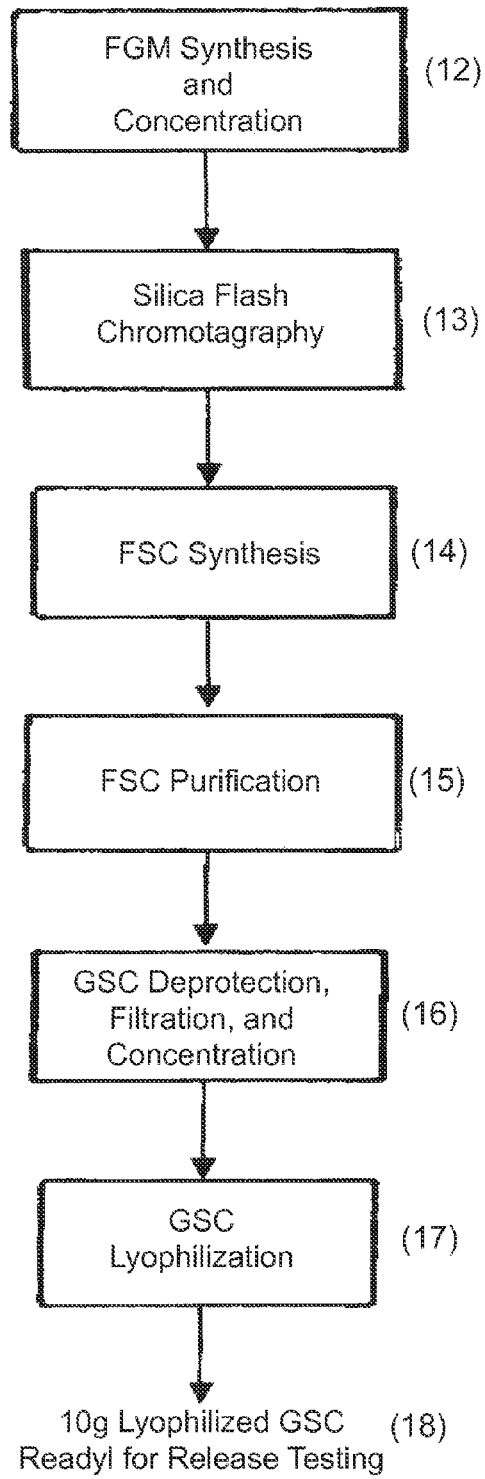
FIG. 4 is a diagram outlining an exemplary process for the preparation of an exemplary GSC(CMP-5'-Glycyl-Sialic Acid).

An exemplary process for nucleotide-GSC synthesis and purification is described in FIG. 4.

The synthesis of nucleotide-GSC begins with the synthesis and concentration of FGM (12). FGM is then purified using silica flash column chromatography (13). FGM is reacted with pyruvate to form FSC (14). The resulting FSC is then coupled to a nucleotide in the presence of an enzyme to form the resulting product, nucleotide-FSC (14). The nucleotide-FSC is then purified (15). The nucleotide-FSC is deprotected (16) thus cleaving off the Fmoc group from the nucleotide-FSC. The resultant product is a nucleotide-GSC. The nucleotide-GSC is further purified and concentrated (16). The nucleotide-GSC is then lyophilized (17) and subsequently released for testing (18).

An exemplary nucleotide that can be used for the synthesis and purification of a nucleotide-GSC includes, but is not limited to, CMP, CDP, CTP, GMP, GDP, GTP, TMP, TDP, TTP, AMP, ADP, ATP, UMP, UDP, UTP, as well as the deoxy Ruins of these and other nucleotides. In a preferred embodiment, the nucleotide is CMP.

The invention provides also methods for synthesizing and purification of a nucleotide-Sialic Acid ("SA")—PEG. In one embodiment, the synthesis of the nucleotide-SA-PEG begins with Fmoc-glycyl-mannosamine ("FGM"). Synthesis and purification of this starting material is discussed above. GSC and methoxy-paranitrophenyl-carbomate-polyethylene glycol ("mPEG-pNP") are combined in under conditions suitable to allow formation of a conjugate between the PEG and the free amine of the glycyl linker. In a preferred embodiment, the synthesis reaction is performed in a 80% THF: 20% $H_2O$ solution.

In another embodiment, the nucleotide-SA-PEG is purified. In a preferred embodiment, the nucleotide-SA-PEG is purified by reverse phase chromatography.

Figure 5:
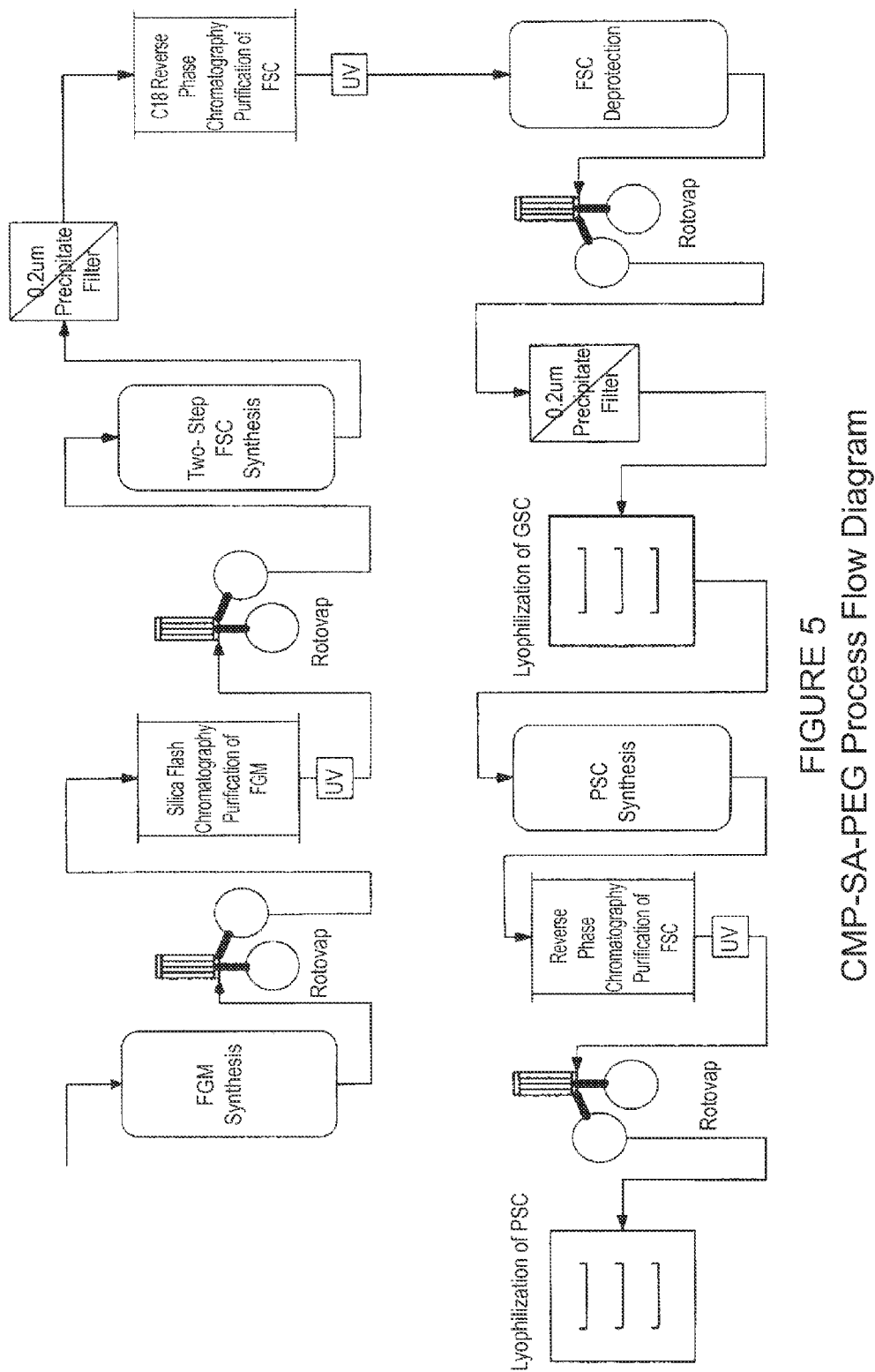
FIG. 5 is a diagram outlining an exemplary process for the preparation of an exemplary PSC(CMP-SA-PEG).

An exemplary process of nucleotide-SA-PEG ("PSC") synthesis and purification is described in FIG. 5.

The synthesis of nucleotide-SA-PEG begins with the synthesis of FGM (19). FGM is rotovapped (20). FGM is then purified using silica column chromatography (21). FGM is detected by a UV light (22) and rotovapped (23). FGM is reacted with pyruvate to form FSC (24). The resulting FSC is then coupled to a nucleotide in the presence of an enzyme to form the resulting product, nucleotide-FSC (24). The nucleotide-FSC is then purified using a 0.2 μm filter (25) and a C18 reverse phase chromatography (26). The solution is then detected by a UV ray (27). The nucleotide-FSC is deprotected (28) thus cleaving off the Fmoc group from the nucleotide-FSC. The resultant product is a nucleotide-GSC. The nucleotide-GSC is rotovapped (29). The nucleotide-GSC is further purified (30) by a 0.2 μm filter. The nucleotide-GSC is then lyophilized (31). The nucleotide-GSC is reacted with a mPEG-pNP to form nucleotide-SA-PEG ("PSC") (32). The PSC is purified by reverse phase chromatography (33). The PSC is detected by UV light (34) and rotovapped (35). The PSC is then lyophilized (36).

An exemplary nucleotide that can be used for the synthesis and purification of a nucleotide-SA-PEG includes, but is not limited to, CMP, CDP, CTP, GMP, GDP, GTP, TMP, TDP, TTP, AMP, ADP, ATP, UMP, UDP, UTP, as well as the deoxy forms of these and other nucleotides. In a preferred embodiment, the nucleotide is CMP.

The invention further provides methods for purifying a glycosyltransferase. In one embodiment, a glycosyltransferase solution is harvested, isolating the enzyme from cell culture and other debris to produce a suitable feed material for subsequent purification steps. In an exemplary embodiment, the harvesting reaction occurs at about pH 6. The harvesting step can be incorporated at any step of the process.

The glycosyltransferase is optionally precipitated from the solution. In an exemplary embodiment, the glycosyltransferase is precipitated by addition of calcium chloride ("$CaCl_2$") to the solution. The pH of the solution can be adjusted as appropriate. In an exemplary embodiment, the pH of the precipitation reaction is adjusted to about 7.5.

The mixture can be incubated for any suitable time under appropriate conditions. In an exemplary embodiment, the precipitation step lasts for about 30 minutes at about 4° C. Other exemplary additives include EDTA.

The recovery of glycosyltransferase after precipitation is about 80% to about 100%, preferably from about 90% to about 100%, even more preferably about 100%.

In another embodiment, the glycosyltransferase solution is subjected to membrane filtration. Exemplary membrane filters have a pore size of about 0.1 μm to about 0.5 μm, preferably about 0.1 μm to about 0.3 μm, and more preferably about 0.20 μm to about 0.25 μm. The filtration step can be incorporated at any step of the process.

In another embodiment, the glycosyltransferase solution is ultrafiltrated. In ultrafiltration, products of high molecular weight are retained on the membrane, while low molecular weight solutes pass through the membrane. In an exemplary embodiment, the ultrafiltration membrane has a molecular weight cut-off (MWCO) between about 5 kDa and about 200 kDa.

In an exemplary embodiment, the glycosyltransferase solution is equilibrated with 15 mM sodium phosphate buffer, pH 7.5 and conductivity is 2 ms/cm. In another embodiment, the glycosyltransferase solution is equilibrated with 15 mM sodium phosphate, pH 7.5. In another embodiment, the glycosyltransferase solution is equilibrated with 15 mM sodium phosphate, 0.01M NaCl, pH 7.5. In another embodiment, the glycosyltransferase is equilibrated with 15 mM sodium phosphate, 0.05M NaCl, pH 7.5. In another embodiment, the glycosyltransferase solution is equilibrated with 15 mM sodium phosphate, 0.10M NaCl, pH 7.5. In another embodiment, the pH range of the sodium phosphate may range from about 5.5 to about 8.5. In a preferred embodiment, the pH range of the glycosyltransferase solution may range from about 6.5 to about 7.5. In another embodiment, the test excipient includes, but is not limited to, glycerol, mannitol, sorbitol, sucrose and Tween-20. In one embodiment, the percent recovery of glycosyltransferase after ultrafiltration is about 45% to about 85%. In a preferred embodiment, the percent recovery of glycosyltransferase after ultrafiltration is about 55% to about 75%. In a more preferred embodiment, the percent recovery of glycosyltransferase after ultrafiltration is about 65%. The ultrafiltration step can be incorporated at any step of the process. In a preferred embodiment, the glycosyltransferase solution is ultrafiltrated after the filtration step. In another preferred embodiment, the glycosyltransferase solution is ultrafiltrated after the precipitation step. In another preferred embodiment, the glycosyltransferase solution is ultrafiltrated after the harvesting step. The glycosyltransferase solution may be ultrafiltrated one or more times.

In another embodiment, the glycosyltransferase is purified by chromatography, e.g., ion exchange chromatography. In an exemplary embodiment, the glycosyltransferase is purified using an anion exchange column. In a further exemplary embodiment, the anion exchange column is a Mustang Q or an equivalent. The recovery of glycosyltransferase after anion exchange chromatography is preferably from about 80% to about 100%. In a preferred embodiment, the recovery of glycosyltransferase after chromatography is about 90% to about 100%. In a more preferred embodiment, the recovery of glycosyltransferase after chromatography is about 100%. The chromatography step can be incorporated at any step of the process. In a preferred embodiment, the glycosyltransferase is purified by chromatography after an ultrafiltration step. In a preferred embodiment, the glycosyltransferase is purified by chromatography after the filtration step. In another preferred embodiment, the glycosyltransferase is purified by chromatography after the precipitation step. In another preferred embodiment, the glycosyltransferase is purified by chromatography after the harvesting step.

In another exemplary embodiment, the glycosyltransferase solution purified using a cation exchange column. An exemplary cation exchange chromatography protocol utilizes a Unosphere S resin or an equivalent. In a preferred embodiment, the cation exchange column is a 30S or an equivalent.

The cation exchange column is eluted with at least one buffer. In one embodiment, the first buffer comprises a 15 mM sodium phosphate, pH 7.5. In another embodiment, the column is further eluted with a second buffer. An exemplary second buffer includes 1M NaCl, 15 mM sodium phosphate, pH 7.5.

Elution of the column is optionally performed while developing a eluant gradient. In an exemplary embodiment, the added elution step has a rate of about 5 ms/cm to about 10 ms/cm. The recovery of glycosyltransferase after cation exchange chromatography is about 35% to about 75%. In a preferred embodiment, the recovery of glycosyltransferase after chromatography is about 45% to about 65%. In a more preferred embodiment, the percent recovery of glycosyltransferase after chromatography is about 55%. The chromatography step can be incorporated at any step of the process. In a preferred embodiment, the glycosyltransferase is purified by cation exchange chromatography after the anion exchange chromatography step described in the immediately preceding paragraph. In a preferred embodiment, the glycosyltransferase is purified by anion or cation exchange chromatography after the ultrafiltration step. In another preferred embodiment, the glycosyltransferase is purified by ion exchange chromatography after the filtration step. In yet another preferred embodiment, the glycosyltransferase is purified by chromatography after the precipitation step. In another preferred embodiment, the glycosyltransferase solution is purified by chromatography after the harvesting step. The glycosyltransferase solution may be purified by chromatography one or more times.

In an exemplary embodiment, the glycosyltransferase is purified by hydroxyapatite (HA) chromatography. Exemplary hydroxyapatite sorbents are selected from ceramic and crystalline hydroxyapatite materials. In an exemplary embodiment the particle size of the ceramic hydroxyapatite sorbent is between about 20 μm and about 180 μm, preferably about 60 to about 100 μm, and, more preferably about 80 μm. In a preferred embodiment, the recovery of glycosyltransferase after HA chromatography is about 50% to about 90%, preferably from about 60% to about 90%. In a more preferred embodiment, the percent recovery of glycosyltransferase after chromatography is about 72%. HA chromatography can be incorporated at any step of the process. In a preferred embodiment, the glycosyltransferase is purified by HA chromatography after the cation chromatography step described above in the immediately preceding paragraph. In a preferred embodiment, the glycosyltransferase is purified by HA chromatography after the anion exchange chromatography step described above. In another preferred embodiment, the glycosyltransferase is purified by HA chromatography after the ultrafiltration step. In still another preferred embodiment, the glycosyltransferase is purified by HA chromatography after the filtration step. In another preferred embodiment, the glycosyltransferase is purified by HA chromatography after the precipitation step. In another preferred embodiment, the glycosyltransferase is purified by HA chromatography after the harvesting step. The glycosyltransferase solution may be purified by HA chromatography one or more times.

In another exemplary embodiment, the glycosyltransferase is purified by hydrophobic interaction chromatography ("HIC"). In an exemplary embodiment, the hydrophobic moieties of the column matrix are selected from, but are not limited to, alkyl groups, aromatic groups and ethers. In an exemplary embodiment, the HIC column is packed with a phenyl 650M resin, butyl 650M resin, phenyl HP resin.

In an exemplary embodiment, the glycosyltransferase solution is equilibrated with 0.5M ammonium sulfate, 20 mM sodium phosphate, pH 7.

HIC chromatography can be incorporated at any step of the process. In a preferred embodiment, the glycosyltransferase is purified by HIC chromatography after purification by the HA chromatography step described above in the immediately preceding paragraph. In a preferred embodiment, the glycosyltransferase is purified by chromatography after the cation exchange chromatography step described above. In another preferred embodiment, the glycosyltransferase is purified by chromatography after the anion exchange chromatography step described above. In a preferred embodiment, the glycosyltransferase solution is purified by chromatography after the ultrafiltration step. In a preferred embodiment, the glycosyltransferase solution is purified by chromatography after the filtration step. In another preferred embodiment, the glycosyltransferase solution is purified by chromatography after the precipitation step. In another preferred embodiment, the glycosyltransferase solution is purified by chromatography after the harvesting step. The glycosyltransferase solution may be purified by chromatography one or more times.

The glycosyltransferase can be purified by ultrafiltration. In an exemplary embodiment, the glycosyltransferase solution is equilibrated with 50 mM Bis-Tris, 0.1M NaCl, 5% sorbitol, pH 6.5. It is generally preferred that the recovery of glycosyltransferase after ultrafiltration is about 80% to about 100%. In a preferred embodiment, the percent recovery of glycosyltransferase after chromatography is about 90% to about 100%.

Ultrafiltration can be incorporated at any step of the process. In a preferred embodiment, the glycosyltransferase is purified by ultrafiltration after the HIC chromatography step in the immediately preceding paragraph described above. In a preferred embodiment, the glycosyltransferase is purified by ultrafiltration after purification by the HA chromatography step described in the preceding paragraph above. In another preferred embodiment, the glycosyltransferase is purified by ultrafiltration after the cation exchange chromatography step described above. In still a further preferred embodiment, the glycosyltransferase is purified by ultrafiltration after the anion exchange chromatography step described above. In another embodiment, the glycosyltransferase is purified by a second ultrafiltration step after the first ultrafiltration step described above. The glycosyltransferase can be purified by ultrafiltration after the filtration step or precipitation steps. In still another embodiment, the glycosyltransferase is purified by ultrafiltration after the harvesting step. The glycosyltransferase may be purified by ultrafiltration one or more times.

In another embodiment, the total percent recovery of glycosyltransferase from the purification process is about 5% to about 45%. In a preferred embodiment, the percent recovery of glycosyltransferase from the purification process is about 15% to about 35%.

Figure 6:
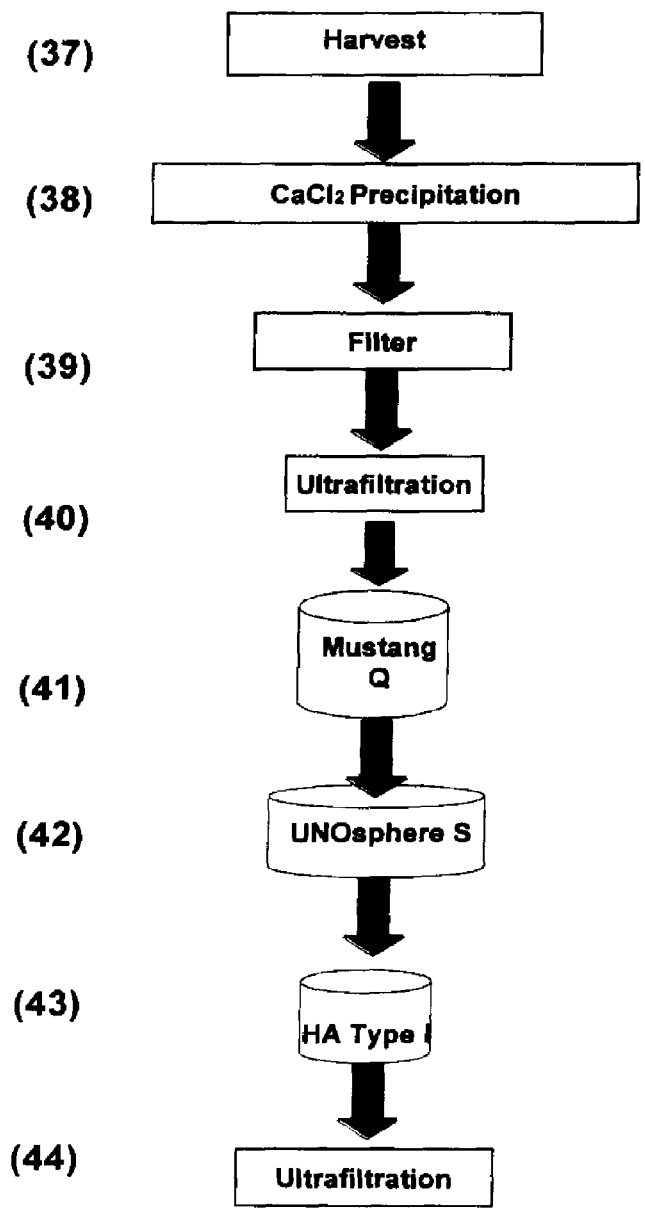
FIG. 6 is a diagram outlining an exemplary process for the purification of a glycosyltransferase.

An exemplary process of a glycosyltransferase purification scheme is described in FIG. 6. The glycosyltransferase is first harvested (37). In an exemplary embodiment, the harvesting reaction takes place at pH 6. After harvesting, the glycosyltransferase is precipitated using calcium chloride (38). The glycosyltransferase is then filtered (39). After filtration, the glycosyltransferase undergoes ultrafiltration (40). The glycosyltransferase passes through an anion exchange column such as Mustang Q (41) or an equivalent. After passing through the anion exchange column, the glycosyltransferase passes through a cation exchange column, such as UNOsphere S (42) or an equivalent. The glycosyltransferase is then passed through a HA Type I chromatography column (43). The glycosyltransferase then undergoes ultrafiltration (44).

In one embodiment, the glycosyltransferase is a sialyltransferase. In a more preferred embodiment, the sialyltransferase includes, but is not limited to, ST6GalNac, ST3Gal3, α(2,3)-sialyltransferase, α(2,6)-sialyltransferase and α(2,8)-sialyltransferase. In another embodiment, the sialyltransferase includes, but is not limited to, a sialyltranferase listed in the table in FIG. 7. In a more preferred embodiment, the sialyltransferase is ST6GalNac.

The following examples are offered solely for the purposes of illustration, and are intended neither to limit nor to define the invention.

EXAMPLES

Example 1

Fmoc-Glycyl-Mannosamine Synthesis and Purification

The synthesis of Fmoc-glycyl-mannosamine (FGM) occurred in a non-aqueous solution involving two main compounds: D-Mannosamine HCl and Fmoc-Glycyl-OSu. Both materials were dry powders that were introduced into a system comprised of anhydrous methanol and sodium methoxide. The reaction was agitated at 25° C. for 1 h The reaction was complete when the FGM concentration was greater than 15 mg/mL, determined by HPLC. The FGM synthesis was then rotovapped (20° C.) to about 8% of the initial volume. The chromatographic purification was performed using a Biotage pre-packed silica column. The FGM solution was loaded onto the column in a 50:50 $CHCl_3:CH_3OH$ solution. The silica column was then washed with 18 column volumes (CV) of 3% $CHCl_3$/97% $CH_3OH$. Following the wash, FGM was eluted from the column using 14 CV of 15% $CHCl_3$/85% $CH_3OH$. Fractions containing material were pooled and then rotovapped (20° C.) to dryness and stored at 4° C. The average recovery for this step from the consistency batches was 73.8%.

Raw Materials: The table below lists the materials used during the synthesis and purification of Fmoc-Glycyl-Mannosamine (FGM). The first four reagents in the table were used during the synthesis of FGM. The last two reagents were used during the purification of FGM.

| | |
|---|---|
| D-Mannosamine HCl | 9.0 g |
| Fmoc-Glycyl-OSu | 36.2 g |
| Sodium Methoxide, 0.5M | 184 mL |
| Anhydrous Methanol | 726 mL |
| Methanol, ACS | 1.4 L |
| Chloroform, ACS | 16.2 L |

The silica column was a Biotage 75M Silica column. The column volume for a 75M column was 0.5 L.

Example 2

I. Description of CMP-Glycyl-Sialic Acid and CMP-Sialic Acid-PEG Synthesis and Purification The production of CMP-Sialic Acid-PEG (PSC) was performed in two segments. First, a key intermediate, CMP-Glycyl-Sialic Acid (GSC), was synthesized, purified, and dried, and second, this intermediate was PEGylated, purified, and dried. A synthetic pathway for CMP-SA-PEG is shown below.

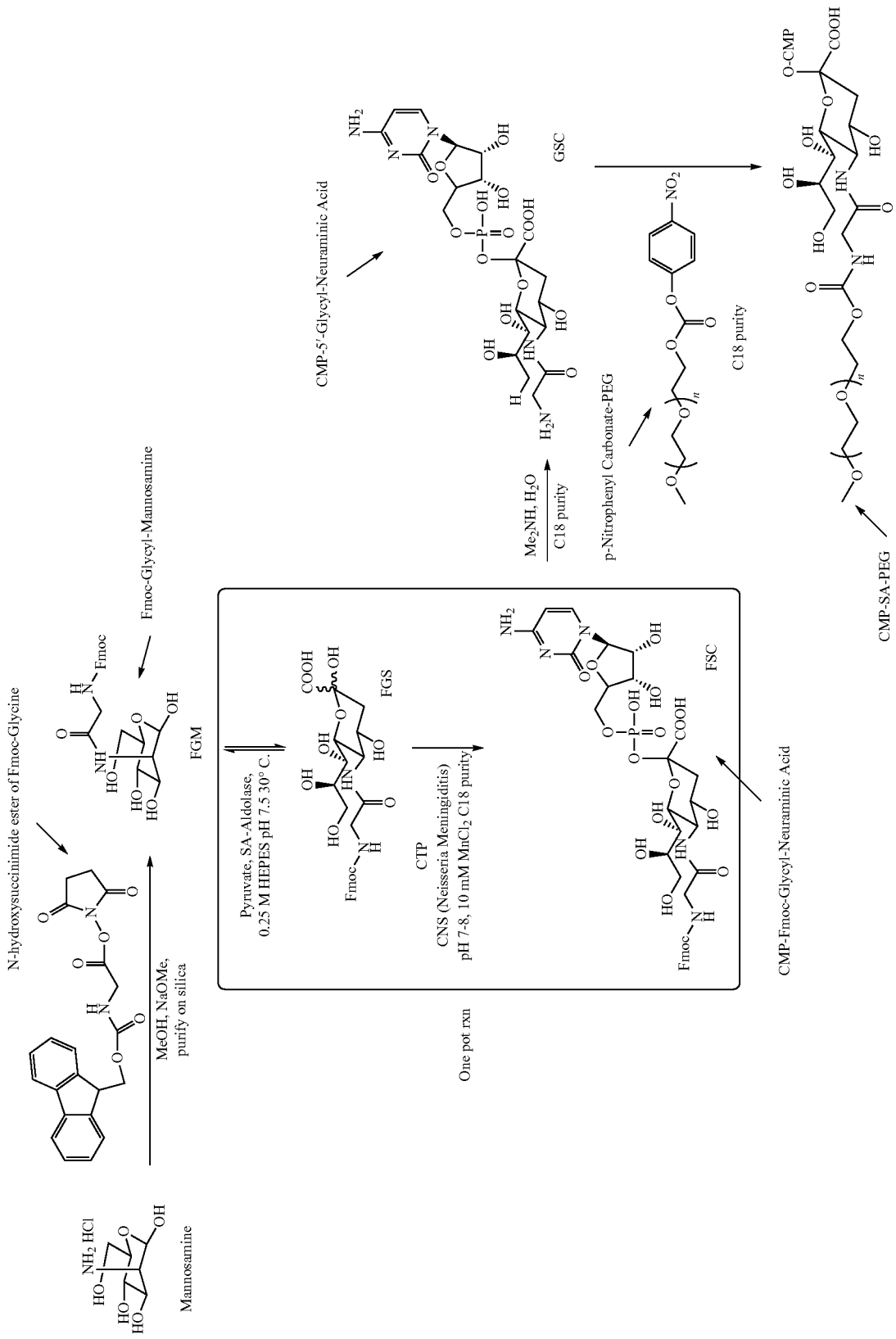

The first step in the synthesis of GSC was the reaction of mannosamine with Fmoc-Gly-OSu in methanol under basic conditions. The resulting Fmoc-glycyl-mannosamine was purified on a silica flash chromatography column. The purified Fmoc-glycyl-mannosamine then entered a two step enzymatic reaction.

Fmoc-glycyl-mannosamine (FGM) was reacted with pyruvate to convert to Fmoc-glycyl-sialic acid. This reaction was catalyzed by a commercially available sialic acid aldolase. Fmoc-glycyl-sialic acid was then coupled to cytidine-5'-monophosphate through a CMP-NAN synthetase catalyzed reaction with cytidine-5'-triphosphate. The resulting product, CMP-Fmoc-glycyl-sialic acid, was purified on a C18 reverse phase column.

Finally, the Fmoc-group was removed from the CMP-Fmoc-glycyl-sialic acid by deprotection with dimethylamine, forming a precipitate. The resulting precipitate was filtered out of solution using a 0.2 μm membrane and discarded. The resulting solution was dried in a freeze dryer, yielding a white powder of CMP-glycyl-sialic acid (GSC).

Both CMP-SA-10K PEG and CMP-SA-20K PEG were synthesized in a single step reaction of GSC with the appropriately sized mPEG-pNP. This reaction was performed in an 80% THF:20% $H_2O$ solution. Purification of the final product, CMP-SA-PEG (PSC), was performed by reverse phase chromatography. CMP-SA-10K PEG was purified using a C8 reverse phase chromatography resin, and CMP-SA-10K PEG was purified using a C4 reverse phase chromatography resin. The eluent from the reverse phase column was dried by lyophilization, yielding a white powder of purified CMP-SA-PEG.

The process was scaled to produce approximately 10 g of the GSC intermediate. Approximately 5.5 g of CMP-SA-20K was produced from 0.5 g of GSC, while approximately 5.0 g of CMP-SA-10K PEG was produced from 1.0 g of GSC. The final CMP-SA-PEG products were approximately 90% pure with the major impurities being CMP and sialic acid-PEG, the primary breakdown products of CMP-SA-PEG.

II. CMP-Fmoc-Glycyl-Sialic Acid Synthesis

Process Description

The synthesis of CMP-Fmoc-glycyl-sialic acid (FSC) was a two-step enzymatic process performed simultaneously in one pot. Reacting with pyruvate, Fmoc-glycyl-mannosamine (FGM) was converted to Fmoc-glycyl-sialic acid, catalyzed by sialic acid-aldolase. Fmoc-glycyl-sialic acid was then coupled to cytidine-5'-monophosphate through a CMP-NAN synthetase catalyzed reaction with cytidine-5'-triphosphate.

The pH of the reaction was controlled at 7.5±0.5. Temperature was controlled at 30±2° C., and the reaction was continuously agitated. The reaction reached completion in 6-24 hrs. and the extent-of-reaction was determined as a function of the FSC concentration (≥14.0 g/L, 95% of theoretical conversion). The resulting product solution can be stored at 4° C. until the purification is executed or for up to 72 h. The average recovery for the step during consistency batches was 91.2%.

The quantities of materials required for the synthesis of CMP-Fmoc-glycyl-sialic acid varied with the quantity of Fmoc-glycyl-mannosamine generated from the purification step of the process. Exemplary quantities are as follows:

| | |
|---|---|
| Fmoc-glycyl-mannosamine | 11 g |
| Cytidine-5'-triphosphate | 15.8 g |
| Manganese Chloride | 9.5 g |
| Pyruvate | 26.4 g |
| Sodium Hydroxide, 50% (w/w) | 17 mL |
| CMP-NAN-Synthetase (N. meningitidis) | 50,600 U |
| N-Acetyneuraminic acid Aldolase | 1.19 g |

III. CMP-Fmoc-Glycyl-Sialic Acid Purification

Process Description

The purification of CMP-Fmoc-glycyl-sialic acid (FSC) consists of two steps: the clarification of the reaction solution by 0.2 μm filtration and the reverse phase chromatographic purification of the FSC. To clarify the reaction, the solution was simply pumped through a Millipore Millipak 0.2 μm filter cartridge. Little backpressure was generated during this filtration. After the filtration was complete, the filter cake and filter were rinsed with 500 mL of purified water.

The chromatographic purification was performed using a Biotage pre-packed C18 reverse phase column. The FSC was loaded in an aqueous solution. The FSC binds to the column, and the column was washed with six column volumes of purified water. The FSC was then eluted in 10% methanol in purified water.

The purification step was performed using the Biotage chromatography system (Z-1405).

IV. CMP-Fmoc-Glycyl-Sialic Acid (FSC) Deprotection and CMP-5'-Glycyl-Sialic Acid (GSC) Filtration Process Description The deprotection of CMP-Fmoc-Glycyl-Sialic Acid (FSC) occurred in a 10% methanol:water solution in a reaction with dimethylamine. Dimethylamine (40 wt % in water) is a solution that was added to the FSC C18 fraction pool. The Fmoc group was cleaved off, resulting in key intermediate, CMP-5'-Glycyl-Sialic Acid (GSC). The reaction was agitated at 25° C. for 75 minutes.

The reaction was complete when the peak area ratio of GSC:FSC was greater than 20, as measured by HPLC. The resulting GSC solution was then rotovapped (30° C.) to about 35% of the original volume. The free Fmoc-derivative formed a white precipitate that needed to be removed from the GSC solution. This material was filtered through a Millipore Millipak—200 Filter Unit (0.22 μm). The filter was then rinsed with RO water. This GSC solution was stored at 4° C. or frozen at −20° C. until lyophilization. The average recovery for this step from the consistency batches was 86.1%.

The table below lists the materials used during the deprotection of CMP-Fmoc-Glycyl-Sialic Acid (FSC) and filtration of CMP-5'-Glycyl-Sialic Acid (GSC).

| Raw Materials for CMP-Glycyl-Sialic Acid (GSC) Deprotection and Filtration | |
|---|---|
| CMP-Fmoc-Glycyl-Sialic Acid (FSC) C18 Fraction Pool | Volume determined from P30 batch record |
| Dimethylamine (40 wt %) | Volume calculated from P40 batch record See Section A, step 1 |
| RO $H_2O$ | Volume calculated from P40 batch record See Section B, step 6 |

V. CMP-SA-Glycine Production

Another method of producing and purifying CMP-SA-Glycine is provided below:

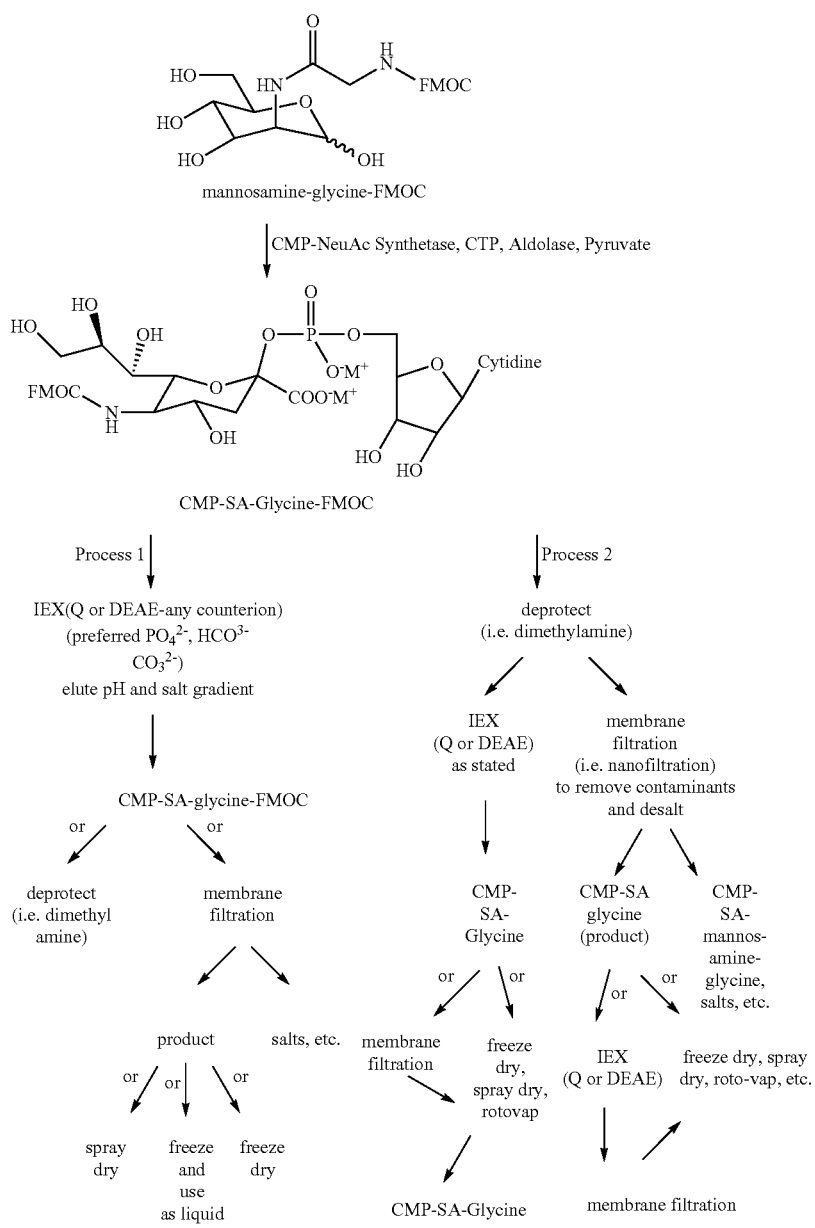

Example 3

I. Summary of Consistency Batches of 10 k And 20 k Cmp-SA-PEG After Process Development Consistency batches were performed for 10K and 20K CMP-Sialic Acid-PEG after development of the synthesis and purification operations. These batches demonstrated that a reproducible process had been developed to produce high-purity CMP-SA-PEG with very low contaminant levels, suitable for the glycopegylation projects.

10K CMP-SA-PEG was produced at greater than 80% purity at overall process yields of approximately 60%, and 20K CMP-SA-PEG was produced at greater than 70% purity at overall process yields of approximately 50%. The products were low in endotoxin, bioburden, and protein, and NMR has shown that the balance of the material was nearly all mPEG-OH, a by-product of the synthesis process.

Materials And Methods

CMP-SA-PEG (PSC) was produced in a reaction of CMP-Glycyl-Sialic Acid (GSC) with paranitrophenyl-carbomate-polyethylene glycol (pNP-PEG). The reaction conditions for the consistency batches of each size CMP-SA-PEG are summarized below.

| CMP-SA-PEG Synthesis Conditions | | |
|---|---|---|
| | 10K PSC | 20K PSC |
| Raw Materials | | |
| CMP-5'-Glycyl-Sialic Acid (GSC) | 1.0 g 10K 10K | 0.5 g 20K 20K |
| pNP-PEG | 24 g 10K pNP-PEG 10K 10K | 24 g 20K pNP-PEG 20K 20K |
| RO $H_2O$ | 200 mL | 100 mL |
| Tetrahydrofuran (THF) unstabilized | 800 mL 10K 10K | 400 mL 20K 20K |
| Reaction Conditions | | |
| Length of Reaction | 24 ± 1 hrs. | 20 ± 1 hrs. |
| pH adjustment to 8.9 ± 0.1 | 17 ± 1 hrs. | 17 ± 1 hrs. |
| Additions of PEG | 3 additions (90 min. between) each of 8 g of pNP-PEG | 3 additions (90 min. between) each of 8 g of pNP-PEG |

At the end of the reaction, a molar ratio of PSC to GSC (product to reactant) of greater than 7:1 is found for 10K PSC and greater than 5:1 for 20K PSC.

The reaction solution were then rotovapped at <30° C. to less than 80% of its original volume to remove the THF. The remaining aqueous solution was then diluted to five times the original reaction volume (diluted to 5 L for 10K PSC and 2.5 L for 20K PSC) using RO water. The diluted solution was then adjusted to pH 9.5±0.1 with 1M NaOH and allowed to stir for at least 1 hr. This elevated pH caused breakdown of residual pNP-PEG to free paranitrophenol, carbon dioxide, and methoxyPEG-OH (mPEG-OH). After at least 1 hr. at the elevated pH, the solution is adjusted to pH 8.0±0.1 using 1M HCl.

Both 10K and 20K PSC were then purified on a C4 reverse-phase chromatography column. The table below summarizes the purification conditions.

| CMP-SA-PEG Purification Conditions | | |
|---|---|---|
| | 10K PSC | 20K PSC |
| Column | Biotage C4 75 L (1 L bed volume, 7.5 cm diameter) | Biotage C4 75 L (1 L bed volume, 7.5 cm diameter) |
| Flowrate | 100 mL/min (136 cm/hr) | 100 mL/min (136 cm/hr) |
| Wash Conditions | 10 column volumes (CVs) 10% MeOH, 1 mL 1M NaOH/L water | 10 CVs 10% MeOH, 1 mL 1M NaOH/L water |
| Elution Conditions | 4 CVs 40% MeOH, 1 mL 1M NaOH/L water | 4CVs 43% MeOH, 1 mL 1M NaOH/L water |
| Regeneration Conditions | 3CVs 100% MeOH 2CVs 50% MeOH, 1 mL 1M NaOH/L water 2CVs 25% MeOH, 1 mL 1M NaOH/L water 3CVs 100% RO water, 1 mL 1M NaOH/L water | 3CVs 100% MeOH 2CVs 50% MeOH, 1 mL 1M NaOH/L water 2CVs 25% MeOH, 1 mL 1M NaOH/L water 3CVs 100% RO water, 1 mL 1M NaOH/L water |

From the column, fractions during the elution that contain UV (27 nm) absorbance of at least 10% of the main peak absorbance were pooled, and the methanol from the pool was removed by rotovap.

This concentrated fraction pool was then freeze dried on a Labconco flask-style freeze-drier. Final testing was performed on the resulting powder from this drying.

Equipment

The syntheses was performed in 2 L and 5 L scaled bottles, temperature controlled in a shaker incubator, SI-0017, B. Braun Certomat BS1.

Chromatographic purification was performed on the Biotage Flash Chromatography System, Z-1405. Drying was performed on a lab-scale Labconco freeze dryer.

Results

Using the methods described above, two batches each of 10K and 20K PSC were synthesized, purified, and dried. The chart below summarizes the yield and recoveries from the synthesis and purification steps of the process. Note that the extent-of-reaction is noted as a ratio of peak areas of PSC to GSC from the HPLC assay. Quantitative yields from the syntheses are not available because the use of THF in the reaction disrupts the quantitative ability of the HPLC method.

| CMP-SA-PEG Consistency Batch Yields and Recovery | | | | | | |
|---|---|---|---|---|---|---|
| | 10K PSC A | 10K PSC B | Average | 20K PSC A | 20K PSC B | Average |
| PSC Synthesis | | | | | | |
| GSC content (wet weight) | 60.66% | 67.38% | | 67.38% | 61.15% | |
| EOR | 13.8:1 | 8.0:1 | | 6.3:1 | 5.4:1 | |
| PSC Purification | | | | | | |
| Quantity (g) | 6.7 | 7.9 | | 5.5 | 7.3 | |
| Yield PSC (g) | 5.5 | 6.6 | 6.1 | 4.2 | 5.5 | 4.8 |
| % Recovery | 59.8% | 64.0% | 61.9% | 42.4% | 60.5% | 51.4% |

Results for the four batches are summarized below.

| PSC Consistency Batch Testing Results | | | | |
|---|---|---|---|---|
| | 10K PSC A | 10K PSC B | 20K PSC A | 20K PSC B |
| Identification (RP-LC) | Match with standard | Match with standard | Match with standard | Match with standard |
| 10K PSC purity (g/100 g of dry wt) | 82.62 | 83.01 | 76.30 | 74.56 |
| CMP (g/100 g of dry wt) | 0.02 | 0.02 | 0.02 | 0.02 |
| Moisture content (g/100 g of wet wt) | 0.60 | 0.49 | 0.52 | 0.48 |
| Sodium % $Na^+$ (g/100 g of wet wt) | 0.45 | 0.50 | 0.22 | 0.14 |
| Aldolase/CNS2 impurity | None visible | None visible | None visible | None visible |
| Endotoxin (EU/mg of wet wt) | 0.011 | 0.007 | 0.0113 | 0.006 |
| Microbial limits testing | *** | *** | *** | *** |

-continued

| PSC Consistency Batch Testing Results | | | | |
|---|---|---|---|---|
| | 10K PSC A | 10K PSC B | 20K PSC A | 20K PSC B |
| Total aerobic counts (CFU/g of wet wt.) | <10 | <10 | <10 | <10 |
| Total yeast and mold (CFU/g of wet wt.) | <10 | <10 | <10 | <10 |

The HPLC traces of the 4 batches showed that the CMP-SA-PEG was >98% by peak area. CMP levels were also very low and much lower than seen in previous lots of PSC.

A silver stain SDS-PAGE gel was run to analyze for residual CNS and aldolase. None was detectable in either the 10K or 20K PSC batches.

Also, as requested in the materials specifications, $^1$H-NMR was performed on the batches.

The 10K PSC samples from Consistency Batch#2 and Consistency Batch#3, were submitted for $^1$H NMR analysis. The NMR spectra indicated that the PSC is reasonably clean, agreeing with the HPLC analysis. There are no observable resonances for sialic acid-PEG (expected at 2.22 & 1.83 ppm) or CMP (distinct resonance expected ~8.11 ppm). A very small amount of PEG-carbamate-DMA (the product of the reaction of dimethylamine with pNP-PEG, ~2.93 ppm) is seen in Batch #2, while none is seen in Batch #3. Although non-quantitative, the ratio of the methyl singlet (3.39 ppm) to the unique PSC resonances (~8.00, 2.50, & 1.55 ppm) is ~1/3, which would indicate relatively low levels of mPEG-OH impurities.

The 20K PSC samples from Consistency Batch#2 and Consistency Batch#3, submitted for $^1$H NMR analysis showed that the PSC is also reasonably clean. There are no observable resonances for sialic acid-PEG (2.22 & 1.83 ppm), CMP (distinct resonance at ~8.11 ppm), or PEG-carbamate-DMA (~2.93 ppm). Although non-quantitative, the ratio of the methyl singlet (3.39 ppm) to the unique PSC resonances (~8.00, 2.50, & 1.55 ppm) is ~1/3, which would indicate relatively low levels of mPEG-OH impurities.

Example 4

Nucleotide Sugar-PEG Purification

General Overview

The current method discusses PEG coupling with a nucleotide sugar, such as CMP-SA-glycine. The nucleotide sugar-PEG product can be separated from the reaction mixture by first desalting the reaction mixture using dialysis. Membrane filtration (reverse osmosis, nanofiltration, etc.) or size exclusion techniques (i.e. polyacrylamide) resin, Sephadex resin, Sepharose resin) can be used next to further purify the mixture. After purification, the reaction mixture containing the nucleotide sugar-PEG product undergoes further purification involving ion exchange chromatography. For most reaction mixtures, a DEAE or Q-resin can be used to remove the unreacted PEG from the product. Q-Sepharose resin is currently preferred, although any polymer with a quaternary amine will also work. The Q-Sepharose resin can include ions such as —OH, Cl$^-$, HCO$_3^-$, CO$_3^{2-}$, PO$_4^{2-}$, SO$_3^-$, Br$^-$, BO$_3^{2-}$ or the like. The product can be loaded and eluted using known methods in the art such as changes in pH or ion strength (NaCl, KCl, etc.). The product may be eluted by a step-wise process or a gradient process. The nucleotide sugar-PEG product eluted from the column can be collected and desalted again using dialysis, membrane filtration, or size-exclusion techniques. The process would look similar to the figure below but can be varied dependent on processing results and desires.

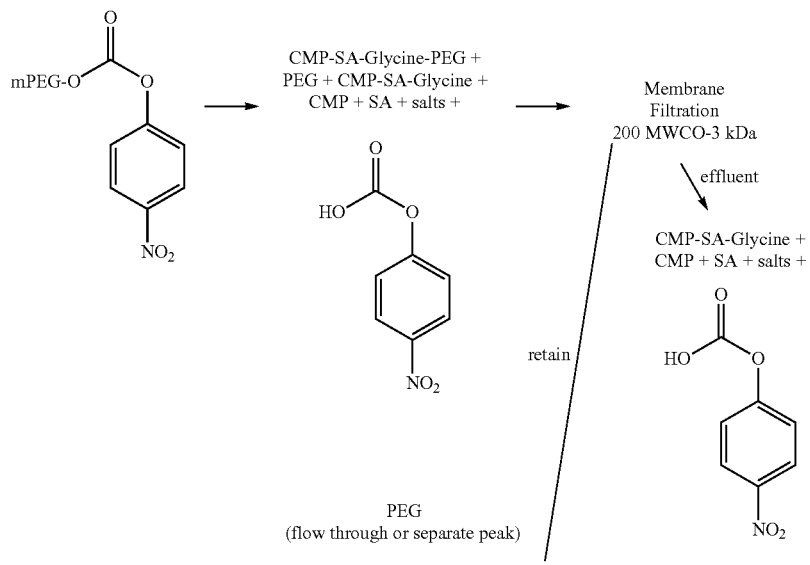

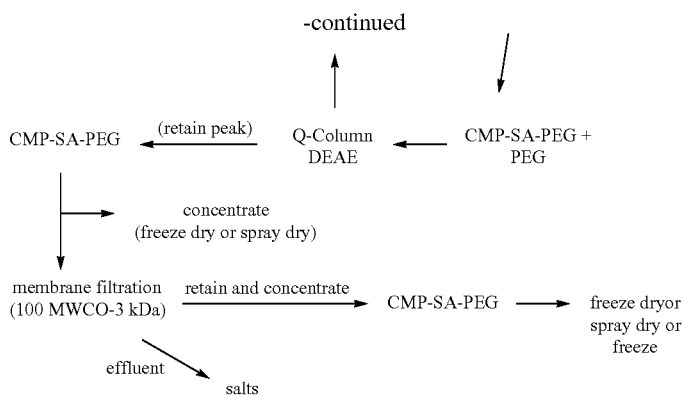

Specific Example

CMP-SA-glycine and the p-nitrophenyl-carbamate-mPEG are mixed together to obtain a reaction mixture comprising the product CMP-SA-glycine-PEG, as well as PEG, p-nitrophenyl-carboxylic acid, salts, CMP-SA-glycine, CMP and sialic acid (SA). The reaction mixture underwent membrane filtration wherein the membrane has MWCO of 200(units)-300 kDa. CMP-SA-PEG and PEG were retained while p-nitrophenyl-carboxylic acid, salts, CMP-SA-glycine, CMP and SA passed through the membrane. The retained products underwent further purification with a Q-column or DEAE column in which PEG flows through the membrane and CMP-SA-PEG is retained and concentrated. At this step, the CMP-SA-PEG may be freeze-dried or spray dried. The CMP-SA-PEG underwent membrane filtration in which salts pass through and while CMP-SA-PEG was retained and concentrated. The membrane has a MWCO of 100 MW-3 kDa. This sample may be freeze dried, spray dried, or frozen.

Any membrane size can be used from reverse osmosis (RO) pore sizes (molecular weight cut-offs) to microfiltration MWCOs depending on the separation desired. During membrane filtration, the pH can be varied between 2 and 12, more specifically between 5-10 and more specifically between 7-9 for CMP-SA-PEG.

The membrane filtration step can be used to remove impurities by such techniques as diafiltration and can be used to concentrate the process streams.

Example 5

Cytidine 5'-monophospho N-acetylneuraminic acid (CMP-NAN) is enzymatically synthesized from cytidine 5'-triphosphate (CTP) and N-acetylneuraminic acid (NAN) in the presence of *E. coli*-expressed CMP-NAN Synthetase (CNS). FIG. 1 illustrates the reaction.

CMP-NAN Synthesis Reaction

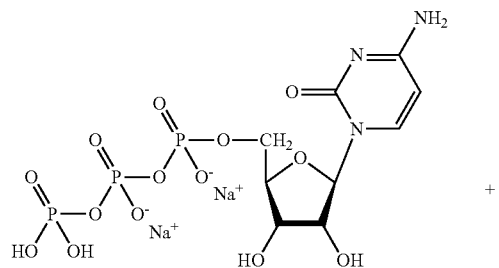

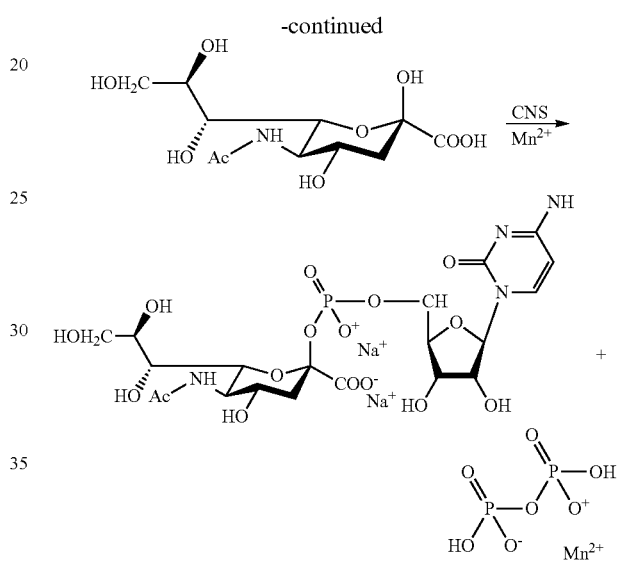

CTP and NAN were incubated in a reactor with CNS and $MnCl_2$. Using a small excess of CTP, the reaction proceeded to almost 100% conversion of NAN to CMP-NAN in under two hours.

The primary by-product of the synthesis reaction was the formation of a manganese phosphate precipitate. Approximate 30% of the final volume of the reaction consisted of this heavy, brown precipitate. In order to remove this precipitate, the solution was filtered. The cake that formed on the filter was washed with water, and the final solution was then filtered to remove any fine particulates that were not held back by the first filtration.

In order to remove proteins introduced from the CNS, the CMP-NAN solution was permeated through a hollow fiber filter. The membrane successfully retains proteins from the enzyme preparation while allowing the passage of CMP-NAN.

Residual salts were then removed from the solution by concentration and diafiltration of the CMP-NAN using a nanofiltration membrane. This membrane retains CMP-NAN during concentration and diafiltration while allowing passage of salts that remain in solution, primarily Tris HCl (the buffer from the enzyme preparation) and NaCl (from the synthesis reaction).

The concentrated CMP-NAN was subsequently decolorized by passing the solution over a pre-packed column of activated carbon. The color is likely from manganese oxide formed during the addition of sodium hydroxide to control the pH during synthesis.

Finally, endotoxin was removed using a charged media depth filter, and then the CMP-NAN solution was filtered through a 0.2 μm filter and aliquotted into sterile containers.

An aliquot was spray dried and tested. The CMP-NAN purity was 83.3%. The remainder of the material was stored as a frozen liquid at −20° C. A portion of the frozen bulk was lyophilized. This material was analyzed and released per specification RM0300 with a purity of 82%.

Process Summary

Cytidine 5'-monophospho N-Acetylneuraminic acid (CMP-NAN) was synthesized in a temperature and pH controlled vessel from Cytidine 5'-triphosphate (CTP) and sialic acid (NAN) using CMP-NAN Synthetase (CNS) in the presence of $MnCl_2$. The CNS is a recombinant protein cloned from *N. meningitidis* and was expressed in JM109 *E. coli* cells. The reaction proceeded for approximately 1.5 hours with sufficient agitation to keep the precipitate from settling. The resultant CMP-NAN solution was chilled to <20° C., clarified by filtration, and transferred into a mobile tank.

The clarified CMP-NAN solution was concentrated 10 times using a hollow fiber filtration unit and diafiltered with 5 volumes of USP purified water. The CMP-NAN was transferred to a mobile tank and the pH was adjusted. This solution was concentrated 10 times and diafiltered with 6 volumes of USP purified water using a nanofiltration system.

Decolorization was achieved by running the CMP-NAN through an activated carbon column and endotoxin was removed using a CUNO Zeta Plus 60ZA filter.

The purified CMP-NAN solution was then aseptically filtered (CUNO LifeASSURE 0.2 μm) and aliquoted into MITOS Sugar Nucleotide Bags and stored at −20° C.

Consistency Runs

Three consistency runs were performed at the 20 L scale before the Engineering Trial took place. The tables below summarize the yields and recoveries and some of the analysis results.

Consistency Runs Summary Data

| Batch | Synthesis Yield | Theoretical Yield | Overall Process Yield | Purification Recovery |
|---|---|---|---|---|
| 1 | 1339 g | 98.1% | 607.8 g | 45.4% |
| 2 | 1264 g | 92.6% | 793.6 g | 62.7% |
| 3 | 1373 g | 100.6% | 952.0 g | 69.3% |

Analysis Results from Consistency Runs

| Chemical Component | Batch #1 | Batch #2 | Batch #3 |
|---|---|---|---|
| CMP-NAN | 75.0% | 77.5% | 82.5% |
| CMP | 5.6% | 5.0% | 5.0% |
| CDP | 0% | 0.5% | 0% |
| NAN | 9.4% | 8.5% | 4.6% |
| Moisture | 7.5% | 7.3% | 7.7% |
| Mass Balance | 97.5% | 98.8% | 99.8% |
| Other Impurities $PO_4$ | 0.2% | 0.9% | 0.4% |

| Property | Requirement | Result |
|---|---|---|
| Appearance | White to off-white powder | White powder |
| Identification | Compares to reference spectra | Compares to reference spectra |
| Moisture Content | ≤5% moisture | 5% |
| Purity | ≥80% CMP-NAN | 82% |
| Percent CMP, CDP and CTP | ≤10% CMP, CDP, and CTP | 5% |
| Manganese by ICP | Report Results | 120 ppm |
| Sodium % by ICP | Report Results | 7.5% |
| Heavy Metals (as Pb) | Report Results | <20 ppm |
| Host Cell Protein | Report Results | Non detected |
| Total Aerobic Count | ≤10 cfu/mg | <1 cfu/mg |
| Yeast and Mold | ≤10 cfu/mg | <1 cfu/mg |
| Endotoxin | ≤0.5 EU/mg | .00165 EU/mg |

Example 6

Synthesis and Purification of CMP-Sialic Acid-PEG 30 kDa

This example describes the preparation and purification of CMP-SA-PEG 30 kDa (compound 3, below). The mPEG-p-nitrophenyl carbonate-30 kDa (compound 1, below) was reacted with sodium CMP-SA-Glycine (compound 2, below) in a mixture of THF/Water. The crude product was desalted by Tangential Flow Filtration (TFF), purified by Q Sepharose chromatography (IEX), and again desalted by TFF to provide 13.5 g of CMP-SA-PEG-30 kDa product (compound 3, below). Reprocessing of mixed IEX fractions afforded an additional 8.2 grams of 3 (overall yield 72.3%).

Scheme 1

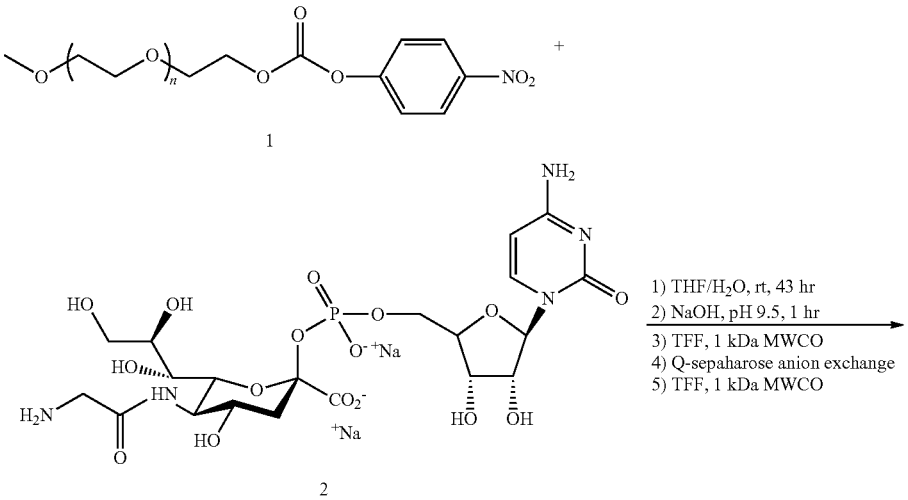

-continued

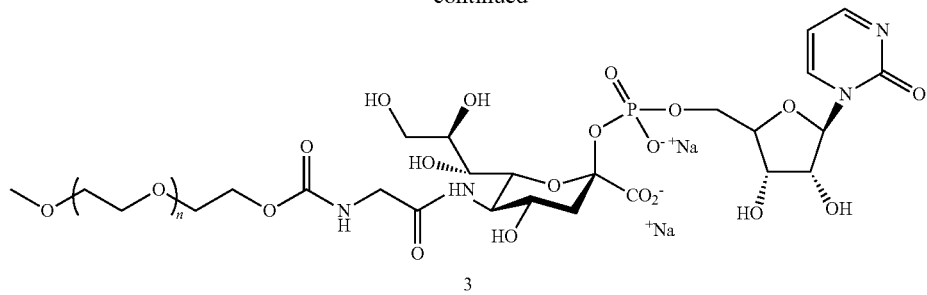

3

I. Materials and Methods
Materials

| Name | Unit |
|---|---|
| Q Sepharose | Big Beads |
| Double 1K Pellicon-2 "MINI" filters | PBLC 1K Regen. Cellulose Membrane; Screen Type: V; 0.1 m² |
| CMP-SA-Glycine (2) Dimethylamine salt | Powder |
| 30K mPEG-p-nitrophenyl carbonate (1) (obtained from NOF America) | Powder |
| NaCl | Powder |
| NaOH | 1.0 N |
| Tris-Glycine gel, 4-20% | 1.0 mm, 10 wells |
| SeeBlue-plus2 Standard | 12 proteins |
| Tris-Glycine Running Buffer | 10x concentrated |
| Tris-Glycine Sample Buffer | 50 mL solution |
| BaCl₂ | Powder |
| Iodine Solution | N/10 |
| Sodium Bicarbonate | Powder |

II. Reaction Conditions.

CMP-SA-Glycine (dimethyl amine salt form, 1.35 g, 2.0 mmole) was dissolved in 20 mL $H_2O$, and the pH was adjusted to 10.5 with 0.1N NaOH (~20 mL). The basic solution was degassed under reduced pressure (vacuum 30 min), frozen and lyophilized to dryness. The resulting sodium CMP-SA-Glycine was redissolved in water (80 mL). The pH was measured and found to be 8.5. The pH was adjusted to 7.8 by addition of 0.2 N $NaH_2PO_4$ (<1.0 mL) and the resulting solution was diluted with THF (200 mL). The mPEG-p-nitrophenyl carbonate-30 kDa (30.0 g, 1 mmol) was added to the CMP-SA-Glycine solution in small portions over 3 hr at room temperature. The reaction mixture was stirred at room temperature for 43 hrs. The THF was then removed by rotary evaporation at reduced pressure without heating (water bath temperature at or below 30° C.). The aqueous residue (80 mL) was diluted with water to 600 mL, and adjusted to pH 9.5 with 1.0N NaOH (about 1.0 mL). The basic solution was stirred at room temperature for 1 hour to hydrolyze any unreacted mPEG-p-nitrophenyl carbonate-30 kDa, and then purified by Tangential Flow Filtration (TFF), Q-Sepharose chromatography (IEX), and then TFF as described below. The final purified fractions were freeze-dried to afford 21.7 g (72.3%) of a white solid (3).

III. Tangential Flow Filtration (TFF) Purification

A Watson-Marlow peristaltic pump (505S) was connected through Tygon tubing (¼" ID) to a Millipore Pellicon-2 Mini Holder equipped with two Millipore 1K Pellicon 2 "MINI" filter (PLAC-V 1K Regenerated Cellulose Membrane; Screen Type: V; 0.1 m2) (FIG. 1). The crude aqueous product solution (500 mL, pH 9.5) from above was transferred to a 1000 mL bottle immersed in an ice bath, equipped with a conductivity meter and a pH meter. The product solution was fed onto the Pellicon Mini filter through Tygon tubing (¼" ID) for diafiltration with a pump speed of 90 rpm (Cross flow rate: 430 mL/min; Flux rate: 20 mL/min; Pressure 13 psi). The retentate solution was returned to the bottle containing the bulk chilled product solution (PharMed tubing, ¼" ID) which was maintained at a constant volume (600 mL) by addition of cold DI water (4° C.). The permeate solution was collected in 2 L fractions. The pH and conductivity values of the retentate/product solution were measured and recorded over time as shown in the table below. The pH of the retentate/product solution was maintained above pH 7.5 by the dropwise addition of 1.0N NaOH, as needed. The retentate/product solution was diafiltered until the conductivity dropped below 0.8 mS, and then the retentate/product solution was allowed to concentrate to a volume of 500 mL. The concentrated retentate was then purified by anion exchange chromatography as described below. The permeate fractions were checked for product break-through by SDS-PAGE as described below:

| Time (min.) | Conductivity (mS) | pH Value | Total Vol (mL) |
|---|---|---|---|
| 0 | 1.93 | 9.58 | 600 |
| 30 | 1.59 | 9.50 | 600 |
| 60 | 1.10 | 9.07 | 600 |
| 90 | 0.899 | 8.69 | 600 |
| 120 | 0.818 | 8.47 | 600 |
| 150 | 0.743 | 8.35 | 600 |
| 180 | 0.755 | 8.56 | 500 |

IV. SDS-PAGE Analysis.

Samples of the TFF permeate fractions (0.5 mL) were concentrated to dryness under a stream of $N_2$ gas, resuspended in 10 µL water and mixed with 10 µL Tris-Gly SDS-PAGE sample buffer and loaded onto 4-20% polyacrylamide Tris-Gly SDS-PAGE gels. See Blue Plus2 protein standard was also loaded as a marker. Gels were run at a constant voltage of 125 V for 1 hr 50 min. After electrophoresis, the gels were washed with water (100 mL) for 10 min, and then incubated with a 5% barium chloride aqueous solution for 10 min Iodine solution (0.1N, 4.0 mL) was added to visualize any mPEG present. The staining process was stopped by washing the gels with water. The proteins used as a standard were a mix of myosin (250 kDa), phosphorylase (148 kDa), BSA (98 kDa), glutamic dehydrogenase (64 kDa), alcohol dehydrogenase (50 kDa), carbonic anhydrase (36 kDa), lysozyme (22 kDa), aprotinin (6 kDa), and insulin B-chain (4 kDa). The gels were visualized and scanned with an HP Scanjet 7400C, and the image of the gel was optimized with the HP Precision Scan Program.

V. Anion Exchange Column Chromatography (IEX) Purification.

Figure 2:
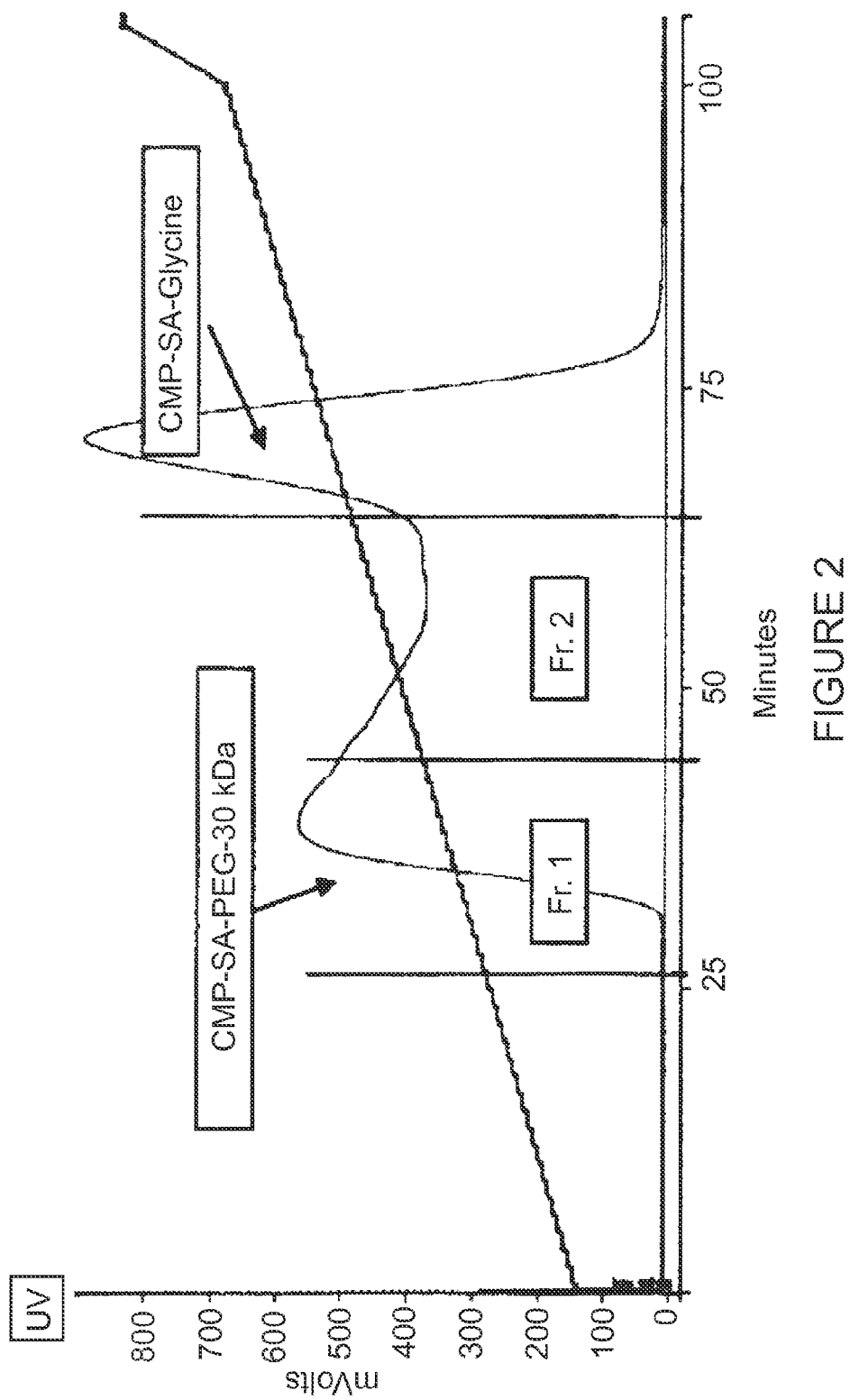
FIG. 2 is a chromatogram recorded for an exemplary purification of CMP-SA-PEG-30 kDa using Q Sepharose chromatography as described in Example 6. CMP-SA-PEG-30 kDa was collected in two fractions. Fraction 1 contained pure product and Fraction 2 contained residual CMP-SA-Gly reagent and was reprocessed.
Figure 3:
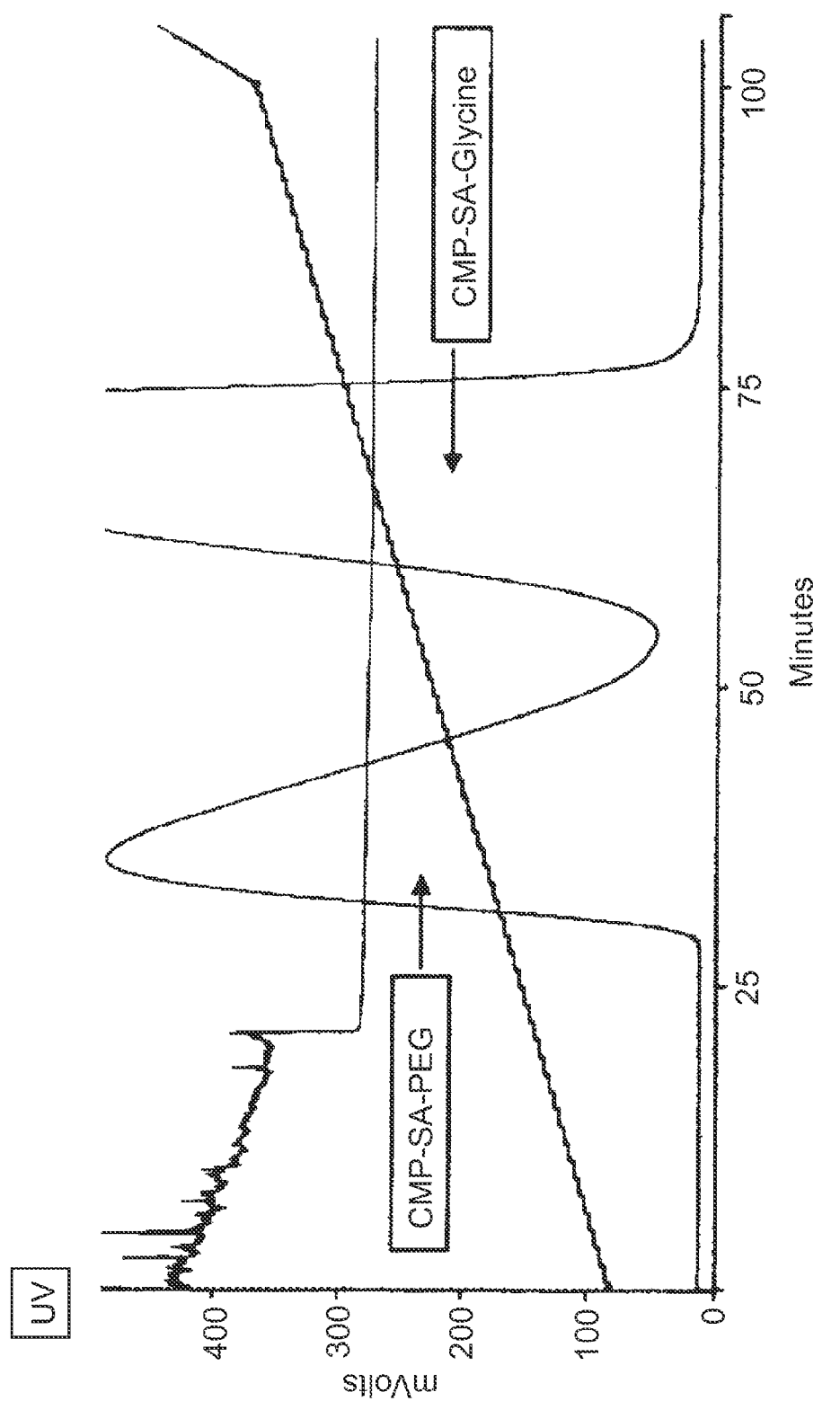
FIG. 3 is a chromatogram recorded for an exemplary separation of CMP-SA-PEG 30 kDa from CMP-SA-Glycine using Q-Sepharose chromatography, showing a typical baseline separation.

The Q Sepharose Big Beads (4.0 L) were treated with 1.0 M NaOH (8.0 L), and then with saturated aqueous sodium bicarbonate (8.0 L) to generate the bicarbonate form of the resin. The newly generated resin was packed in a 17×18 cm (ID) column which was connected to an HPLC system equipped with a UV (274 nm) and an ELS detector (Evaporation temp: 120° C.; Nebulizer temp: 90° C.; Gas flow rate: 1.85 SLM). The TFF retentate from above was slowly, loaded on the Q column (60 mL/min.). The column was then washed with solvent A (cold Di water, 8.0 L) at a flow rate of 125 mL/min until ELS detection indicated that all non-binding impurities (mPEG-OH) had been washed from the column. The product was then eluted with a gradient of 90% Solvent A/10% Solvent B (1.0N NaCl) to 20% Solvent A/80% Solvent B over 100 min, and then to 100% B for 5 minutes at a flow rate of 125 ml/min. Product-containing fractions were collected (detected by UV, 274 nM) as shown in FIG. 2. Fraction 1 was desalted by TFF as described below. Fraction 2 was reprocessed (data not shown).

VI. Tangential Flow Filtration (TFF) for Desalting.

The first fraction (Fraction 1) of the ion-exchange-purified product was desalted using the TFF procedure described above. Upon reaching a constant conductivity, the retentate/product solution was allowed to concentrate to 400 mL. The final retentate (400 mL) was freeze-dried to yield 13.5 g of white solid.

| Time (min.) | Conductivity (mS) | pH Value | Total Vol (mL) |
|---|---|---|---|
| 0 | 23.9 | 7.79 | 600 |
| 30 | 23.1 | 7.81 | 600 |
| 120 | 10.8 | 7.91 | 600 |
| 150 | 8.46 | 7.94 | 600 |
| 180 | 5.59 | 8.14 | 600 |
| 210 | 2.68 | 8.30 | 600 |
| 240 | 1.14 | 8.46 | 600 |
| 270 | 0.706 | 8.68 | 600 |
| 300 | 0.489 | 8.81 | 600 |
| 330 | 0.403 | 8.90 | 500 |
| 360 | 0.389 | 8.53 | 400 |

Example 7

Process Description for the Synthesis and Downstream Processing of CMP-NAN

Cytidine-monophospho 5'-N-acetylneuraminic acid (CMP-NAN) is enzymatically synthesized from cytidine 5'-triphosphate (CTP) and N-acetylneuraminic acid (NAN) in the presence of E. coli-expressed CMP-NAN synthetase (CNS).

The reactants (CTP and NAN) are incubated (30° C., pH 8.5-9.5) in a reactor (20 or 40 L Synthesis Reactor, jacketed temperature control is <10° C. to 30° C., manual or automatic pH control is 8.5-9.5, and agitated) with CNS and manganese chloride ($MnCl_2$). Using a small excess of CTP, the reaction proceeds to almost 100% conversion of NAN to the CMP-NAN product in under two hours. When the reaction is complete, the solution is chilled to <10.0° C. Once chilled the process stream is filtered through a 0.5 μm membrane bag filter (CUNO Polynet bag filter with CUNO bag filter housing and pressure-fed (nitrogen) filtration).

In order to remove proteins introduced by the enzyme preparation, the process stream is next permeated through a 10K hollow fiber membrane with a tangential flow filtration (TFF) skid (Amersham Bioscience (formerly AG Technology) 10K MWCO hollow fiber cartridge, temperature control is <10° C., and inlet, outlet and permeate pressure indication is 0-60 psig). The 10K membrane successfully retains proteins from the enzyme preparation while allowing for passage of the CMP-NAN. The result is a protein-free CMP-NAN solution.

Residual salts are then removed from solution by concentration and diafiltration of the CMP-NAN using a nanofiltration membrane with a nanofiltration TFF skid (Millipore Nanomax-50 Helicon RO4 spiral wound membrane cartridge installed on a Millipore Prolab II skid, temperature control is <10° C. and pressure indication is 0-600 psig). This membrane retains CMP-NAN during concentration and diafiltration while allowing passage of salts that remain in solution from the synthesis reaction and hollow fiber filtration.

This concentrated CMP-NAN stream is subsequently decolored by passing the solution over a pre-packed column of activated carbon attached to a Biotage chromatography system (75M activated chromatography column and Biotage skid). The activated carbon efficiently removes the color from the solution in one or two passes of the CMP-NAN stream.

The process is completed by two filtrations. First, the CMP-NAN solution is filtered using a charged media depth filter (CUNO Zeta Plus 60ZA, 1 $ft^2$). Second, the solution is sent through a final 0.2 μm filter that is pre-packaged and sterilized with a bag manifold system (provided by Mitos Technologies) for final filtration and storage. The product can be stored as a frozen solution or dried as a white powder for refrigerated storage.

Example 8

I. Synthesis of CMP-SA-Glycerol-PEG-40 kDa (1)

CMP-SA-glycine (dimethylamine salt) (1.2 g, 1.6 mmole) was converted to the sodium salt form by dissolution in 20 mL water with 0.1N NaOH (15 mL) at pH 10.5. The basic solution was de-gassed and freeze-dried. The resulting sodium CMP-SA-Glycine (4) was dissolved in water (70 mL), the pH was adjusted to 8.0 with 0.2N $NaH_2PO_4$ and THF (170 mL) was added. The mPEG 40 kDa p-nitrophenyl carbonate (3), (30.0 g, 0.7 mmole) was added as a solid in several portions over a 4 hr period. The mixture was stirred at room temperature for 3 days. The solvent was then removed by rotary evaporation at reduced pressure without heating (water bath temperature below 30° C.). The white solid residue was dissolved in water (500 mL), and the pH adjusted to 9.5 with 1.0N NaOH (about 1.0 ml). The basic solution was stirred at room temperature for 1 hour to hydrolyze any unreacted mPEG 40 kDa p-nitrophenyl carbonate. The solution was diafiltered by Tangential Flow Filtration (TFF) as described below (pump speed: 90 rpm; cross flow rate: 430 mL/min; flux rate: 20 mL/min; pressure 13 psi) until the conductivity of the retentate was reduced to 0.73 mS (Table 1). The retentate was loaded (60 mL/min) on a 4.0 L Q-Sepharose (Big Beads) anion exchange column (17×18 cm) that had been generated in the bicarbonate form as described below on an HPLC system equipped with a UV detector (274 nm) and an ELS detector (Evaporation temp: 120° C.; Nebulizer temp: 90° C.; Gas pressure: 2.4 bar). After loading, the column was washed with 8 L of cold water (125 mL/min) until all the non-binding 40 kDa mPEG-OH had been washed from the column and the ELS signal returned to baseline. The ELS detector was then disconnected and the product was eluted from the column with a gradient of 90% solvent A (cold water)/10% solvent B (1.0N NaCl) to 80% solvent B in 100 min; 80-100% B in 5 min at a flow rate of 125 mL/min. The product elution was monitored by UV 274 nm, and the appropriate fractions were collected. The product-containing fraction (fraction 1) was concentrated to 600 mL and desalted using TFF as described above, carefully maintaining the pH>7.5 with cold DI water and 1.0 NaOH, until the conductivity of the retentate was reduced to 0.35 mS (Table 2). The product solution was then allowed to concentrate to 300 mL and was freeze-dried to afford 12.1 (40%) of a white solid (1). The purity was determined be 93% by UV 274 nm (vs. CMP-SA-Gly). IEX fraction 2 was desalted and further purified by Reverse-phase (C18) chromatography to provide an additional 2.15 g (7%, 99% purity by UV 274 nm, data not shown). $^1$H-NMR (500 MHz; D$_2$O) 1.65 (m, 1H, H-3ax, sialic acid), 2.51 (d,d, 1H5 H-3 eq, sialic acid), 3.39 (s, 3H C $\underline{H}_3$O), 3.80 (t, OC$\underline{H}_2$C$\underline{H}_2$O), 4.17-4.36 (m, 5H, H-2, H-3, H-4, H-5, H5' ribose, H-glycine), 6.01 (d, 1H, H-1 ribose), 6.14 (d, 1H, H-5 cytosine), 8.00 (d, 1H, H-6 cytosine).

O-tosylate (Ts) (36.5 g, 1.83 mmol) was added in several portions over one hr. The mixture was stirred at room temperature for 5 days, and then concentrated by rotary evaporation. The residue was diluted with water (900 mL), the pH was measured and found to be 11.4 and the basic solution was stirred at room temperature for 1 hour to hydrolyze any residual 20 kDa mPEG-OTs reagent. The solution was concentrated to 600 mL and diafiltered by TFF as described below until the conductivity of the retentate was reduced to 0.549 mS. The retentate was loaded (100 mL/min) on a 6.0 L Q-Sepharose (Big Beads) anion exchange column (30×18 cm) that had been generated in the hydroxide form as described below on an HPLC system equipped with a UV detector (274 nm) and an ELS detector (Evaporation temp: 120° C.; Nebulizer temp: 80° C.; Gas pressure: 2.4 bar). After loading, the column was washed with 12 L of water (6-100 mL/min) until all the non-binding 20 kDa mPEG-OH had been washed from the column. The column was eluted with a gradient of 85% solvent A (water)/15% solvent B (1.5N

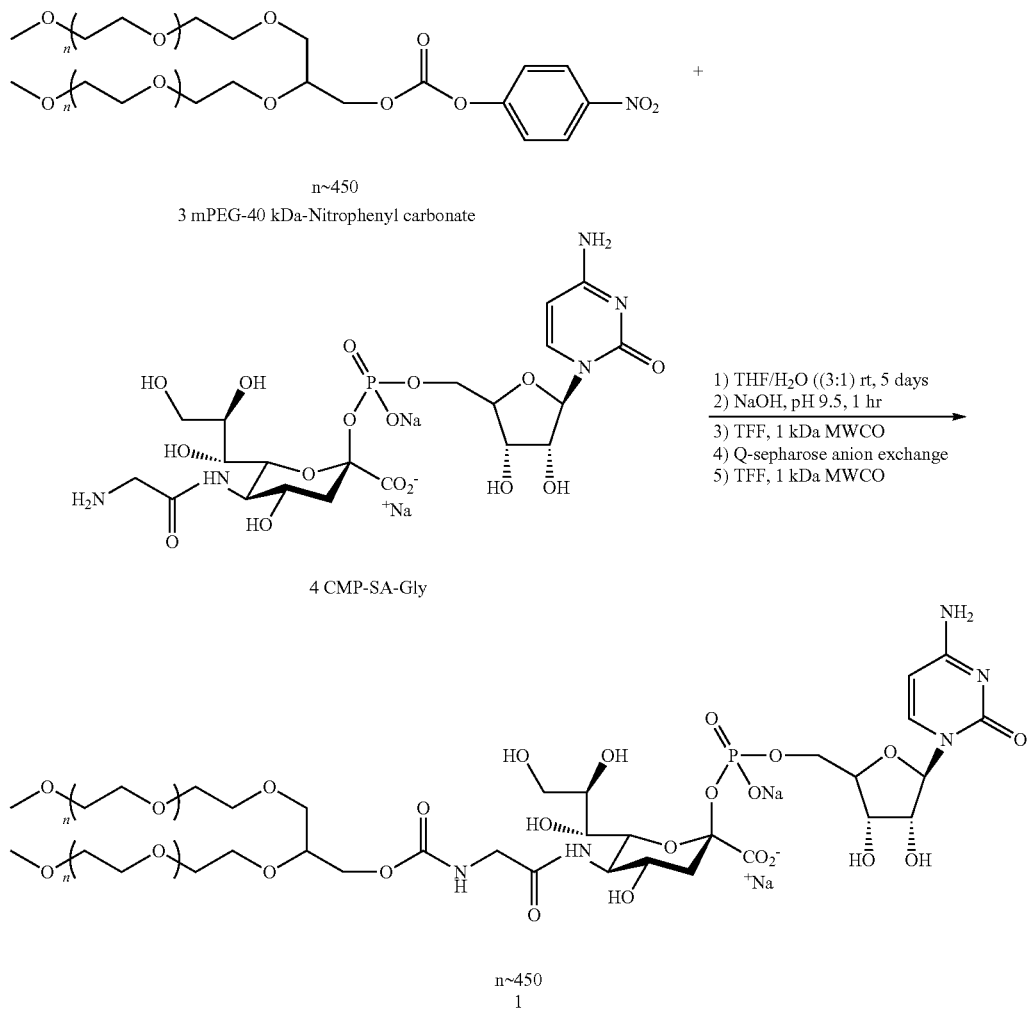

II. Synthesis of L-Cysteine-PEG-20 kDa (5)

Potassium hydroxide (3.4 g, 60.6 mmol) was added as a powder to a solution of L-cysteine (3.4 g, 27.4 mmol) in anhydrous MeOH (1000 mL) under argon. The mixture was stirred at room temperature for 1 hr., and then 20 kDa mPEG- AcOH) to 100% solvent B in 70 min at a flow rate of 125 mL/min. The product elution was monitored by evaporative light scattering (ELS), and the appropriate fractions were collected. The collected fractions were combined and then loaded on a reversed phase column (Varian 75L, C-18 silica. 60 mL/min) that had been pre-conditioned as described below (ACN). The column was washed with water (4 L) and then the product was eluted with the following acetonitrile gradient: 100% water to 40% water/60% ACN in 70 min; 40% water/60% ACN to 100% ACN in 10 min and 100% ACN for 5 min at 100 mL/min. The gradient was held for approximately 25 min at 40% water/60% ACN as the product eluted. The product fractions were pooled, concentrated, redissolved in water and freeze-dried to afford 28.4 g (78%) of a white solid (5). $^1$H-NMR (500 MHz; D$_2$O) δ: 2.83 (t, 2H, O—C—CH$_2$—S), 3.05 (q, 1H, S—CHH—CHN), 3.18 (q, 1H, (q, 1H, S—CHH—CHN), 3.38 (s, 3H, CH$_3$O), 3.7 (t, OCH$_2$CH$_2$O), 3.95 (q, 1H, CHN).

III. Synthesis of L-Cysteine-PEG-40 kDa (6)

L-cysteine-PEG-20 kDa (5) (14.0 g, 0.7 mmol) and 20 kDa mPEG-p-nitrophenyl carbonate (26.0 g, 1.3 mmol) were combined, dried by co-evaporation with toluene (2×800 mL), and dissolved in anhydrous CH$_2$Cl$_2$ (700 mL). Triethylamine (0.4 mL) was added dropwise. The reaction mixture was stirred at room temperature for 5 days. The solvent was then removed by rotary evaporation, the residue was dissolved in water (600 mL), and the pH was adjusted to 9.2 with 1.0N NaOH. The basic solution was stirred at room temperature for 2 hours to hydrolyze any residual 20 kDa mPEG-p-nitrophenyl carbonate reagent. The solution was diafiltered by TFF described below (pump speed: 90 rpm; cross flow rate: 430 mL/min; flux rate: 17 mL/min; inlet pressure 15 psi; outlet pressure 13 psi) until the conductivity of the retentate was reduced to 0.165 mS. The retentate was loaded (100 mL/min) on a 6.0 L Q-Sepharose (Big Beads) anion exchange column (30×18 cm) that had been generated in the hydroxide form as described below on an HPLC system equipped with a UV detector (274 nm) and an ELS detector (Evaporation temp: 120° C.; Nebulizer temp: 80° C.; Gas pressure: 2.4 bar). After loading, the column was washed with 12 L of water (7-100 mL/min) until all the non-binding 20 kD mPEG-OH had been washed from the column. The column was eluted with a gradient of 85% solvent A (water)/15% solvent B (1.5N AcOH) to 100% solvent B in 100 min at a flow rate of 130 mL/min. The product elution was monitored by evaporative light scattering (ELS) and fractions were collected and analyzed by SDS-PAGE as described below. The combined product fractions were loaded on a reverse phase column (Varian 75L, C-18 silica. 60 mL/min) that had been pre-conditioned as described below (MeOH:ACN 1:1). The product was eluted with a gradient with water (A) and 1:1 MeOH:ACN (B) while monitoring with ELS detection: 0-70% B in 80 min; 70-100% B in 30 min at a flow rate of 100 mL/min. The gradient was held for approximately 190 min at 64% B as the first peak eluted and then the gradient was resumed until 75% B when the gradient was held again for approximately 70 min while the second peak eluted. The gradient was resumed until 83% B when it was held for approximately 20 min while a third peak eluted. Nine fractions were collected and analyzed by SDS PAGE. Fractions 7-8 contained pure Cys-PEG-40 kDa (6) and were pooled, concentrated, redissolved in water and freeze-dried to afford 13.32 g (48%) of a white solid. Fractions 2-6 were combined and repurified on C18 to remove a trace PEG-20 kDa impurity (data not shown) to afford an additional 5.1 grams (18%) of Cys-PEG-40 kDa product. $^1$H-NMR (500 MHz; D$_2$O) δ: 2.83 (t, 2H, 0-C—CH$_2$—S), 2.95 (t, 2H, 0-C—CH$_2$—S), 3.12 (q, 1H5 S—CHH—CHN), 3.39 (s, 3H CH$_3$O), 3.71 (t, OCH$_2$CH$_2$O). The purity of the product was confirmed by SDS PAGE.

IV. Synthesis of CMP-SA-Cys-PEG-40 kDa (2)

L-cysteine-PEG-40 kDa (6) (10.0 g, 0.25 mmol) was dried by co-evaporation (twice) with anhydrous toluene and dissolved in anhydrous CH$_2$Cl$_2$ (200 mL). The solution was chilled to 0° C. A solution of DMAP (152.7 mg, 1.25 mmol) in 1 mL anhydrous CH$_2$Cl$_2$ and a solution of BOP (342.0 mg, 0.75 mmol) in 1 mL anhydrous CH$_2$Cl$_2$ were added to the chilled PEG solution and the resulting mixture was stirred for 20 min. N-hydroxysuccinimide (118.6 mg, 1.0 mmol) was added and the reaction mixture was stirred at room temperature for 24 hours under Ar. Anhydrous THF (100 ml) was added and the reaction solution was concentrated to about 50 mL by rotary evaporation with no heating (bath temperature less than 30° C.). The concentrated solution was added in 5 mL portions to a solution of CMP-Sialic acid-glycine (4) (sodium salt form, 1.5 g, 2.2 mmol) in 250 mL of H$_2$O (pH 8.0, adjusted by 2% phosphate buffer). The aqueous solution was stirred for 2 days at room temperature, pH 8.0. THF was removed by rotary evaporation, and the residue was diluted with H$_2$O (600 mL). The solution was diafiltered by TFF as described below (pump speed: 90 rpm; cross flow rate: 430 mL/min; flux rate: 20 mL/min; inlet pressure 15 psi; outlet pressure 13 psi) until the conductivity of the retentate was reduced to 0.4 mS and then the solution was concentrated to 500 mL. The retentate was loaded (100 mL/min) on a 6.0 L Q-Sepharose (Big Beads) anion exchange column (30×18 cm) that had been generated in the bicarbonate form as described below on an HPLC system equipped with a UV detector (274 nm) and an ELS detector (Evaporation temp: 99° C.; Nebulizer temp: 90° C.; Gas pressure: 2.4 bar). After loading, the column was washed with 12 L of water (125 mL/min) until all the non-binding impurities had been washed from the column and the ELS signal returned to baseline. The ELS detector was then disconnected and the column was eluted with a gradient of 90% solvent A (cold water)/10% solvent B (1.0N NaCl) to 80% solvent B in 100 min at a flow rate of 125 mL/min. The product elution was monitored at 274 nm, fractions were collected and analyzed by SDS-PAGE. The combined product fractions 1-5 (2.5 L) were loaded on a preconditioned Varian MetaFlash 651, (C-18 silica) column. The column was washed with cold water (2 L) and eluted with a gradient of (A) 1:1 water:MeOH and (B) 1:9 water:MeOH: 0 to 80% mobile phase B in 60 min; 80-100% B in 5 min at a flow rate of 70 mL/min. The product elution was monitored by UV at 274 nm, fractions were collected and analyzed by SDS PAGE. The pure product fractions were pooled, concentrated, redissolved in water and freeze-dried to afford 3.2 g (32%) of a white solid (2). The product was analyzed by SDS-PAGE and purity was determined by UV 274 run (vs. CMP-SA-Gly) to be 93%. $^1$H-NMR (500 MHz; D$_2$O) 1.65 (m, 1H, H-3ax, sialic acid), 2.51 (d,d, 1H, H-3 eq, sialic acid), 2.83 (t, 2H, 0-C—CH$_2$—S), 2.95 (q, 2H, 0-C—CH$_2$—S), 3.12 (q, 1H, S—CHH—CHN), 3.39 (s, 3H CH$_3$O), 3.80 (t, OCH$_2$CH$_2$O) δ 4.17-4.36 (m, 5H, H-2, H-3, H-4, H-5, H5' ribose), 6.01 (d, 1H, H-1 ribose), 6.14 (d, 1H, H-5 cytosine), 8.00 (d, 1H, H-6 cytosine).

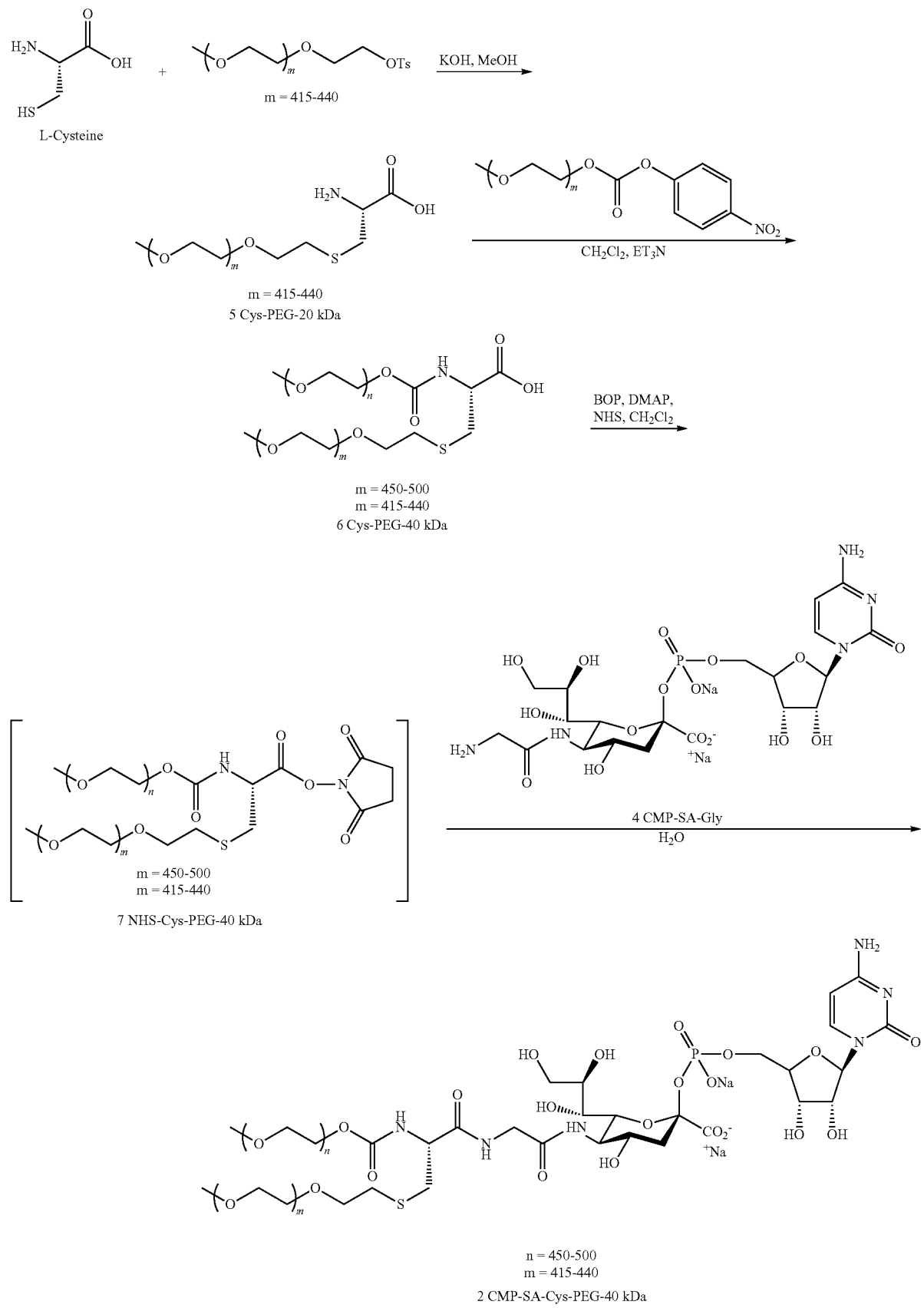

V. General Purification Procedures for Tangential Flow Filtration (TFF)

A Watson-Marlow peristaltic pump (505S) was connected through Tygon tubing (¼" ID) to a Millipore Pellicon-2 Mini Holder equipped with two Millipore 1 kDa Pellicon 2 "MINI" filter (PLAC-V 1 kDa Regenerated Cellulose Membrane; Screen Type: V; 0.1 m²). The aqueous product solution to be filtered was transferred to a 1000 mL bottle immersed in an ice bath, equipped with a conductivity meter and a pH meter. The product solution was fed onto the Pellicon Mini filter through Tygon tubing (¼" ID) for diafiltration with a pump speed of 90 rpm (Cross flow rate: 430 mL/min; Flux rate: 20 mL/min; Pressure 15 psi) unless otherwise noted. The retentate solution was returned to the bottle containing the bulk chilled product solution (PharMed tubing, ¼"ID) which was maintained at a constant volume (600 mL) by addition of cold DI water (4° C.). The permeate solution was collected in 2 L fractions. The pH and conductivity values of the retentate/product solution were measured and recorded over time. The pH of the retentate/product solution was maintained above pH 7.5 by the dropwise addition of 1.0N NaOH, as needed. The product solution was diafiltered until the conductivity dropped below 0.8 mS, and then the volume of the retentate was allowed to concentrate to the desired volume (300 to 500 mL). The retentate was then purified by anion exchange chromatography or freeze dried as described above. Samples of the permeate fractions (0.5 mL) were dried under a stream of $N_2$ gas, redissolved in water (10 µL) and analyzed by SDS-PAGE as described below to check for product breakthrough.

VI. General Purification Procedures by Anion Exchange Column Chromatography (IEX)

Hydroxide Form. Q-Sepharose (Big Beads) ion-exchange resin (6.0 L) was treated with 1.0M NaOH (12.0 L) and $H_2O$ (18.0 L) to generate the hydroxide form of the resin. The newly generated resin was packed in a 30×18 cm (ID) column which was connected to an HPLC system equipped with a UV (274 nm) and an ELS detector. TFF retentate for L-Cys-PEG-20 kDa (5) or L-Cys-PEG-40 kDa (6) were loaded and purified as described above.

Bicarbonate Form. Q-Sepharose (Big Beads) ion-exchange resin (6.0 L) in the hydroxide form (see above) was treated with saturated aqueous sodium bicarbonate (12.0 L) and $H_2O$ (12.0 L) to generate the bicarbonate form of the resin. The newly generated resin was packed in a 30×18 cm (ID) column which was connected to an HPLC system equipped with a UV (274 nm) and an ELS detector. TFF retentate for CMP-SA-Glycerol-PEG-40 kDa (1) or CMP-SA-Cys-PEG-40 kDa (2) were loaded and purified as described above.

General Purification Procedures by Reverse-Phase C18 Column

A Varian MetaFlash 65I or 75L C18-silica cartridge was pre-equilibrated with 2 column volumes (CV) of organic solvent, (MeOH5 acetonitrile, or a 1:1 mixture of MeOH and acetonitrile) followed by a 3 CV gradient of 100% of organic solvent to 100% water, and finally 3 CV of 100% water at 60 mL/min. The IEX-purified PEG reagents were then loaded onto the prepared C18 column and purified as described above.

The CMP-SA-PEG conjugates above are purified by TFF, anion exchange (IEX) chromatography and reverse-phase (C18) chromatography, in this or any suitable order. An alternate purification strategy relies on more than one cycle of TFF, e.g., TFF, anion exchange (IEX) chromatography and TFF.

VI. General Procedures for SDS-PAGE Analysis

PEG samples were analyzed on Tris-Glycine SDS PAGE gels (4-20% polyacryamide, Invitrogen). Typically a reaction sample or chromatography fraction sample was mixed (1:1) with SDS Sample Buffer, and loaded on the gel. See Blue Plus2 protein standard was also loaded as a marker. Gels were run using Tris-Glycine Running Buffer at a constant voltage (125 V) for 1 hr 50 min. After electrophoresis, the gels were washed with water (100 mL) for 10 min, and then incubated with a 5% barium chloride aqueous solution for 10 min. Iodine solution (0.1N, 4.0 mL) was added to o visualize any mPEG present. The staining process was stopped by washing the gels with water. The proteins used as a standard were a mix of myosin (250 kDa), phosphorylase (148 kDa), BSA (98 kDa, glutamic dehydrogenase (64 kDa), alcohol dehydrogenase (50 kDa), carbonic anhydrase (36 kDa), lysozyme (22 kDa), aprotinin (6 kDa), and insulin B-chain (4 kDa). The gels were visualized and scanned with an HP ScanJet 7400C, and the image of the gel was optimized with the HP Precision Scan Program.

All publications, patents and patent applications mentioned in this specification are herein incorporated by reference into the specification to the same extent as if each individual publication, patent or patent application was specifically and individually indicated to be incorporated herein by reference.

What is claimed is:

1. A method of removing essentially all of a contaminant from a mixture comprising the contaminant and a nucleotide sugar comprising a branched PEG structure, the method comprising:
   contacting the mixture with a first membrane for a length of time sufficient to allow essentially all of the contaminant to pass through the first membrane wherein
   the mixture has a pH such that the first membrane and the nucleotide sugar comprising a branched PEG structure have a net charge of the same sign and the contaminant has a net charge which is neutral or a sign which is opposite of the sign of the net charge for the first membrane; and
   the first membrane has a molecular weight cut-off that is less than the molecular weight of the nucleotide sugar comprising a branched PEG structure; and
   wherein the branched PEG structure has a formula of:

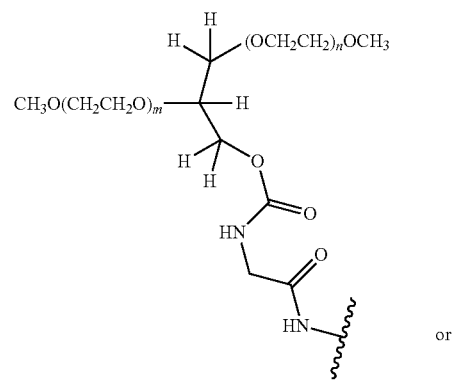

or

-continued

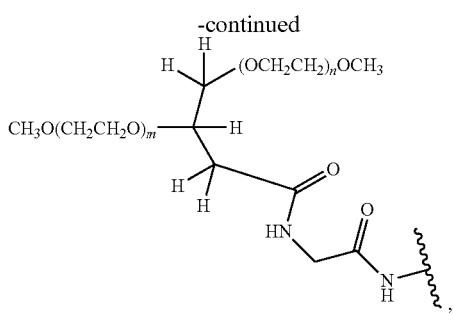

wherein m and n are integers independently selected to provide a PEG moiety having a molecular weight of 2 kDa, 5 kDa, 10 kDa, 20 kDa, 30 kDa, or 40 kDa;
thereby removing essentially all of the contaminant from the mixture.

2. The method according to claim 1, wherein the nucleotide sugar and the first membrane each have a net negative charge and the contaminant has a net charge which is neutral or a net positive charge.

3. The method according to claim 1, wherein the contaminant is a member selected from the group consisting of phosphate, pyrophosphate, nucleotide monophosphate, nucleotide diphosphate, nucleotide triphosphate, sodium phosphate, manganese chloride, sodium pyruvate, GlcNAc, magnesium sulfate, tetrasodium pyrophosphate, lactose, benzoic acid, LNT-2, LNnT, sialic acid, cytidine, CMP, benzyl alcohol, CyLac, cylexin, cytilene and sodium chloride.

4. The method according to claim 1, wherein the first membrane is contacted with at least about 500 mg of the nucleotide sugar.

5. The method according to claim 1, wherein the nucleotide sugar is a member selected from the group consisting of CMP-Sialic Acid, CMP-Nan, GDP-Man, GDP-Fuc, UDP-Glc, UDP-Gal, UDP-GlcNAc, UDP-GalNAc, UDP-GlcA, UDP-IdoA, and UDP-Xyl.

6. The method according to claim 1, wherein, prior to the contacting, the method further comprises forming the mixture by contacting a nucleotide with a sugar and a nucleotide sugar synthetase capable of ligating the nucleotide and the sugar.

7. The method according to claim 1, wherein, prior to the contacting, the method further comprises forming the mixture by subjecting a cell system to conditions whereby the cell system produces a nucleotide sugar.

8. The method according to claim 1, wherein the mixture is not further purified prior to the contacting.

9. The method according to claim 1, wherein the nucleotide sugar is not further purified after the contacting.

10. The method according to claim 1, wherein the nucleotide sugar is further purified after the contacting.

11. The method according to claim 1, wherein, prior to the contacting, the method further comprises contacting the mixture with a second membrane for a length of time sufficient to allow the nucleotide sugar to pass through the second membrane and to allow molecules with a molecular weight greater than about 500 kDa to be retained in the second membrane.

12. The method according to claim 1, wherein, prior to the contacting, the method further comprises contacting the mixture with a third membrane for a length of time sufficient to allow the nucleotide sugar to pass through the third membrane and to allow molecules with a molecular weight greater than about 10 kDa to be retained in the third membrane.

13. A method of purifying a nucleotide sugar comprising a branched PEG structure from a mixture comprising a phosphorus-containing contaminant and the nucleotide sugar comprising a branched PEG structure, the method comprising:
contacting the mixture with a first membrane for a length of time sufficient to allow essentially all of the phosphorus-containing contaminant to pass through the first membrane
wherein
the mixture has a pH such that the first membrane and the nucleotide sugar comprising a branched PEG structure have a net negative charge and the contaminant has a net charge which is a neutral or a positive charge; and
the first membrane has a molecular weight cut-off that is less than the molecular weight of the nucleotide sugar comprising a branched PEG structure; and
wherein the branched PEG structure has a formula of:

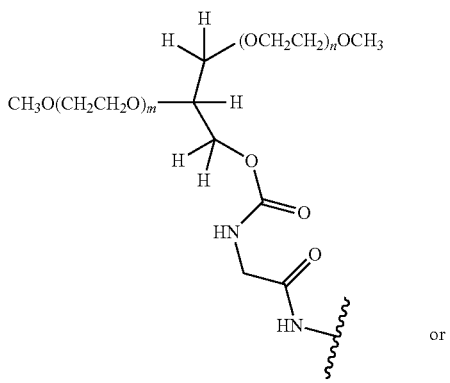

or

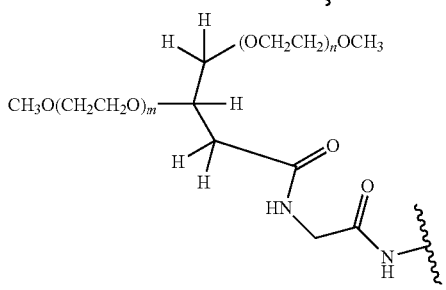

wherein m and n are integers independently selected to provide a PEG moiety having a molecular weight of 2 kDa, 5 kDa, 10 kDa, 20 kDa, 30 kDa, or 40 kDa;
thereby purifying the nucleotide sugar comprising a branched PEG structure from the mixture.

14. The method according to claim 13, wherein the first membrane is contacted with at least about 500 mg of the nucleotide sugar.

15. The method according to claim 13, wherein the nucleotide sugar is a member selected from the group consisting of CMP-Sialic Acid, CMP-Nan, GDP-Man, GDP-Fuc, UDP-Glc, UDP-Gal, UDP-GlcNAc, UDP-GalNAc, UDP-GlcA, UDP-IdoA and UDP-Xyl.

16. A method of removing essentially all of a contaminant from a mixture comprising the contaminant and a nucleotide sugar comprising a branched PEG structure, the method comprising:
contacting the mixture with a first membrane for a length of time sufficient to allow essentially all of the contaminant to pass through the first membrane wherein
the mixture has a pH such that the first membrane and the nucleotide sugar comprising a branched PEG structure have a net charge of the same sign and the contaminant is at its isoelectric point; and
the first membrane has a molecular weight cut-off that is less than the molecular weight of the nucleotide sugar comprising a branched PEG structure; and wherein the branched PEG structure has a formula of:

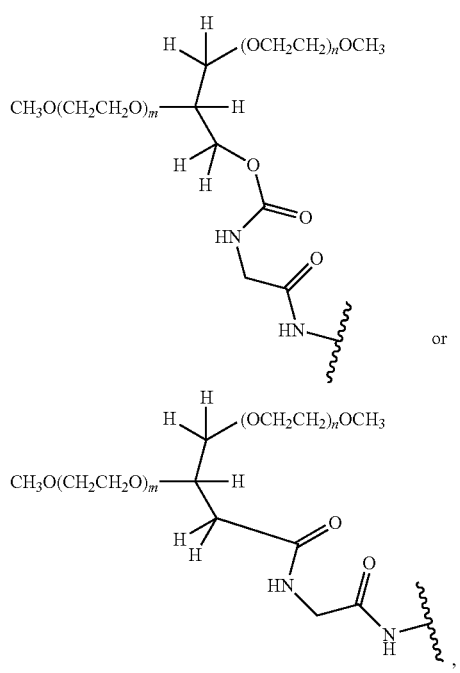

wherein m and n are integers independently selected to provide a PEG moiety having a molecular weight of 2 kDa, 5 kDa, 10 kDa, 20 kDa, 30 kDa, or 40 kDa;

thereby removing essentially all of the contaminant from the mixture.

17. The method according to claim 1, wherein prior to the contacting, a reactive solution comprising the nucleotide sugar is contacted with a nanofiltration membrane, thereby removing a nucleotide monophosphate and a sugar from the reactive solution while retaining the nucleotide sugar in the reactive solution.

18. The method of claim 17, further comprising: passing the reactive solution comprising the nucleotide sugar over a charged media depth filter.

19. The method according to claim 1, wherein the nucleotide sugar is CMP-Sialic Acid.

20. The method according to claim 13, wherein the nucleotide sugar is CMP-Sialic Acid.

21. The method according to claim 16, wherein the nucleotide sugar is CMP-Sialic Acid.

* * * * *

UNITED STATES PATENT AND TRADEMARK OFFICE
CERTIFICATE OF CORRECTION

Page 1 of 2

PATENT NO. : 8,841,439 B2
APPLICATION NO. : 13/215439
DATED : September 23, 2014
INVENTOR(S) : Felo et al.

It is certified that error appears in the above-identified patent and that said Letters Patent is hereby corrected as shown below:

IN THE SPECIFICATION

Column 19, lines 50-51, "$A^{11}$ represent" should read -- $A^{11}$ independently represent --

Column 56, line 39, "0.1N" should read -- 0.1 N --

Column 56, line 42, "0.2N" should read -- 0.2 N --

Column 56, line 50, "1.0N" should read -- 1.0 N --

Column 57, line 1, "(1.0N" should read -- (1.0 N --

Column 57, line 16, "(d,d, 1H5 H-3 eq, sialic acid)" should read -- (d,d, 1H5 H-3eq, sialic acid) --

Column 58, line 19, "(1.5N" should read -- (1.5 N --

Column 59, line 23, "1.0N" should read -- 1.0 N --

Column 59, line 41, "(1.5N" should read -- (1.5 N --

Column 60, line 44, "(1.0N" should read -- (1.0 N --

Column 60, line 48, "65I," should read -- 65I, --

Column 60, line 61, "(d,d, 1H, H-3 eq, sialic acid)," should read -- (d,d, 1H, H-3eq, sialic acid), --

Column 60, line 63, "(t, OC$\underline{H}_2$C$\underline{H}_2$O) δ" should read -- (t, OC$\underline{H}_2$C$\underline{H}_2$O)5 --

Column 63, line 23, "1.0N" should read -- 1.0 N --

Signed and Sealed this
Tenth Day of March, 2015

Michelle K. Lee
*Deputy Director of the United States Patent and Trademark Office*

CERTIFICATE OF CORRECTION (continued)
U.S. Pat. No. 8,841,439 B2

IN THE SPECIFICATION – (Continued)

Column 63, line 38, "1.0M" should read -- 1.0 M --

Column 64, line 16, "(0.1N," should read -- (0.1 N, --